United States Patent
Tamura et al.

(10) Patent No.: US 9,108,975 B2
(45) Date of Patent: Aug. 18, 2015

(54) CRYSTAL OF 6,7-UNSATURATED-7-CARBAMOYL MORPHINAN DERIVATIVE AND METHOD FOR PRODUCING THE SAME

(75) Inventors: Yoshinori Tamura, Toyonaka (JP); Kouichi Noguchi, Amagasaki (JP); Masanao Inagaki, Toyonaka (JP); Kenji Morimoto, Toyonaka (JP); Nobuhiro Haga, Toyonaka (JP); Shinichi Oda, Iwate-ken (JP); Sohei Omura, Amagasaki (JP)

(73) Assignee: Shionogi & Co., LTD., Osaka (JP)

( * ) Notice: Subject to any disclaimer, the term of this patent is extended or adjusted under 35 U.S.C. 154(b) by 0 days.

(21) Appl. No.: 13/884,770

(22) PCT Filed: Nov. 11, 2011

(86) PCT No.: PCT/JP2011/076034
§ 371 (c)(1),
(2), (4) Date: May 10, 2013

(87) PCT Pub. No.: WO2012/063933
PCT Pub. Date: May 18, 2012

(65) Prior Publication Data
US 2013/0231485 A1 Sep. 5, 2013

(30) Foreign Application Priority Data

Nov. 12, 2010 (JP) .................................. 2010-253688

(51) Int. Cl.
| | | |
|---|---|---|
| *C07D 471/00* | (2006.01) | |
| *A61K 31/44* | (2006.01) | |
| *C07D 489/08* | (2006.01) | |
| *C07C 51/41* | (2006.01) | |
| *C07C 53/10* | (2006.01) | |
| *C07C 303/32* | (2006.01) | |
| *C07C 309/30* | (2006.01) | |
| *C07D 271/06* | (2006.01) | |
| *A61K 9/16* | (2006.01) | |

(52) U.S. Cl.
CPC ............ *C07D 489/08* (2013.01); *A61K 9/1629* (2013.01); *C07C 51/412* (2013.01); *C07C 53/10* (2013.01); *C07C 303/32* (2013.01); *C07C 309/30* (2013.01); *C07D 271/06* (2013.01)

(58) Field of Classification Search
None
See application file for complete search history.

(56) References Cited

U.S. PATENT DOCUMENTS

2009/0203723 A1 8/2009 Inagaki et al.

FOREIGN PATENT DOCUMENTS

| WO | WO 01/02375 A1 | 1/2001 |
| WO | WO 2006/126637 A1 | 11/2006 |

OTHER PUBLICATIONS

Vippagunta Adv Drug Deliv Rev 2001 vol. 48, pp. 3-26.*
Morissette, S et al Adv Drug Deliv Rev 2004 vol. 56, pp. 275-300.*
English translation of International Preliminary Report on Patentability issued by the Japanese Patent Office in International Application No. PCT/JP2011/076034, mailed May 23, 2013 (10 pages).
International Search Report issued by the Japanese Patent Office in International Application No. PCT/JP2011/076034, mailed Dec. 13, 2011 (9 pages).
D. C. Butler, et al., "Synthesis of isocyanates from carbamate esters employing boron trichloride", Chem. Commun., pp. 2575-2576 (1998).
M. J. Duggan, et al., "Copper(I) Chloride Catalyzed Addition of Alcohols to Alkyl Isocyanates. A Mild and Expedient Method for Alkyl Carbamate Formation", Synthesis, vol. 2, pp. 131-132 (1989).
R. Poulain, et al., "Parallel synthesis of 1,2,4-oxadiazoles from carboxylic acids using an improved, uronium-based, activation" Tetrahedron Letters, 42, pp. 1495-1498 (2001).
T. Okano. "Forms of powder and granular substances", New General Pharmacy (revised $3^{rd}$ edition), pp. 109-111, 254-259, 327 (1987).
T. Okano, "Chemical structure and solubility", New General Pharmacy (revised $3^{rd}$ edition), pp. 26, 111, 266-258 (1987).

(Continued)

*Primary Examiner* — Heidi Reese
(74) *Attorney, Agent, or Firm* — Finnegan, Henderson, Farabow, Garrett & Dunner LLP

(57) ABSTRACT

Stable crystalline forms of a compound represented by the formula (IA):

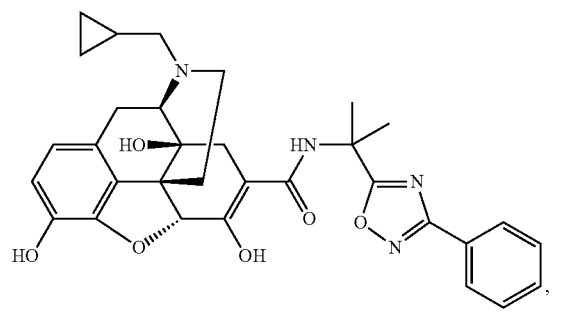

(IA)

an acid addition salt, and/or a solvate thereof are provided by the present invention. Said crystalline forms are extremely useful as materials for preparing medicines. Novel processes for preparing 6,7-unsaturated-7-carbamoyl morphinan derivatives are also provided by the present invention.

18 Claims, 26 Drawing Sheets

(56) References Cited

OTHER PUBLICATIONS

B. D. Anderson, et al., "Preparation of Water-Soluble Compounds Through Salt Formation", C. G. Wermuth editors, The Practice of Medicinal Chemistry, vol. 2, (Technomic Inc.), pp. 739-741, 750-753, 831-833, (1996).

* cited by examiner

CRYSTAL OF 6,7-UNSATURATED-7-CARBAMOYL MORPHINAN DERIVATIVE AND METHOD FOR PRODUCING THE SAME

This application is national phase application based on PCT/JP2011/076034, filed Nov. 11, 2011, which claims the priority of Japanese Patent Application No. 2010-253688, filed Nov. 12, 2010, the content of both applications being incorporated herein by reference.

TECHNICAL FIELD

The present invention relates to crystal of a morphinan derivative and a method for producing the same. In more detail, the present invention relates to crystal of a 6,7-unsaturated-7-carbamoyl morphinan derivative, an acid addition salt thereof and/or solvates thereof, and a method for producing the same.

BACKGROUND ART

In a drug delivery, crystalline forms having useful and outstanding chemical and/or physical properties are desired.

The patent document 1 describes that a 6,7-unsaturated-7-carbamoyl morphinan derivative represented by the following formula:

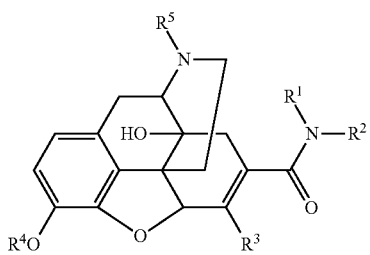

is useful as a therapeutic and/or prophylactic agent of the emesis and/or constipation. Although the following compound (I-284):

(I-284)

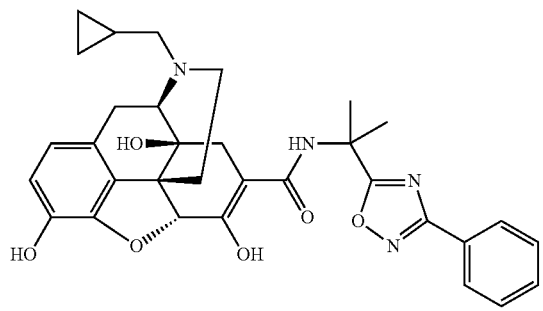

is disclosed in a form of free salt in Examples of the patent, an acid addition salt and/or a solvate are not specifically disclosed. Further, there is no description at all about the crystal thereof.

As a method for preparing the 6,7-unsaturated-7-carbamoyl morphinan derivative, all that disclosed is a method for synthesizing a corresponding 7-carbamoyl derivative from 7-carboxy derivative as shown by the following formula:

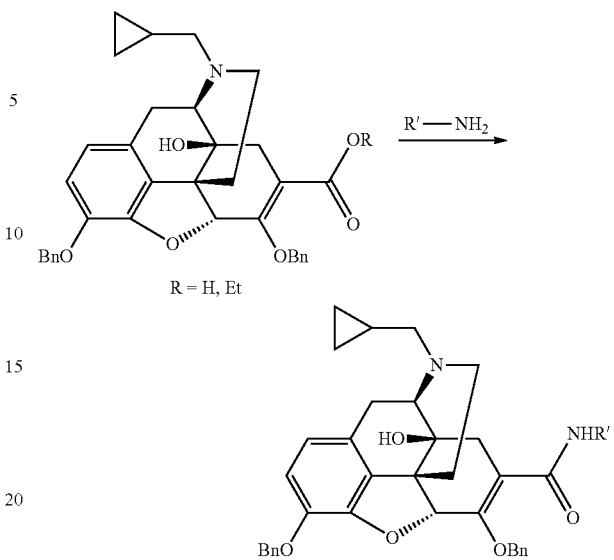

R = H, Et

PRIOR ART DOCUMENT

Patent Documents

[Patent document 1] International Patent Application Publication WO 2006/126637

[Patent document 2] International Patent Application Publication WO 2001/002375

Nonpatent Documents

[Nonpatent document 1] Chemical Communications, 1998, vol. 23, 2575-2576

[Nonpatent document 2] Synthesis, 1989, vol. 2, 131-132

SUMMARY OF INVENTION

Problems to be Solved by the Invention

An active ingredient of a medicine may have substantially different physical properties depending on each solid form. Differences in such physical properties may affect a preparation method or administration method of the medicinal active ingredient, or a pharmaceutical composition comprising the active ingredient, for example.

Although the 6,7-unsaturated-7-carbamoyl morphinan derivative is already disclosed, establishment of a suitable salt and/or a stable crystal form and a more desirable method for preparing the same has been desired for the drug use or for the industrial drug production.

Means for Solving the Problems

As a result of extensive investigations, inventors of the present invention have found out that a stable crystal is obtained from a compound represented by the following formula (IA):

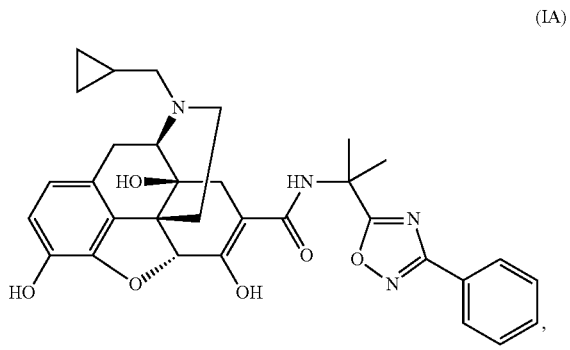 [SMILES: CC(C)(NC(=O)C1=C(O)[C@@H]2Oc3c(O)ccc4c3[C@@]23CCN(CC2CC2)[C@H](C4)[C@]3(O)C1)c1nc(-c2ccccc2)no1]

(IA)

an acid addition salt and/or a solvate thereof, and have completed the following inventions.

The inventors have further found that a compound of the following formula (I):

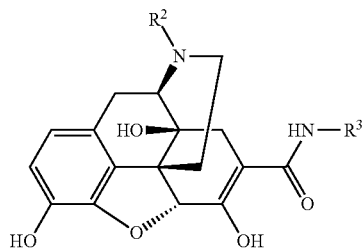

(I)

wherein $R^2$ is an optionally substituted lower alkyl and $R^3$ is an optionally substituted lower alkyl, an optionally substituted cycloalkyl, an optionally substituted aryl or an optionally substituted heteroaryl; is obtained by reacting a carbamate derivative of the following formula (II):

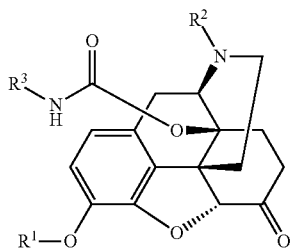

(II)

wherein $R^1$ is hydrogen or a hydroxyl-protecting group and $R^2$ and $R^3$ are the same as defined above; in the presence of a base, and by deprotecting a protective group $R^1$, thus completed the inventions relating to a novel method for preparing the 6,7-unsaturated-7-carbamoyl morphinan derivative.

The present invention provides the followings.
(1) A p-toluenesulfonic acid salt, an acetic acid salt or a hydrochloric acid salt of a compound of the following formula (IA):

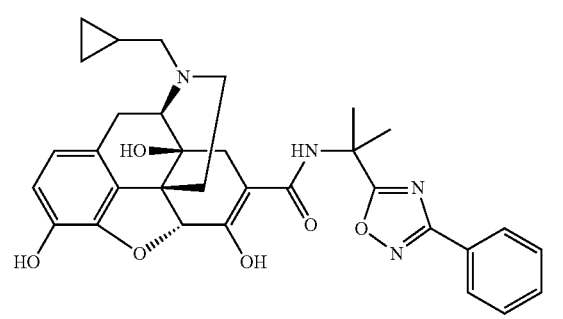

(IA)

or a solvate of the compound or an acid addition salt thereof.
(2) Crystal of a p-toluenesulfonic acid salt of the compound of the following formula (IA):

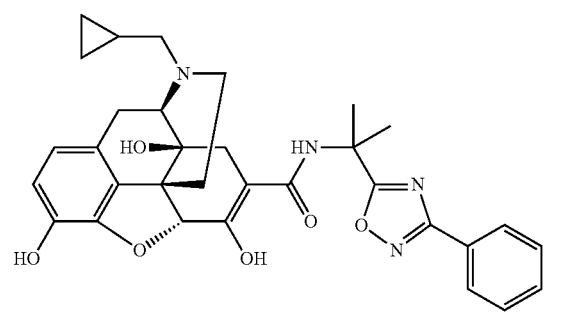

(IA)

or crystal of a solvate of the acid addition salt thereof.
(3) The crystal of the p-toluenesulfonic acid salt according to (2), wherein the crystal has peaks of diffraction angles of (2 θ): 7.8°±0.2° 10.6°±0.2°, 15.6°±0.2°, 17.8°±0.2° and 21.5°±0.2° in an X-ray powder diffraction spectrum.
(4) The crystal of the p-toluenesulfonic acid salt according to (2), wherein the crystal has peaks of diffraction angles of (2 θ): 7.8°±0.2°, 10.6°±0.2°, 15.6°±0.2°, 17.8°±0.2°, 18.6°±0.2°, 20.4°±0.2°, 21.5°±0.2°, 21.9°±0.2°, 23.6°±0.2° and 25.5°±0.2° in an X-ray powder diffraction spectrum.
(5) The crystal of the p-toluenesulfonic acid salt according to (2) characterized by an X-ray powder diffraction spectrum which is substantially identical with FIG. 1.
(6) The form I crystalline form of the p-toluenesulfonic acid salt hydrate according to claim 2, wherein the crystal has peaks of diffraction angles of (2 θ): 12.9°±0.2°, 17.6°±0.2°, 22.4°±0.2°, 25.4°±0.2° and 28.7°±0.2° in an X-ray powder diffraction spectrum.
(7) The form I crystalline form of the p-toluenesulfonic acid salt hydrate according to (2), wherein the crystal has peaks of diffraction angles of (2 θ): 6.6°±0.2°, 8.9°±0.2°, 11.4°±0.2°, 12.9°±0.2°, 14.0°±0.2°, 15.0°±0.2°, 17.6°±0.2°, 18.2°±0.2°, 22.4°±0.2°, 25.4°±0.2° and 28.7°±0.2° in an X-ray powder diffraction spectrum.
(8) The form I crystalline form of the p-toluenesulfonic acid salt hydrate according to (2) characterized by an X-ray powder diffraction spectrum which is substantially identical with FIG. 2.

(9) A form II crystalline form of the p-toluenesulfonic acid salt hydrate according to (2), wherein the crystal has peaks of diffraction angles of (2 θ): 8.8°±0.2°, 17.5°±0.2°, 21.9°±0.2°, 23.7°±0.2° and 26.1°±0.2° in an X-ray powder diffraction spectrum.

(10) The form II crystalline form of the p-toluenesulfonic acid salt hydrate according to (2), wherein the crystal has peaks of diffraction angles of (2 θ): 7.1°±0.2°, 8.8°±0.2°, 17.5°±0.2°, 19.2°±0.2°, 19.7°±0.2°, 21.2°±0.2°, 21.9°±0.2°, 23.7°±0.2°, 24.5°±0.2° and 26.1°±0.2° in an X-ray powder diffraction spectrum.

(11) The form II crystalline form of the p-toluenesulfonic acid salt hydrate according to (2) characterized by an X-ray powder diffraction spectrum which is substantially identical with FIG. 3.

(12) Crystal of an acetic acid salt of a compound of the formula (IA):

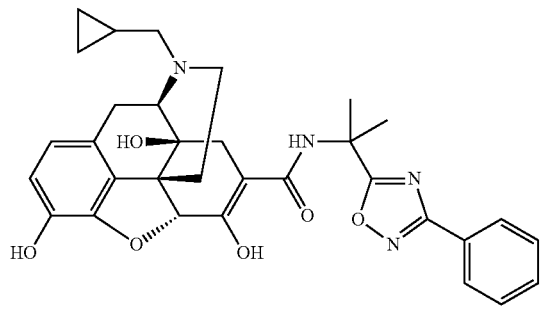

(IA)

or crystal of a solvate of an acid addition salt thereof.

(13) The crystal of the acetic acid salt according to (12), wherein the crystal has peaks of diffraction angles of (2 θ): 5.6°±0.2°, 10.3°±0.2°, 12.0°±0.2°, 14.6°±0.2° and 26.0°±0.2° in an X-ray powder diffraction spectrum.

(14) The crystal of the acetic acid salt according to (12), wherein the crystal has peaks of diffraction angles of (2 θ): 5.6°±0.2°, 8.3°±0.2°, 9.1°±0.2°, 10.3°±0.2°, 12.0°±0.2°, 13.5°±0.2°, 14.6°±0.2°, 16.3°±0.2° and 26.0°±0.2° in an X-ray powder diffraction spectrum.

(15) The crystal of the acetic acid salt according to (12) characterized by the X-ray powder diffraction spectrum which is substantially identical with FIG. 4.

(16) Crystal of a hydrochloric acid salt of the compound of the formula (IA):

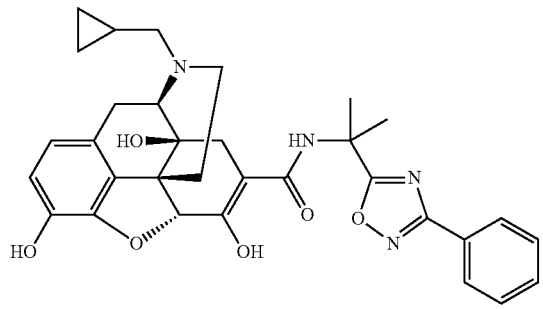

(IA)

or crystal of a solvate of an acid addition salt thereof.

(17) The crystal of the hydrochloric acid salt according to (16), wherein the crystal has peaks of diffraction angles of (2 θ): 8.8°±0.2°, 12.7°±0.2°, 15.6°±0.2°, 17.3°±0.2° and 23.9°±0.2° in an X-ray powder diffraction spectrum.

(18) The crystal of the hydrochloric acid salt according to (16), wherein the crystal has peaks of diffraction angles of (2 θ): 8.5°±0.2°, 10.8°±0.2°, 11.3°±0.2°, 12.7°±0.2°, 13.9°±0.2°, 15.6°±0.2°, 17.3°±0.2°, 19.2°±0.2°, 20.1°±0.2° and 23.9°±0.2° in an X-ray powder diffraction spectrum.

(19) The crystal of the hydrochloric acid salt according to (16) characterized by an X-ray powder diffraction spectrum which is substantially identical with FIG. 5.

(20) Crystal of the compound of the formula (IA):

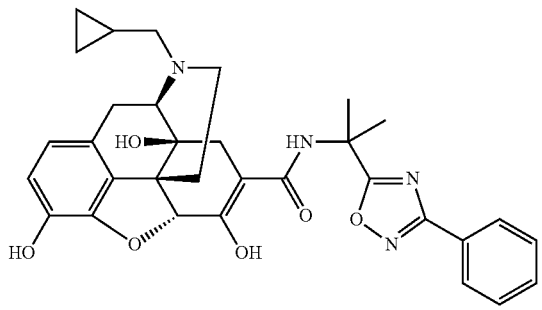

(IA)

or crystal of a solvate thereof.

(21) The crystal of the compound of the formula (IA) according to (20), wherein the crystal has peaks of diffraction angles of (2 θ): 13.5°±0.2°, 21.6°±0.2°, 22.1°±0.2°, 23.4°±0.2° and 26.7°±0.2° in an X-ray powder diffraction spectrum.

(22) The crystal of the compound of the formula (IA) according to (20), wherein the crystal has peaks of diffraction angles of (2 θ): 6.8°±0.2°, 11.7°±0.2°, 13.5°±0.2°, 15.6°±0.2°, 16.7°±0.2°, 21.6°±0.2°, 22.1°±0.2°, 23.4°±0.2°, 26.7°±0.2° and 30.1°±0.2° in an X-ray powder diffraction spectrum.

(23) The crystal of the compound of the formula (IA) according to (20) characterized by an X-ray powder diffraction spectrum which is substantially identical with FIG. 7.

(24) The crystal of the ethanol solvate according to (20), wherein the crystal has peaks of diffraction angles of (2 θ): 11.0°±0.2°, 16.5°±0.2°, 20.5°±0.2°, 21.8°±0.2° and 22.6°±0.2° in an X-ray powder diffraction spectrum.

(25) The crystal of the ethanol solvate according to (20), wherein the crystal has peaks of diffraction angles of (2 θ): 6.9°±0.2°, 11.0°±0.2°, 12.9°±0.2°, 13.4°±0.2°, 16.5°±0.2°, 20.5°±0.2°, 21.3°±0.2°, 21.8°±0.2°, 22.6°±0.2° and 25.1°±0.2° in an X-ray powder diffraction spectrum.

(26) The crystal of the ethanol solvate according to (20) characterized by an X-ray powder diffraction spectrum which is substantially identical with FIG. 6.

(27) A pharmaceutical composition comprising crystal according to any one of (2) to (26).

(27A) An opioid receptor antagonist comprising crystal according to any one of (2)-(26).

(27B) A therapeutic and/or prophylactic agent for nausea, emesis, and/or constipation, wherein the agent comprises crystal according to (2)-(26).

(27C) A mitigating and/or prophylactic agent for a side effect induced by a compound having an opioid receptor agonistic activity, wherein the agent comprises crystal according to any one of (2)-(26).

(27D) The therapeutic and/or prophylactic agent according to (27C), wherein the side effects are nausea, emesis, and/or constipation.

(27E) The therapeutic and/or prophylactic agent according to (27C) or (27D), wherein the compound having an opioid receptor agonistic activity is morphine, oxycodone, hydrocodone, tramadol, or a pharmaceutically acceptable salt or solvate thereof.

(27F) Use of crystal according to any one of (2)-(26) for manufacturing a therapeutic and/or prophylactic agent for nausea, emesis, and/or constipation.

(27G) Use of crystal according to any one of (2)-(26) for manufacturing a mitigating and/or prophylactic agent for side effects induced by a compound having an opioid receptor agonistic activity.

(27H) A therapeutic and/or prophylactic method for nausea, emesis, and/or constipation characterized by administrating a pharmaceutical composition comprising crystal according to (2)-(26).

(27I) A mitigating and/or prophylactic method for the side effect induced by a compound having an opioid receptor agonistic activity comprising the step of administrating crystal according to any one of (2)-(26).

(27J) A pharmaceutical composition comprising crystal according to any one of (2)-(26) for treating and/or preventing nausea, emesis, and/or constipation.

(27K) The pharmaceutical composition comprising crystal according to any one of (2)-(26) for mitigating and/or preventing side effects induced by a compound having an opioid receptor agonistic activity.

(27L) Analgesics comprising a combination of a compound having an opioid receptor agonistic activity with an effective amount of crystal according to any one of (2)-(26) for mitigation and/or prophylaxis of side effects induced by said compound having an opioid receptor agonistic activity.

(27M) Analgesics comprising a combination of a compound having an opioid receptor agonistic activity with an effective amount of crystal according to any one of (2)-(26) for treating and/or preventing nausea, emesis, and/or constipation induced by said compound having an opioid receptor agonistic activity.

(27N) Analgesics according to (27L) or (27M), wherein the compound having an opioid receptor agonistic activity is morphine, oxycodone, hydrocodone, tramadol, madone, or a pharmaceutically acceptable salt or solvate thereof.

(28) A process for preparing crystal of an acid addition salt of a compound of the formula (IA):

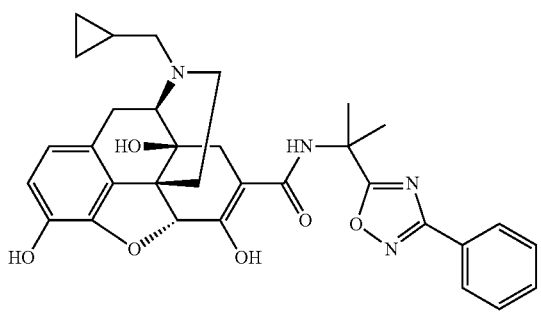

(IA)

or crystal of a solvate of said acid addition salt according to any one of (2) to (19) characterized by steps of adding an acid to the compound of the formula (IA), and then, crystallizing the acid addition salt or a solvate thereof from a solvent if needed.

(29) A process for preparing the crystal according to (2), characterized by the steps of:

treating with a base a compound of the formula (IID):

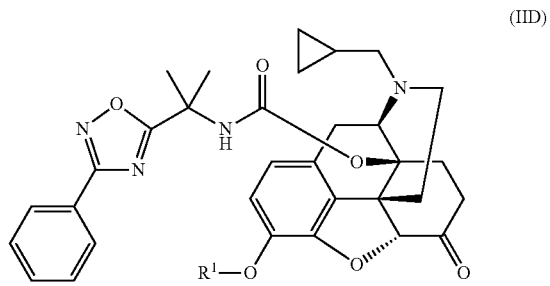

(IID)

wherein $R^1$ is hydrogen or a hydroxyl-protecting group, adding p-toluenesulfonic acid after deprotecting $R^1$ if needed, and crystallizing the acid addition salt or a solvate thereof from a solvent if needed.

(30) The process according to (29), characterized by the steps of:

treating with a base a compound of the formula (IIE):

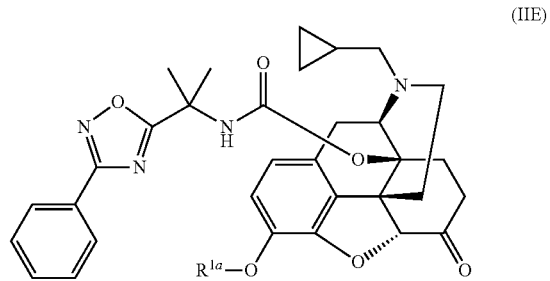

(IIE)

wherein $R^{1a}$ is hydrogen atom or a protective group of hydroxy group deprotectable by a base, then adding p-toluenesulfonic acid thereto, and crystallizing the acid addition salt or a solvate thereof from a solvent, if needed.

(31) A process for preparing a compound of the formula (II):

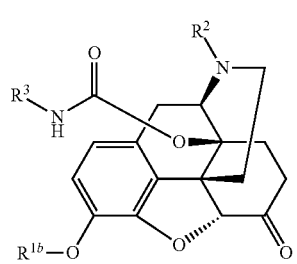

(II)

wherein $R^{1b}$ is a protective group of hydroxy, $R^2$ is an optionally substituted lower alkyl, $R^3$ is an optionally substituted lower alkyl, an optionally substituted cycloalkyl, a substituted or non-substituted aryl or a substituted or non-substituted heteroaryl;

characterized by reacting a compound of the formula (III):

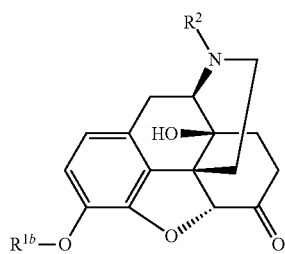
(III)

wherein $R^{1b}$ and $R^2$ are the same as defined above; with a compound of the formula: $R^3$—N=C=O, wherein $R^3$ is the same as defined above; or with a compound of the formula: $R^3$—NH—C(=O)—X, wherein $R^3$ is the same as defined above and X is a leaving group; in the presence or absence of an acid.

(32) The process according to (31), characterized by obtaining the compound of the formula (III):

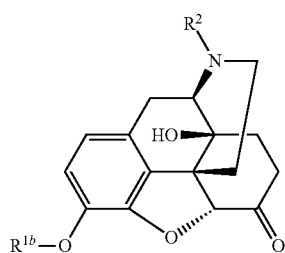
(III)

wherein $R^{1b}$ and $R^2$ is the same as defined in (31);
by protecting a hydroxy group of a compound of the formula (IV):

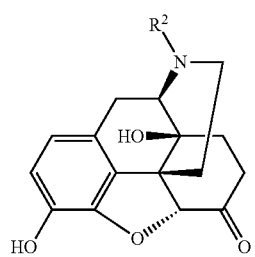
(IV)

wherein $R^2$ is the same as defined in (31).

(33) The process according to (32) wherein the step of obtaining the compound of the formula (III):

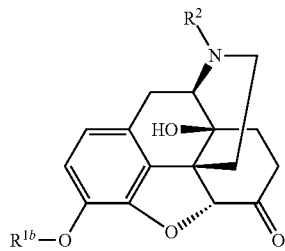
(III)

wherein $R^{1b}$ and $R^2$ are the same as defined in (31);

by protecting a hydroxy group of the compound of the formula (IV):

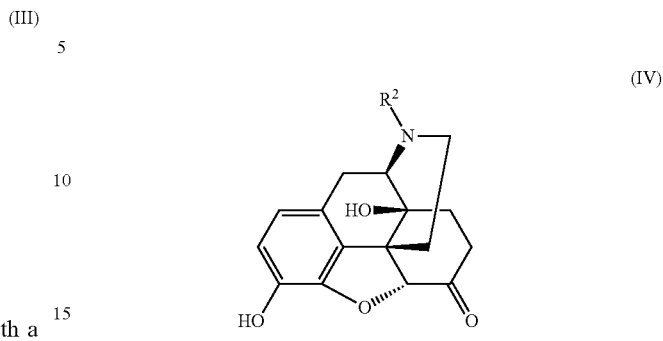
(IV)

wherein $R^2$ is the same as defined in (31);

and a step of reacting the compound of the formula (III) with a compound of the formula: $R^3$—N=C=O, wherein $R^3$ is the same as defined in (31); or with a compound of the formula: $R^3$—NH—C(=O)—X, wherein $R^3$ is the same as defined above and X is a leaving group;

in the presence or absence of an acid, are successively carried out.

Wherein the phrase "successively carried out" includes that a reaction of the next step is carried out without isolating the compound prepared by the reaction of the preceding step.

For example, carried out in two steps in one pot is exemplified.

(34) The process according to any one of (31) to (33), wherein a reaction is carried out in the presence of an acid.

(35) The process according to (34), wherein the acid is a Lewis acid.

(36) The process according to (35), wherein the Lewis acid is CuCl, CuCl$_2$, CuBr, CuI, CuBr, CuSO$_4$, Cu, Zn(OAc)$_2$, ZnBr$_2$ or ZnCl$_2$.

(37) The process according to any one of (31) to (36) characterized in that the reaction is carried out in the presence of an acid of about 0.00005-1.0 equivalents to the compound of the formula (III).

(38) The process according to any one of (31) to (37), wherein $R^{1b}$ is a protective group of hydroxyl deprotectable by a base.

(39) A process for preparing a compound of the formula (I):

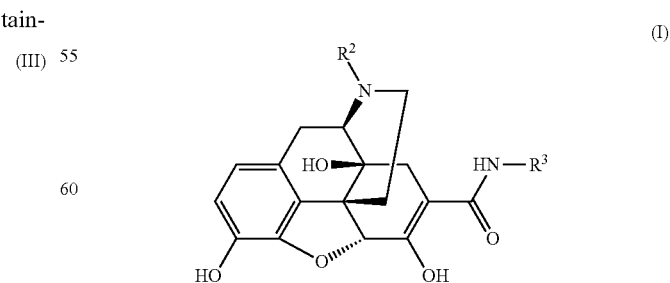
(I)

wherein $R^2$ and $R^3$ are the same as defined in (31); by treating with a base a compound of the formula (IIA):

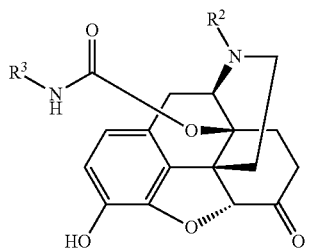
(IIA)

wherein $R^2$ and $R^3$ are the same as defined above.

(40) A process for preparing a compound of the formula (I):

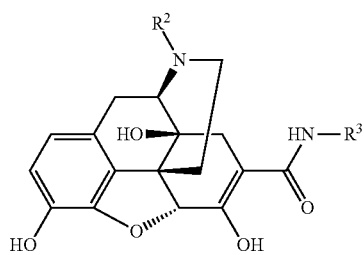
(I)

wherein $R^2$ and $R^3$ are the same as defined in (31);
characterized by treating with a base a compound of the formula (IIC):

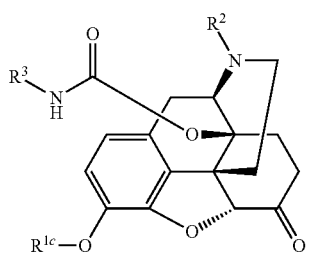
(IIC)

wherein $R^{1c}$ is a hydroxy-protecting group deprotectable by a base, and $R^2$ and $R^3$ are the same as defined above.

(41) A process for preparing a compound of the formula (IB):

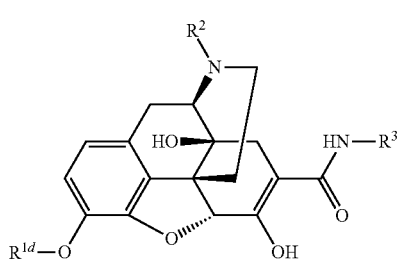
(IB)

wherein $R^{1d}$ is hydrogen or a hydroxy-protecting group not deprotectable by a base, $R^2$ and $R^3$ are the same as defined in (31);

characterized by treating with a base a compound of the formula (IIB):

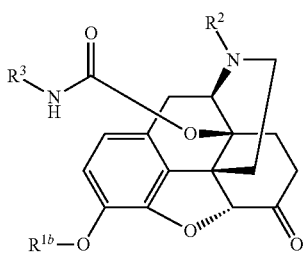
(IIB)

wherein $R^{1b}$ is a hydroxy-protecting group; $R^2$ and $R^3$ are the same as defined above.

(42) The process according to any one of (39) to (41), wherein the base is an inorganic base.

(43) The process according to any one of (39) to (41), wherein the base is potassium hydroxide, sodium hydroxide, lithium hydroxide, or cesium hydroxide.

(44) The process according to any one of (39) to (43), wherein the reaction temperature is 30°C-100° C.

(45) A process for preparing a compound of the formula (IX):

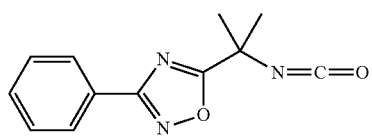
(IX)

by reacting a compound of the formula (VIIIa):

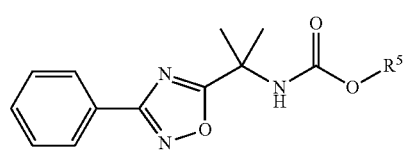
(VIIIa)

wherein $R^5$ is a lower alkyl; in the presence of a Lewis acid and a base.

(46) The process according to (45), characterized by reacting a compound of the formula (X):

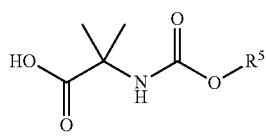
(X)

wherein $R^5$ is a lower alkyl; with a compound of the formula (XI):

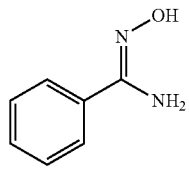

(XI)

to afford said compound of the formula (VIIIa).

(47) The process according to (45) or (46), wherein the Lewis acid is AlCl$_3$ or TiCl$_4$.

(48) A process for preparing an acid addition salt of a compound of the formula (I), comprising the steps of:

reacting a compound of the formula (IIIA):

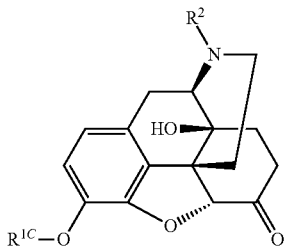

(IIIA)

wherein R$^{1c}$ is a hydroxy-protecting group deprotectable by a base and R$^2$ is the same as defined in (31);

with a compound of the formula: R$^3$—N=C=O, wherein R$^3$ is the same as defined in (31); or with a compound of the formula: R$^3$—NH—C(=O)—X, wherein R$^3$ is the same as defined above, and X is a leaving group;

in the presence or absence of a Lewis acid catalyst to obtain a compound of the formula (IIC):

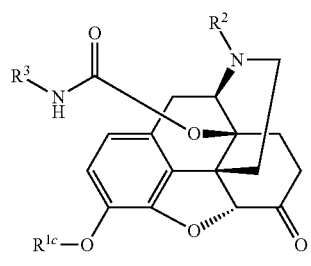

(IIC)

wherein R$^{1c}$, R$^2$ and R$^3$ are the same as defined above; then, treating the compound of the formula (IIC) with a base to obtain a compound of the formula (I):

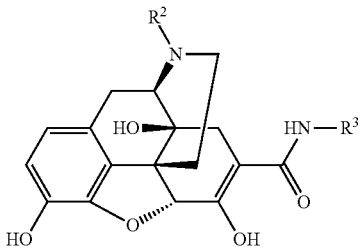

(I)

wherein R$^2$ and R$^3$ are the same as defined above; and adding an acid to the compound of the formula (I) to form the acid addition salt.

The acid addition salt is also obtained by cooling the reaction solution after the acid addition salt is formed by addition of an acid.

Wherein the embodiments of the present invention are further exemplified in preparing the compound of the formula (IIC) comprising a step of:

reacting a compound of the formula (IIIA) with a compound of the formula: R$^3$—N=C=O wherein R$^3$ is the same as defined above in the presence of a Lewis acid catalyst;

reacting a compound of the formula (IIIA) with a compound of the formula: R$^3$—N=C=O wherein R$^3$ is the same as defined above in the absence of a Lewis acid catalyst; or reacting a compound of the formula (IIIA) with a compound of the formula: R$^3$—NH—C(=O)—X wherein R$^3$ and X are the same as defined above in the absence of a Lewis acid catalyst.

(49) The process according to (48), wherein the acid addition salt of the compound of the formula (I) is a p-toluenesulfonic acid salt, an acetic acid salt, a hydrochloric acid salt, or a solvate thereof.

(50) The process according to (49), wherein the p-toluenesulfonic acid salt, the acetic acid salt, or the hydrochloric acid salt, or the solvate thereof is crystal.

(51) A compound of the formula (IID):

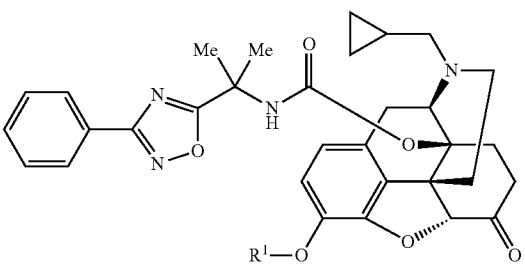

(IID)

wherein R$^1$ is hydrogen or a hydroxyl-protecting group.

(52) A compound of the formula (VII):

(VII)

wherein $R^6$ is a group represented by —N=C=O or —NH—C(=O)—X, wherein X is a leaving group.

In the compounds shown by the above-mentioned formula (II), formula (IIA), formula (IIB), formula (IIC), formula (IID) and formula (IIE), the hydrogen of "—NH—" of the "—O—C(=O)—NH—" group attached to a side chain of 7-position in the morphinan skeleton may be replaced by an amino-protecting group.

In the present Description, "halogen" includes fluorine, chlorine, bromine and iodine. The halogen moiety of "halogeno lower alkyl", "halogeno lower alkoxy", and "halogeno lower alkylthio" is also the same.

"Lower alkyl" includes straight or branched alkyl of carbon numbers 1-10, preferably 1-6, or more preferably 1-3, and for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl are exemplified. Methyl, ethyl, isopropyl, n-butyl, sec-butyl, tert-butyl, and 1-ethylpropyl, etc. are preferable.

As a substituent of "optionally substituted lower alkyl", halogen, hydroxy, lower alkoxy, halogeno lower alkoxy, hydroxy lower alkoxy, lower alkylthio, lower alkylamino, acylamino, acyl, acyloxy, cyano, carboxy, lower alkoxy carbonyl, carbamoyl, lower alkyl carbamoyl, cyano carbamoyl, lower alkyl sulfonylcarbamoyl, aryl sulfonylcarbamoyl, sulfamoyl, lower alkyl sulfamoyl, lower alkyl sulfonyl, cycloalkyl optionally substituted with one or more groups selected from a substituent group α (the substituent group α means halogen, hydroxyl, lower alkyl, halogeno lower alkyl, hydroxy lower alkyl, lower alkoxy lower alkyl, carboxy lower alkyl, lower alkoxy carbonyl lower alkyl, amino lower alkyl, lower alkylamino lower alkyl, acylamino lower alkyl, cyano lower alkyl, lower alkoxy, halogeno lower alkoxy, hydroxy lower alkoxy, lower alkylthio, halogeno lower alkylthio, acyl, acyloxy, amino, lower alkylamino, acylamino, cyano, carboxy, lower alkoxy carbonyl, carbamoyl, lower alkyl carbamoyl, aryl carbamoyl, cyano carbamoyl, lower alkyl sulfonylcarbamoyl, sulfamoyl, lower alkyl sulfamoyl, lower alkyl sulfonyl, aryl and heterocyclic group optionally substituted with lower alkylene dioxy), cycloalkenyl optionally substituted with one or more groups selected from the substituent group α, aryl optionally substituted by one or more groups selected from the substituent group α, aryloxy optionally substituted with one or more groups selected from the substituent group α, arylthio optionally substituted with one or more groups chosen from the substituent group α, a heterocyclic group optionally substituted with one or more groups selected from the substituent group α, and heterocycle oxy optionally substituted with the one or more groups chosen from the substituent group α are exemplified.

The lower alkyl moiety of "halogeno lower alkyl", "hydroxy lower alkyl", "amino lower alkyl", "acylamino lower alkyl", "acyloxy lower alkyl", "cycloalkyl lower alkyl", "lower alkoxy one", "halogeno lower alkoxy one", "hydroxy lower alkoxy", "lower alkoxy lower alkyl", "lower alkoxy carbonyl", "carboxy lower alkyl", "lower alkoxy carbonyl lower alkyl", "lower alkylthio", "halogeno lower alkylthio", "lower alkylamino", "lower alkylamino lower alkyl", "lower alkyl carbamoyl", "lower alkyl sulfamoyl", "lower alkyl sulfonyl", "aryl lower alkyl", "tri lower alkyl silyl", "lower alkyl diaryl silyl", "triaryl lower alkyl silyl", "lower alkoxy lower alkoxy lower alkyl", "lower alkylthio lower alkyl", "aryl lower alkoxy lower alkyl", "lower alkyl sulfonyl", "lower alkyl sulfonylcarbamoyl", "lower alkyl carbonyl", "cyano lower alkyl", "lower alkoxylcarbonylamino", "lower alkylene dioxy" and "heterocycle lower alkyl" is the same as that of the above "lower alkyl."

A substituent of "optionally substituted lower alkoxy", "optionally substituted lower alkylthio" and "optionally substituted lower alkyl sulfonyl" is the same as the substituent of the above "lower alkyl optionally substituted."

"Lower alkenyl" includes straight or branched alkenyl of carbon numbers 2-10, preferably 2-8, more preferably 3-6 which has one or more double bonds in arbitrary positions. Specifically, vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl, etc. are included.

A substituent of "optionally substituted lower alkenyl" is the same as those of "optionally substituted lower alkyl".

"Lower alkynyl" includes straight or branched alkynyl of carbon numbers 2-10, preferably 2-8, more preferably 3-6 which has one or more triple bonds in arbitrary positions. Specifically, ethynyl, propynyl, butynyl, pentynyl, hexynyl, heptynyl, octynyl, nonynyl, decynyl, etc. are included. These may have a double bond in still more arbitrary positions.

A substituent of "optionally substituted lower alkynyl" is the same as that of the "optionally substituted lower alkyl" above.

As a substituent of "optionally substituted amino", a lower alkyl optionally substituted with one or more groups selected from substituent group α, a cycloalkyl optionally substituted by one or more groups selected from substituent group α, an acyl optionally substituted with one or more groups selected from substituent group α, amino optionally substituted with one or more groups selected from substituent group α, aryl optionally substituted with one or more groups selected from the substituent group α, a sulfamoyl, a lower alkyl sulfamoyl optionally substituted with one or more groups selected from substituent group α, aryl sulfamoyl optionally substituted with one or more groups selected from substituent group α, lower alkyl sulfonyl optionally substituted with one or more groups selected from substituent group α, arysulfonyl optionally substituted with one or more groups selected from the substituent group α, arylamino optionally substituted with one or more groups selected from the substituent group α, and a heterocyclic group optionally substituted by the one or more groups selected from the substituent group α are exemplified.

A substituent of "optionally substituted carbamoyl" is the same as that of the above "optionally substituted amino".

"Cycloalkyl" is a carbocyclic group of carbon numbers 3-10, preferably 3-8, more preferably 4-8, and includes, for example, cyclopropyl, cyclobutyl, cyclopentyl, cyclohexyl, cycloheptyl, cyclooctyl, cyclononyl, cyclodecyl, etc. These may be further fused with the below-mentioned "aryl" or "heterocyclic group" in any positions.

A cycloalkyl moiety of "cycloalkyl lower alkyl" and "cycloalkyl carbonyl" is the same as that of the above "cycloalkyl".

One or more groups selected from the substituent group α described above are exemplified as a substituent of "optionally substituted cycloalkyl". Substituents can substitute at any positions and may substitute at a carbon atom having a cycloalkyl bond.

The term "cycloalkenyl" includes the above-mentioned cycloalkyl having one or more double bonds in any positions in the ring, and specifically includes cyclopropenyl, cyclobutenyl, cyclopentenyl, cyclohexenyl, cycloheptenyl, cyclooctenyl, cyclohexadienyl, etc.

The cycloalkenyl moiety of "cycloalkenyl carbonyl" is the same as that of the above "cycloalkenyl".

A substituent of "optionally substituted cycloalkenyl" is the same as that of the above "cycloalkyl optionally substituted".

"Aryl" includes phenyl, naphthyl, anthryl, phenanthryl, and especially preferably, phenyl.

Aryl moieties of "aryloxy", "arylthio", "aryl lower alkyl", "lower alkyl diaryl silyl", "triaryl lower alkyl silyl", "aryl lower alkyloxy lower alkyl", "aryl sulfonyl", "aryl sulfamoyl", "arylamino", "aryl carbamoyl" and "aryl sulfonylcarbamoyl" are the same as that of the above "aryl".

As substituents of "optionally substituted aryl", "optionally substituted phenyl" and "optionally substituted aryl sulfonyl", substituents of the substituent group α above, phenyl substituted with one or more groups selected from the substituent group α, phenoxy substituted with one or more groups selected from the substituent group α, or a lower alkylene dioxy etc. are exemplified.

A "heterocyclic group" includes heterocyclic groups having one or more of hetero atom(s) optionally selected from O, S and N in the ring, and specifically includes heteroaryls of 5-6 members such as pyrrolyl, imidazolyl, pyrazolyl, pyridyl, pyridazinyl, pyrimidinyl, pyrazinyl, triazoryl, triadinyl, tetrazolyl, isoxazolyl, oxazolyl, oxadiazolyl, isothiazolyl, thiazolyl, thiadiazolyl, furyl and thienyl etc.;

a bicyclic fused-heterocyclic group such as indolyl, isoindolyl, indazolyl, indridinyl, indrinyl, isoindrinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazoryl, imidazopyridyl, triazolopyridyl, imidazothiazolyl, pyrazinopyridazinyl, quinazolinyl, quinolyl, isoquinolyl, naphthyridinyl, dihydropyridyl, tetrahydroquinolyl and tetrahydrobenzothienyl;

tricyclic condensed-heterocyclic groups such as carbazolyl, acridinyl, xanthenyl, phenothiazinyl, phenoxathiinyl, phenoxazinyl, dibenzofuryl;

a non-aromatic heterocyclic group such as dioxanyl, thiiranyl, thiolanyl, thiethanyl, oxilanyl, oxetanyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrofuryl, tetrahydrofuryl, tetrahydropyranyl, tetrahydrothiazolyl, and tetrahydroisothiazolyl are included.

Heteroaryl or non-aromatic heterocyclic groups of 5-6 members are preferable.

The heterocyclic moiety of "heterocyclic oxy" and "heterocyclic lower alkyl" is the same as that of the above "heterocyclic group".

One or more groups selected from the group consisting of the above-mentioned substituent group α and oxo are exemplified as the substituent of "optionally substituted heterocyclic group" and "optionally substituted heterocycle oxy". Substituents can substitute at any positions and may substitute at carbon atom or nitrogen atom having a bond of a heterocyclic group.

"Acyl" includes straight or branched linear aliphatic acy of carbon numbers 1-10, preferably 1-6, more preferably 1-4, and cyclic aliphatic acyl, aroyl and heterocyclic carbonyl of carbon numbers 4-9, preferably 4-7.

"Linear aliphatic" includes "lower alkyl" above, "lower alkenyl" above, and "lower alkynyl" above. "Cyclic aliphatic" includes "cycloalkyl" above and "cycloalkenyl" above. The heterocycle moiety of heterocycle carbonyl is the same as that of the above "heterocyclic group". An example of acyl, formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, pyridinecarbonyl, piperidinecarbonyl, piperazinecarbonyl, morpholinocarbonyl, etc. are included.

The acyl moieties of "acyloxy", "acylamino", "acylamino lower alkyl", and "acyloxy lower alkyl" are the same as that of the above "acyl."

The substituent of "optionally substituted acyl" or "optionally substituted acyloxy" is the same as the substituent of the above "optionally substituted lower alkyl" when "acyl" is a linear aliphatic acyl, and when "acyl" is a cyclic aliphatic acyl, aroyl, and heterocycle carbonyl, the substituent is one or more groups selected from the substituent group α above.

A "solvate" includes a solvate with organic solvents (ethanol, 2-propanol, methyl acetate, ethyl acetate, n-propyl acetate, 1,2-dimethoxyethane, methyl isobutyl ketone, acetonitrile, etc.) and a hydrate, for example. When forming a hydrate, the hydrate may be coordinated with any numbers of water molecules.

As a "hydroxyl-protecting group", benzyl, p-methoxyphenybenzyl, acetyl, formyl, benzoyl, chloroacetyl, pivaloyl, methyl carbonate, isobutyl carbonate, benzyl carbonate, vinyl carbonate, phenyl carbamate, mesyl, tosyl, trimethylsilyl, triethyl silyl, t-butyldimethylsilyl, methoxymethyl, benzyloxymethyl, methoxyethoxymethyl, 2-(trimethylsilyl)ethoxymethyl, propenyl, phenacyl and tetrahydropyranyl etc. are exemplified.

As a "hydroxyl-protecting group deprotectable by a base", acetyl, formyl, benzoyl, chloroacetyl, pivaloyl, methyl carbonate, isobutyl carbonate, benzyl carbonate, vinyl carbonate, phenyl carbamate, mesyl, tosyl etc. are exemplified. In one aspect, acetyl, formyl, benzoyl, chloroacetyl and pivaloyl are exemplified. Acetyl is exemplified in another aspect.

As a "hydroxyl-protecting group un-deprotectable by a base", benzyl, p-methoxyphenybenzyl, trimethylsilyl, triethylsilyl, t-butyldimethylsilyl, methoxymethyl, benzyloxymethyl, methoxyethoxymethyl, 2-(trimethylsilyl)ethoxymethyl, propenyl, phenacyl and tetrahydropyranyl etc. are exemplified.

As a "leaving group", optionally substituted phenoxy (for example, phenoxy, p-nitrophenoxy and o-nitrophenoxy are exemplified), a heterocyclic group (for example, 1-imidazolyl and 1-pyrazolyl are exemplified), optionally substituted heterocycle oxy (for example, pyridyloxy is exemplified) etc. are exemplified.

As an "acid addition salt of a compound of the formula (I)" and an "acid addition salt of a compound of the formula (IA)", a salt with an inorganic acid (for example, hydrochloric acid, sulfuric acid, nitric acid, carbonic acid, hydrobromic acid, phosphoric acid, hydroiodic acid, etc.), or an organic acid (for example, formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethane sulfonic acid, etc.) is exemplified. For example, as the acid addition salt of "an acid addition salt of a compound of the formula (I)", and the acid addition salt of "an acid addition salt of a compound of the formula (IA)", a p-toluenesulfonic acid salt, an acetic acid salt, and a hydrochloric acid salt are exemplified.

As an "amino-protecting group", t-butyldimethylsilyl, t-butoxycarbonyl, allyl, 9-fluorenylmethyloxycarbonyl, benzyl, p-methoxybenzyl, methoxymethyl, benzyloxymethyl, benzhydryl, and trityl are exemplified.

Effect of Invention

The present invention provides a 6,7-unsaturated-7-carbamoyl morphinan derivative, an acid addition salt thereof and/or crystal of a solvate thereof. Said crystal has good stability and can be used as an ingredient for manufacturing pharmaceuticals. The novel manufacturing process can contribute to shortening of manufacturing steps, improvement of yields etc.

MODE FOR CARRYING OUT THE INVENTION

Figure 1:
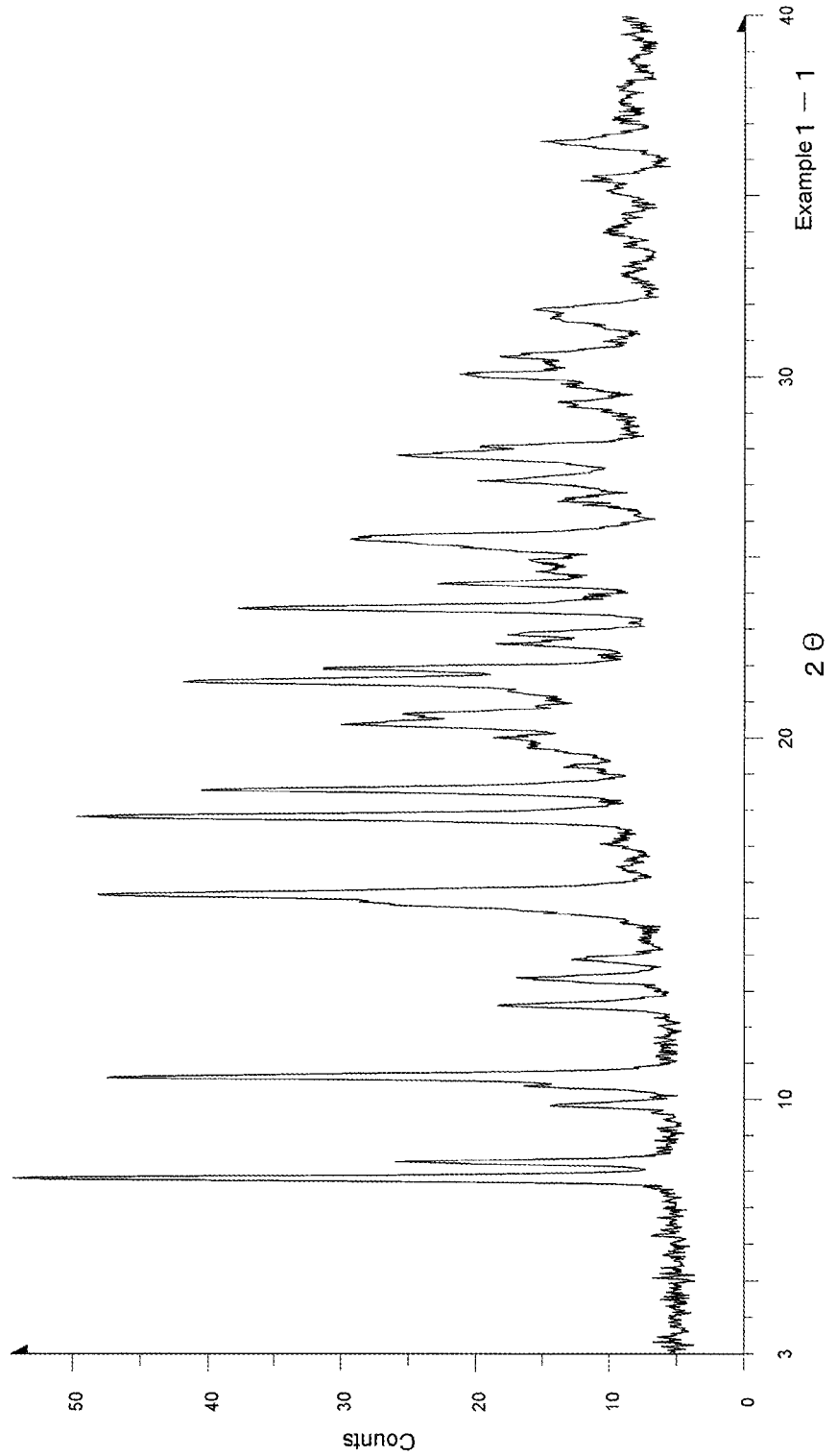
FIG. 1 shows an X-ray-powder-diffraction pattern of the crystal (non-solvate) of a p-toluenesulfonic acid salt of the compound (IA) in the present invention.

The crystal of the present invention is obtained as an acid addition salt of the compound shown by the formula (I), or a solvate of said acid addition slat. As an acid used herein, p-toluenesulfonic acid, acetic acid, or hydrochloric acid is exemplified. Especially, the crystal of p-toluenesulfonic acid is considered not to be hygroscopic, and to have an excellent stability. As a solvent for forming a solvate, water, ethanol, 2-propanol, methyl acetate, ethyl acetate, n propyl acetate, 1, 2-dimethoxyethane, methyl isobutyl ketone, acetonitrile, etc. can be exemplified.

The crystal of an acid addition salt is crystallized after addition of 1.0-10.0 equivalents of acid into a solution of the compound of the formula (I) at 0° C. to room temperature or by warming at a temperature below a boiling point of the solvent, optionally by cooling or condensing the solvent.

The preparation of the solvated crystal is carried out by dissolving the acid addition salt of the compound of the formula (I) into a solubilizing solvent containing the solvent to be solvated at least at room temperature or below boiling point of the solvent by warming, adding a solvent to be solvated, and stirring or letting still stand the solution at 0° C. to a room temperature for few hours to one day. It can be collected from a solvent by the ordinary separating mechanisms, such as filtration or centrifugal separation, and isolated by the ordinary refining means, such as washing and drying.

A solvate of the compound shown by formula (I) is also included in the crystal of the present invention. Water, ethanol, etc. are exemplified as a solvent. The solvate of the compound shown by formula (I) can be prepared in the same manner as the solvate of the above-mentioned acid addition salt.

In the case of a compound (IA), a p-toluenesulfonic acid salt (non-solvate), a hydrate of p-toluenesulfonic acid salt, a methyl acetate solvate of p-toluenesulfonic acid salt, an ethyl acetate/2-propanol solvate of p-toluenesulfonic acid salt, a n-propyl acetate/2-propanol solvate of p-toluenesulfonic acid salt, an acetonitrile solvate of p-toluenesulfonic acid salt, a 1, 2-dimethoxyethane solvate of p-toluenesulfonic acid salt, a methyl-isobutyl-ketone solvate of p-toluenesulfonic acid salt, a hydrochloride, acetate, an ethanol solvate of free form etc. can be exemplified as an example of the crystal of the present invention.

For example, the p-toluenesulfonic acid salt (non-solvate) of the compound shown by a formula (IA) is obtained as follows: 2-propanol and n-propyl acetate are added to the organic layer containing a compound (IA) and the solution is concentrated. A 2-propanol solution containing 1-10.0 equivalent of p-toluenesulfonic acid is added dropwise thereto at 50-70° C. and crystallization is carried out. The obtained crude solid is dissolved in methanol and n-propyl acetate again by warming, insoluble materials is filtered off, and crystallization is carried out by concentrating the filtrate in vacuo. The resulting crystal is dried at 50-70° C. for 2-5 hours in vacuo to give the target p-toluenesulfonic acid salt (non-solvate).

Specifying methods of the crystal of the present invention are illustrated below.

If there is no reference in particular, the numerical value of the description and claims is a near value. A numerical change originates in a device calibration, a device error, the purity of a substance, a crystal size, a sample size, and the other factors.

The "crystal" used in this description means the substance having the molecular structure of the orderly long range. The crystallinity of crystal can be measured by multiple techniques including X-ray powder diffraction, water adsorption, differential or calorimetric analysis, solution chromoscopy, and dissolution property, for example.

In general, a crystalline organic compound consists of a large number of atoms arranged periodically in three-dimensional space. Structural period nature usually provides a physical property which is distinguishable according to most spectrophotometrical probes (for example, an X-ray diffraction, an infrared spectrum, a Raman spectrum, and solid NMR).

Among them, X-ray powder diffraction (XRPD) is one of the most highly sensitive analytical methods for measuring solid crystallinity.

When crystal is irradiated with X-rays, it is reflected on a crystal lattice, interfered mutually and only a diffraction line of a direction which fulfills the conditions predicted by Bragg's rule is intensified. Other diffraction line is not observed.

On the other hand, a well-ordered diffraction line over wide range is not observed as to an amorphous solid. Usually an order of wide range based on a repeated crystal lattice is absent in an amorphous solid, and broad XRPD pattern called a halo pattern is observed.

The crystalline form of the 6,7-unsaturated-7-carbamoyl morphinan derivative, its acid addition salt, and/or those solvates disclosed in this application, has a distinguishable X-ray-power-diffraction profile preferably.

In the case of the p-toluenesulfonic acid salt of a compound (IA), it is possible to specify each crystal by existence of a characteristic diffraction peak preferably and distinguish the crystal from other crystal. The characteristic diffraction peak used in this description is a peak chosen from the observed diffraction pattern. Preferably, the characteristic peak can be selected from about 20 peaks, more preferably about ten peaks, most preferably about five peaks in the diffraction pattern.

It is necessary to understand that the value of diffraction angle (2θ) contains an error of ca. ±0.2°, since an error may arise in general within the limits of ±0.2° in diffraction angle of XRPD. Therefore, not only crystal having an identical value of diffraction angle in XRPD but also crystal having a value contained in the range of ±0.2° is included in the present invention.

It is generally known that the relative intensity of the peak displayed in table and figure below may be changed by effects of many factors such as, for example, the orientation effect of the crystal toward an X-ray beam, the purity of the substance analyzed, or the crystallinity of a sample. Also a peak position can be shifted based on change of sample height. Further, a different shift may be obtained according to Bragg equation (n λ=2d sin θ), when a sample is measured by using different wavelength, but another XRPD pattern obtained by use of such another wavelength is also contained in the range of the present invention.

Figure 2:
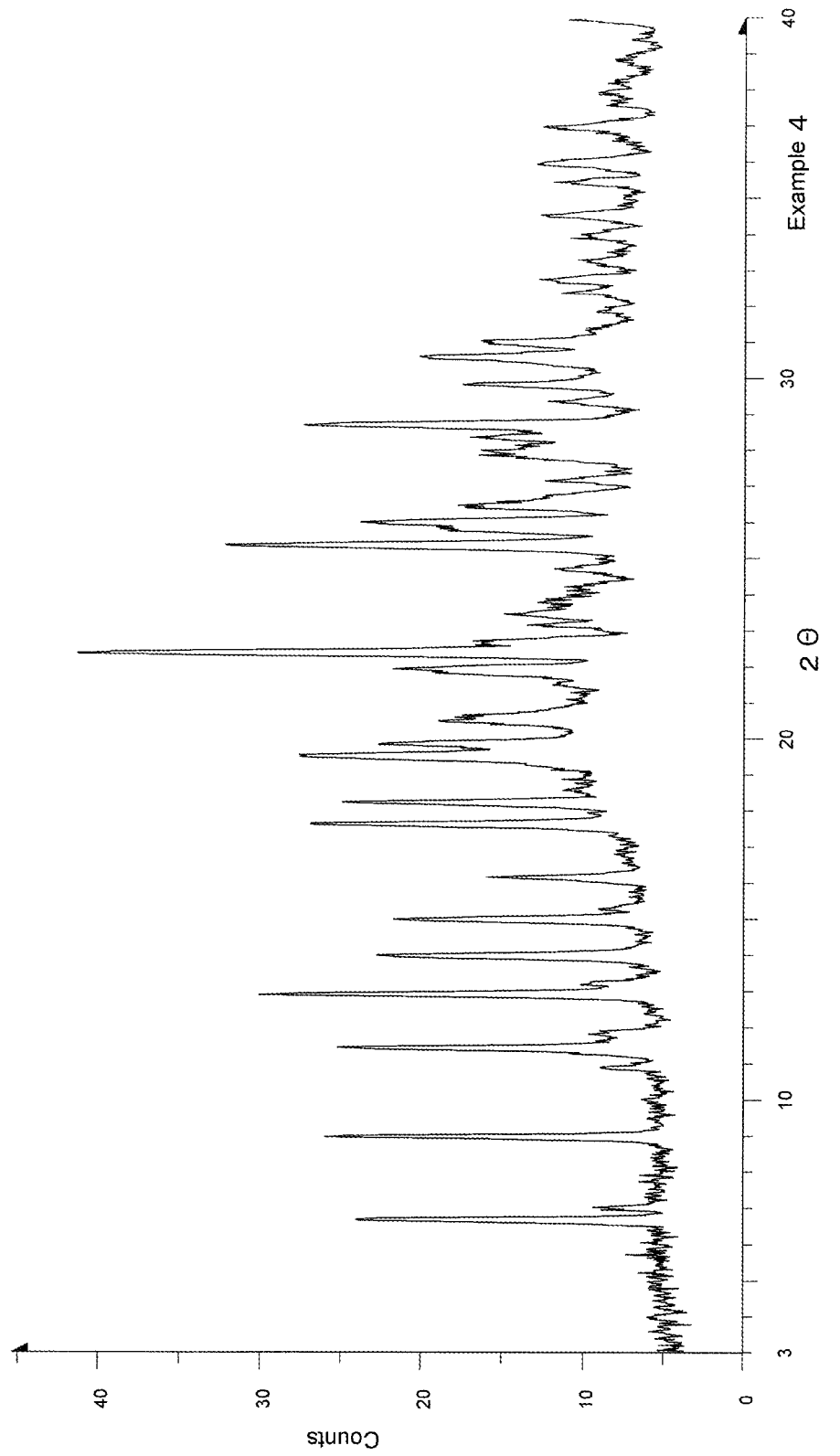
FIG. 2 shows an X-ray-powder-diffraction pattern of the crystal (form I) of a p-toluenesulfonic acid salt hydrate of the compound (IA) in the present invention.
Figure 3:
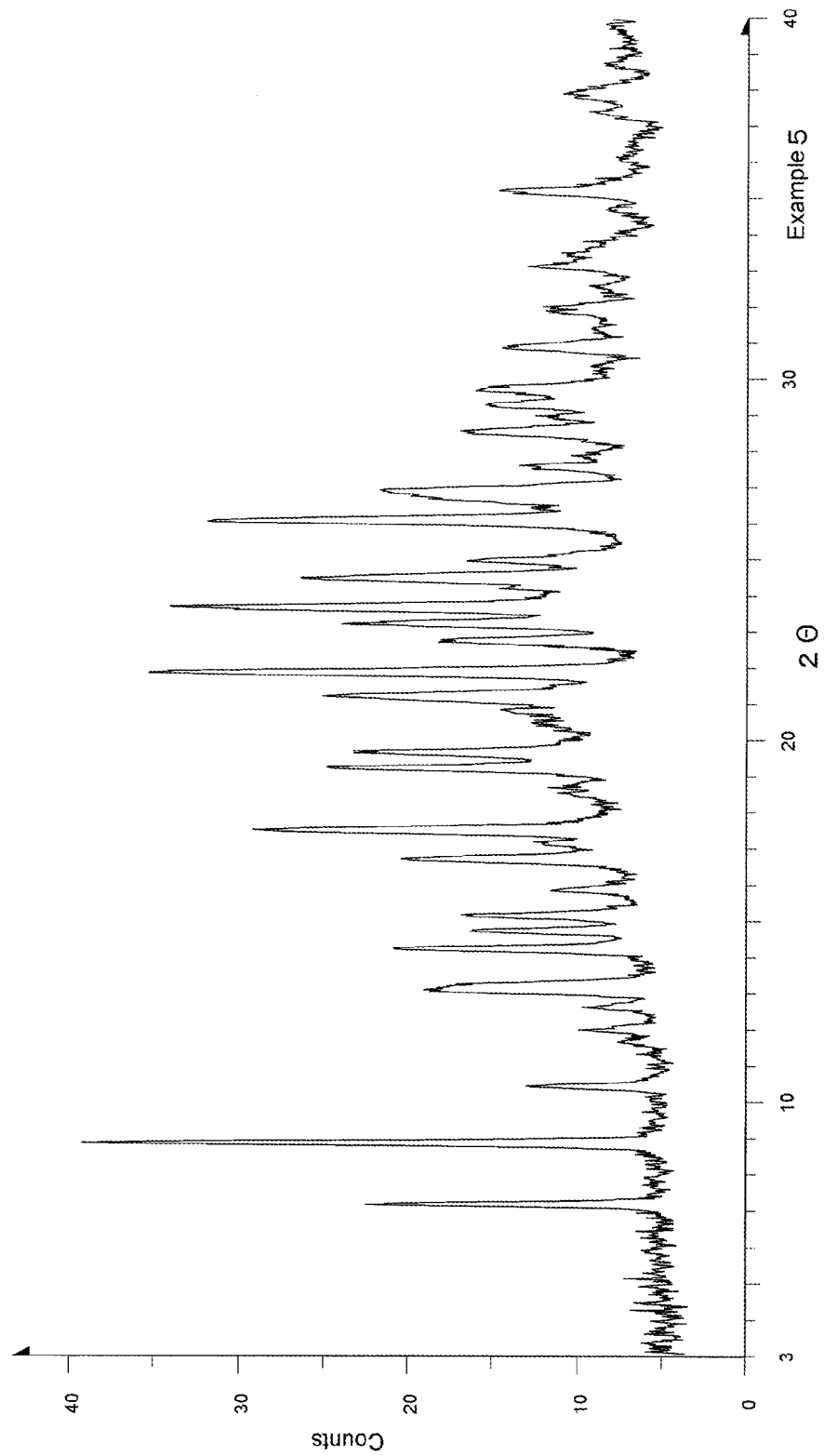
FIG. 3 shows an X-ray-powder-diffraction pattern of the crystal (form II) of a p-toluenesulfonic acid salt hydrate of the compound (IA) in the present invention.

The crystal of p-toluenesulfonic acid salt (non-solvate), p-toluenesulfonic acid salt hydrate (form I), and p-toluenesulfonic acid salt hydrate (form II) of the compound (IA) in the present invention show an X-ray-power-diffraction pattern as shown in FIGS. 1-3. Each crystal shows a characteristic peak as shown in Table 1 at least.

TABLE 1

| Diffraction angles (2θ) | | | | |
|---|---|---|---|---|
| p-Toluenesulfonic acid salt | | | | |
| (non-solvate) | hydrate (Form I) | hydrate (Form II) | Acetic acid salt | Hydrochloric acid salt |
| 7.8° ± 0.2° | 12.9° ± 0.2° | 8.8° ± 0.2° | 5.6° ± 0.2° | 8.5° ± 0.2° |
| 10.6° ± 0.2° | 17.6° ± 0.2° | 17.5° ± 0.2° | 10.3° ± 0.2° | 12.7° ± 0.2° |
| 15.6° ± 0.2° | 22.4° ± 0.2° | 21.9° ± 0.2° | 12.0° ± 0.2° | 15.6° ± 0.2° |
| 17.8° ± 0.2° | 25.4° ± 0.2° | 23.7° ± 0.2° | 14.6° ± 0.2° | 17.3° ± 0.2° |
| 21.5° ± 0.2° | 28.7° ± 0.2° | 26.1° ± 0.2° | 26.0° ± 0.2° | 23.9° ± 0.2° |

The crystal of the present invention can also be specified by the procedure of a thermal analysis.

TG/DTA (Thermogravimetric/Differential Thermal Analysis) is one of the major measuring methods of a thermal analysis, and is the method of measuring the weight and the thermal property of a substance as an aggregate of an atom and a molecule.

TG/DTA is the method of measuring change of the weight and the quantity of heat concerning the temperature or time of an active pharmaceutical ingredient, and TG (thermo gravity) and a DTA (Differential Thermal Analysis) curve are obtained by plotting the obtained data to temperature or time. From TG/DTA curve, the information on the weight about decomposition of an active pharmaceutical ingredient, dehydration, oxidation, reduction, sublimation, and evaporation and quantity-of-heat change can be acquired.

In TG/DTA, a "melting point" means onset temperature.

It is known that the temperature and the weight change observed can be dependent on heating rate, the sample preparation technique to be used, and a specific device about TG/DTA. In authorization of the identity of crystal, an overall pattern is important and may change with measurement conditions to some degree.

As to the crystal of the p-toluenesulfonic acid salt, a p-toluenesulfonic acid salt hydrate (form I), a p-toluenesulfonic acid salt hydrate (form II), an acetate and a hydrochloride, results of the TG/DTA analysis are shown in FIGS. 14-18.

The crystal of the compound of the formula (IA), its acid addition salt, and/or those solvates has an opioid receptor (especially opioid δ and μ receptors) antagonistic activity. Accordingly it is effective on treating and/or preventing nausea, emesis, constipation as well as acute digestive trouble, acute alcoholism, food poisoning, cold, gastric ulcer, duodenal ulcer, stomach cancer, ileus, appendicitis, peritonitis, cholelithiasis, hepatitis, liver flame, encephalitis, meningitis, brain hypertension, head injury, motion sickness, a vomiting of pregnancy, side effect of chemotherapy, side effect of radiation therapy, side effect of an anticancer agent, hindrance of gastrointestinal transit caused by pressure or a stenosis of gastrointestine or postoperative intestinal adhesions, nausea or emesis resulted from brain pressure elevation by brain tumor, brain bleeding, meningitis, the radiation irradiation to a brain tumor, acute constipation caused by ileus, a duodenal ulcer or appendicitis etc., neuropathy, undernutrition, prostration, avitaminosis, ischemia, atonic constipation caused by hyposensitivity or shortage of mechanical stimulus, spastic constipation caused by stress etc., which are induced by a compound having an opioid receptor agonistic activity.

The crystal of the compound shown by the formula (IA), its acid addition salt, and/or those solvates in the present invention has a poor transitivity into the brain, and has an excellent effect on reducing side effects such as nausea, emesis and constipation etc. induced by an opioid receptor agonist without inhibiting an analgesic effect of the agonist, which are administrated to a patient of a disease associated with a pain such as a cancer pain (bone metastasis; nerve compression; increased intracranial pressure; soft tissue permeation; constipation or pain by muscle spasm; pain of viscera, the muscle and the fascia, the waist, or the circumference of the shoulder joint; a postoperative chronic pain) and AIDS etc.

Also the crystal of the present invention has a pure antagonist activity to an opioid receptor, its inhibitory action on hERG channel is weak, and there is no concern of cardiac toxicity. These are advantage in the aspect of safety. Further, the crystal of the present invention has the advantageous feature in disposition such as excellent oral absorbability, high stability in human plasma and high bioavailability, and is very effective as a drug.

When prescribing crystal of the present invention or its pharmaceutical composition for a patient of nausea, emesis, and constipation which are induced by a compound having an opioid receptor agonistic activity, it may be administered before the administration of the compound having an opioid receptor agonistic activity, after the administration, or simultaneously with the administration. The intervals of administration of these two sorts of drugs are not limited in particular.

For example, when a pharmaceutical composition comprising the crystal of the present invention is administered after the administration of the compound having an opioid receptor agonistic activity, it will be effective if the composition is administered immediately after or within less than about 3 days after the administration of the opioid receptor agonist, or immediately after or within less than one day after the administration. When the composition is administered before the administration of the opioid receptor agonist, it will be effective if the composition is administered immediately before or within less than about one day before the administration of the opioid receptor agonist, or immediately before or within less than about 12 hours before the administration.

When prescribing a pharmaceutical composition comprising the crystal of the present invention or its crystal for treating and/or preventing nausea, emesis, or constipation, other agent for treating and/or preventing nausea, emesis, or constipation may be used in combination. For example, a combination with other agent such as ondansetron hydrochloride, adrenocorticosteroid (methylprednisolone, prednisolone, dexamethasone etc.), prochlorperazine, haloperidol, Timiperone, perphenazine, metoclopramide, domperidone, scopolamine, chlorpromazine hydrochloride, droperidol, stimulative laxatives (sennoside, sodium picosulfate, etc.), an osmotic laxative (lactulose), salts laxatives (magnesium oxide etc.) etc. is possible.

Also a compound having an opioid receptor agonistic activity, and/or other agent for treating and/or preventing nausea, emesis, or constipation, and also other pharmaceutical additives may be added, if necessary, to the crystal or the pharmaceutical composition comprising the crystal of the present invention to prepare a combined agent.

The crystal of the present invention can be administered to a patient directly or a pharmaceutical composition in which the crystal of the present invention is blended with a pharmaceutical carrier or excipient can also be administered. The technical information for the formulation and administration of the drug can be found out to "Remington's Pharmacological Sciences" Mack Publishing Co., Easton, and PA. the latest version.

Although a suitable route for administration is not limited, it is possible to include oral, intrarectal, transmucosa, enteral, intramuscular, subcutaneous, intraspinal, intrathecal, direct intraventricular, intravenous, intraperitoneal, intranasal, intraocular administration, and injection. Oral and parenteral administration is preferable.

The pharmaceutical composition of the present invention can be prepared by a method well known in the technical field such as a conventional mixing, dissolution, granulation, sugar-coating, powderization, emulsifying, encapsulation, packaging and lyophilization processes.

The pharmaceutical composition used in the present invention can be formulated by a known method using one or more of pharmaceutically acceptable carrier including an excipient and an additive which make easy to prepare pharmaceutically allowable formulation comprising the crystal of the present invention. A suitable formulation depends on a selected route of administration.

When administering by injection, the crystal of the present invention can be administered after dissolving it in an aqueous solution, preferably, in Ringer's solution or a buffer solution such as physiological saline, which are physiologically acceptable. In a case of transmucosal administration, it can be achieved by using a penetrating agent suitable for the target barrier. The penetrating agent conventionally used in the technical field can be used.

When administering orally, the crystal of the present invention can be administered in combination with a pharmaceutically acceptable carrier which is well known in the technical field. For the oral intake of a patient, the administration can be achieved in a formulation such as tablet, pill, lozenge, sugar-coated tablet, capsule, liquid, gel, syrup, slurry, and suspension. The pharmaceutical composition for an oral use can be prepared by blending a solid excipient and other suitable additive, if necessary, granulating the mixture and treating the resulting granule to obtain a tablet or core for sugar-coating.

An example of the excipient includes a bulking agent of a sugar such as lactose, sucrose, mannitol, or sorbitol; specifically cellulose preparation such as corn starch, wheat starch, rice starch, and potato starch; and tragacanth gum, methyl cellulose, hydroxypropylmethylcellulose and/or carboxymethylcellulose sodium etc.

When necessary, a disintegrant such as agar and alginic acid can be added therein. A salt such as sodium alginate can also be used.

The pharmaceutical composition of an oral use contains a push fit capsule made of gelatin and a sealed capsule formulated with plasticizers such as gelatin, glycerol, or sorbitol. The push fit capsule can contain the crystal of the present invention with a bulking agent such as lactose, a binder such as starch, a lubricant such as talc or magnesium stearate, and an stabilizing agent, if necessary. In a case of a soft capsule, the crystal of the present invention may be dissolved or suspended in a suitable fluid such as fatty oil, liquid paraffin, or liquid polyethylene glycol. A stabilizing agent can also be added to the formulation.

The pharmaceutical composition can also contain a suitable carrier or an excipient of a solid phase or a liquid phase. An example of the carrier or an excipient includes calcium carbonate, calcium phosphate, various kinds of sugar, starch, a cellulose derivative, gelatin, and a polymer such as polyethylene glycol etc.

An effective amount of the crystal or the pharmaceutical composition comprising the crystal of the present invention for the treatment can be estimated from a cell culture assay at first. Subsequently, an administration amount may be increased for an animal experiment so that a range of concentration for circulation containing $IC_{50}$ value (namely, the concentration of the crystal or the pharmaceutical composition thereof to achieve a half of the maximum inhibition of PK activity) determined in the cell culture assay. Subsequently, an effective amount for human can be more correctly determined using such information.

Toxicity and a therapeutic effect of the crystal or the pharmaceutical composition comprising the crystal of the present invention can be measured by determination of the $IC_{50}$ value of the crystal or the pharmaceutical composition comprising the crystal using a standard medicinal procedure in a cell culture or a laboratory animal. Data obtained from the cell culture assay and an animal experiment can be used for prescribing a range of a dosage used for human. The dosage for human is variable depending on the formulation and route of administration. In consideration of a patient's condition, each medical practitioner can select an exact formulation and route of administration and a dose (for example, refer to Fingl et al., 1975, in "The Pharmacological Basis of Therapeutics", and Ch.1, p. 1).

When it is orally administered to an adult, the dose is usually 0.1 μg-1 g/day, preferably is 0.01-200 mg/day, and in a case of parenteral administration, it is usually 1 μg-10 g/day, preferably 0.1 mg-10 mg/day, though it depends on the status of a disease, a route of administration and a patient's age or body weight.

Next, the method for preparing compound (I) in the present invention is explained.

A process for preparing compound (I) in the present invention was illustrated in scheme 1:

Scheme 1

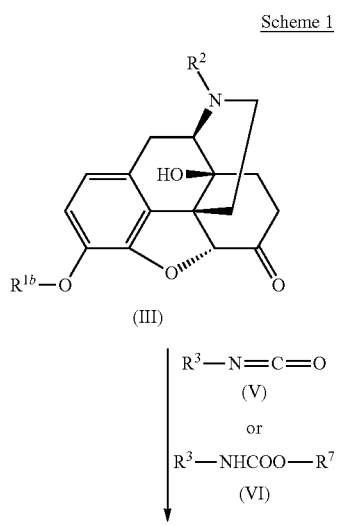

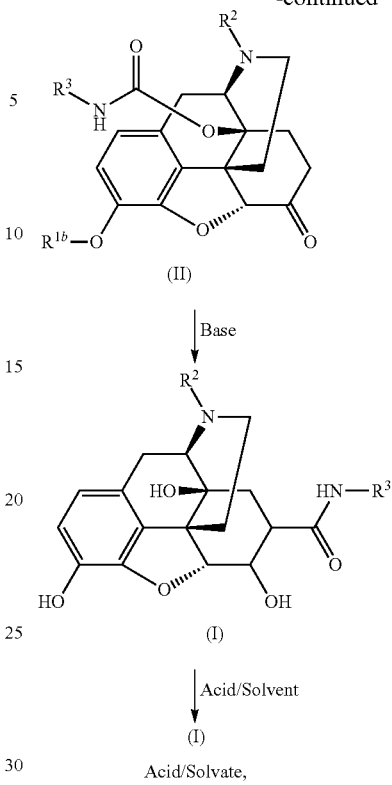

wherein $R^{1b}$ is a hydroxyl-protecting group; $R^2$ is optionally substituted alkyl; $R^3$ is optionally substituted alkyl, optionally substituted cycloalkyl, substituted or unsubstituted aryl, or substituted or unsubstituted heteraryl; and $R^7$ is optionally substituted phenyl.

According to the present invention, compound (I) can be obtained by adding a base to carbamate derivative (II) and reacting it at room temperature to below temperature of the boiling point of a solvent for 1 to 10 hours. As a base, an inorganic base such as lithium hydroxide, sodium hydroxide, potassium hydroxide, and cesium hydroxide is preferred, and the addition of aqueous solution containing 1-10 equivalent of the alkali to carbamate derivative (II) is preferable. The carbamate derivative can be preferably reacted by dissolving it in a hydrophilic solvent such as methanol, ethanol, 2-propanol, and DMSO etc. and the addition of the aqueous solution of alkali above.

Although the hydroxyl-protecting group of $R^{1b}$ in the carbamate derivative (II) is not limited in particular, it is possible to directly obtain the compound (I) if a protecting group which is deprotected by a base such as an acetyl group is adopted. In a case of the protective group which is not deprotected by a base, the deprotection may be carried out before or after the treatment with a base above.

Carbamate derivative (II) is obtained by reaction of an isocyanate derivative (V) with a compound (III). The reaction is carried out by adding a solution containing 0.5 to 5 equivalents, preferably 1.0 to 1.2 equivalents of the isocyanate derivative (IV) to the compound (III) into a solution of the compound (III), and reacting them at room temperature to below temperature of the boiling point of the solvent for 1 to 10 hours. It is preferable to add a Lewis acid catalyst such as $CuCl_2$ for example by 0.00005 to 1 equivalent, preferably 0.0001 to 0.1 equivalents, more preferably 0.0001 to 0.01 equivalents. Ethyl acetate, acetonitrile, acetone, toluene etc. can be used as a reaction solvent, though there is no restriction in particular.

The isocyanate derivative (V) above can be prepared by reacting the precursor of carbamate (VIII) wherein $R^5$ is lower alkyl in the presence of a Lewis acid and a base according to the following scheme:

Scheme 2

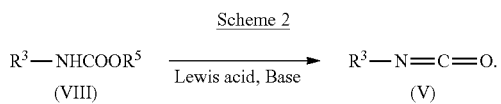

The carbamate derivative (II) can also be prepared by using a carbamic acid active ester (VI) wherein $R^7$ is optionally substituted phenyl in place of the isocyanate derivative. The active ester can be obtained by reacting chloroformate of the corresponding phenol with an amino derivative: $R^3$—$NH_2$:

Scheme 3

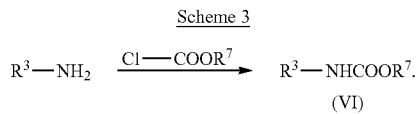

In the reaction, $R^7$ wherein $OR^7$ group works as a leaving group X is preferable, and a phenyl group, p-nitrophenyl group, p-chlorophenyl group etc. are specifically exemplified.

EXAMPLES

The present invention is explained in more detail by examples below, but these examples do not limit the present invention. Although an effort to guarantee accuracy about numerical values (for example, quantity, temperature, etc.) is paid, some errors and deviations should be taken into consideration. If not shown in particular, % is weight % of a component, and weight % is weight % of the full weight of a composition. A pressure is an atmospheric pressure or a pressure near it. A definition of abbreviations used in the present description is as follows: g is a gram, L is a liter, mg is a milligram, mL is a milliliter, Boc is a t-butoxycarbonyl group, Ac is acetyl, Me is a methyl group, Et is an ethyl group, and Pr is a propyl group.

(Measurement of an X-Ray Powder Diffraction Pattern)

X-ray powder diffraction measurement of the crystal obtained in each example was performed on the following measurement conditions in accordance with the X-ray powder diffraction method described to General Test Procedures of the Japanese pharmacopoeia.

(Device)
D-8 Discover (Bruker])
(Operation Method)
As to each sample, the following measurement condition was adopted.
Measuring method: Reflection method
The kind of light source: Cu bulb
Operating wavelength: CuKα rays
Tube current: 40 mA
Tube voltage: 40 Kv
Sample plate: Glass
Test range: 3°-40°

(Measurement of TG/DTA Data)
About 5 mg of each crystal obtained in each example were measured, and an aluminum pan was stuffed with it and measured in the open system. The measurement conditions are as follows.
(Measurement Conditions)
Device: TG/DTA 6300 by SEIKO
Measurement temperature range: 25° C.-300° C.
Heating rate: 10° C./minute Example 1-1

Preparation of p-toluenesulfonic acid salt [compound (9)] of compound (IA)

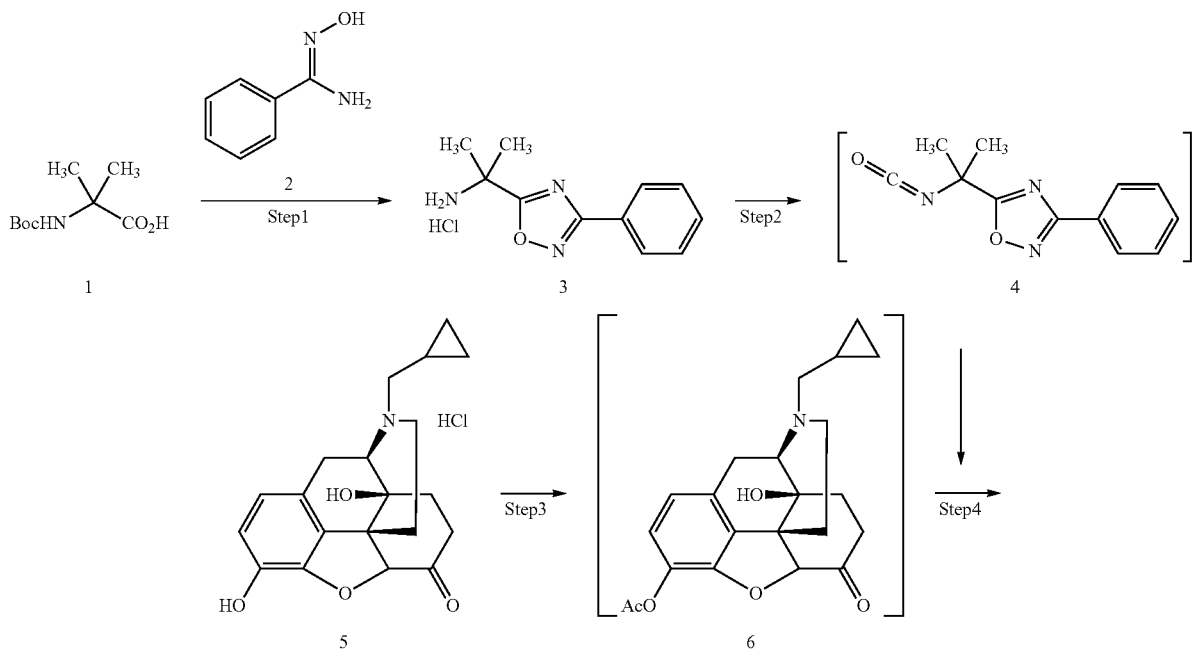

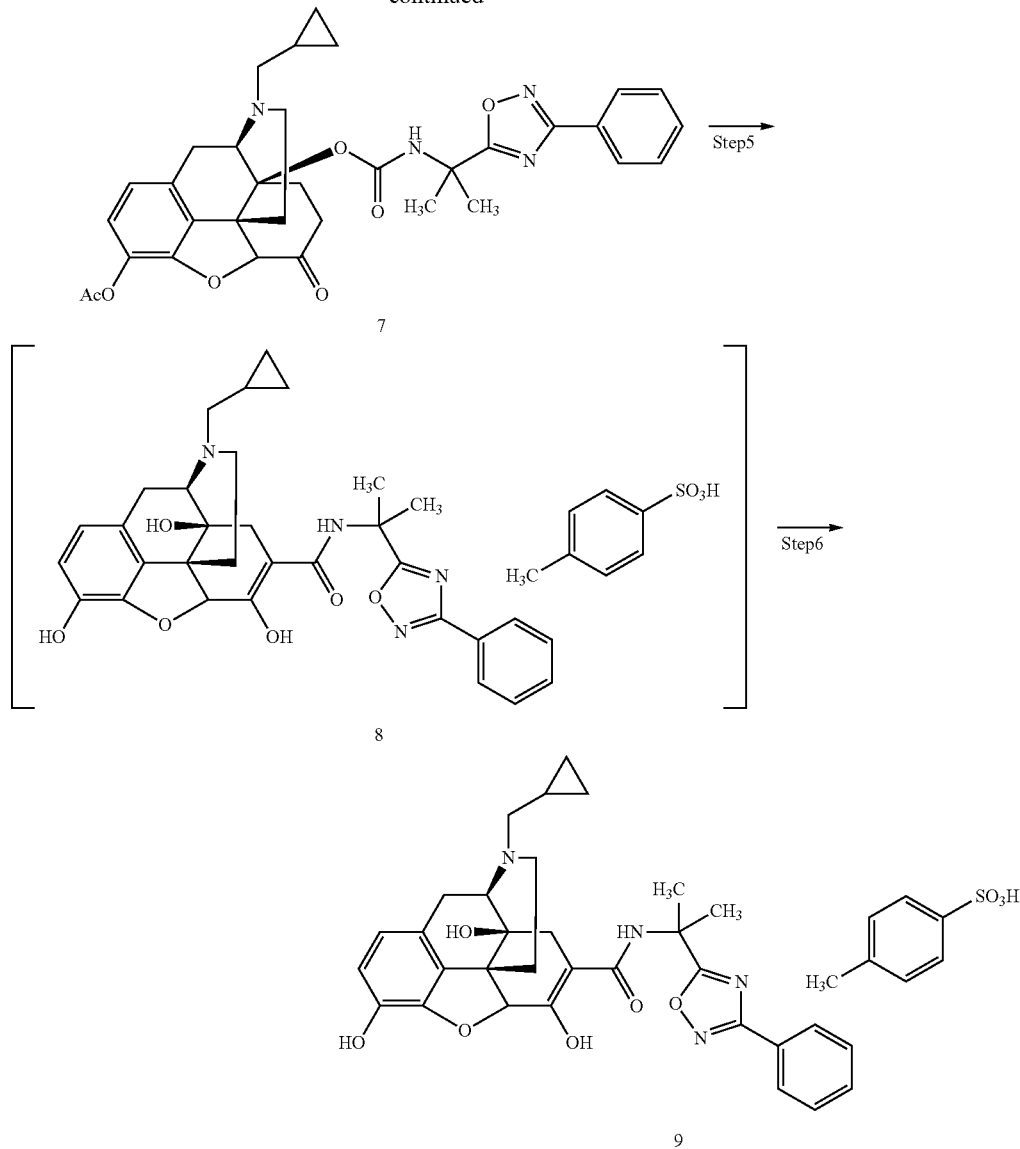

Step 1: Synthesis of Compound (3)

Diisopropylethylamine (17.5 g, 135.4 mmol) was added to a solution of t-butoxycarbonylamino isobutyric acid (1) (25.0 g, 123 mmol) in n-propyl acetate (150 ml) at 0° C. To the mixture was added isobutyl chloroformate (17.6 g, 128.9 mmol) dropwise at the same temperature and stirred for an hour. A solution of benzamide oxime (2) (17.6 g, 129.3 mmol) in n-propyl acetate (100 ml) was added thereto and stirred at 0° C. for 1 hour, and then at 95° C. for 5 hours. The acid aqueous solution was added, and the organic layer was separated, washed with sodium hydrogen carbonate and water and concentrated in vacuo. Hydrochloric acid was added to the reaction solution, stirred for 2.5 hours, and the precipitated crystal was collected by filtration, washed and dried to give compound (3) (27.34 g, 92.7%).

$^1$H NMR (300-MHz, DMSO-$d_6$) δ: 1.80 (6H, s), 7.59-7.64 (3H, m), 8.01-8.05 (2H, m), 9.26 (3H, br).

Step 2: Synthesis of Compound (4)

An alkaline water was added to a suspension of compound (3) (19.0 g, 79.2 mmol) in toluene (150 ml) at 25° C. and stirred. Methyl chloroformate (8.3 g, 88.0 mmol) was added at 50° C., stirred for an hour, the organic layer was separated, washed with aqueous hydrochloric acid, an aqueous solution of sodium hydrogen carbonate and water successively, and concentrated in vacuo. A solution of boron trichloride (1.0 mol/L; 7.3 ml) in toluene was added thereto, triethylamine was added dropwise at 50° C. and stirred for 2 hours. The reaction solution was concentrated to give solution of compound (4.)

Step 3: Synthesis of Compound (6)

Triethylamine (11.3 g, 111.7 mmol) and acetic anhydride (5.7 g, 55.8 mmol) were added to a solution of a commercial naltrexone hydrochloride (5) (20.0 g, 52.9 mmol) in ethyl acetate (160 ml), and stirred at 40° C. for 2 hours. The reaction solution was cooled, washed with water and concentrated to give a solution of compound (6).

$^1$H-NMR (300 MHz, DMSO-$d_6$) δ 0.14 (2H, d, J=4.8 Hz), 0.49 (2H, d, J=7.8 Hz), 0.88 (1H, m), 1.29 (1H, d, J=9.9 Hz), 1.46 (1H, td, J=14.1, 3.3 Hz), 1.79(1H, dt, J=12.0, 3.3 Hz), 1.90-2.00(1H, m), 2.11(1H, dt, J=14.4, 3.3 Hz), 2.26 (3H, s), 2.30-2.46 (3H, m), 2.52-2.72(2H, m), 2.92(1H, td, J=14.1, 4.8 Hz), 3.07(1H, d, J=18.9 Hz), 3.17(1H, d, J=5.7 Hz), 4.91(1H, s), 5.18(1H, s), 6.71(1H, d, J=8.1 Hz), 6.83(1H, d, J=8.1 Hz)

Step 4: Synthesis of Compound (7)

The reaction solution of the compound (4) and ethyl acetate were added to the solution of the compound (6), an aqueous solution of copper (II) chloride was added thereto and stirred at 25° C. for 4 hours. Heptane was added to the reaction solution, and crystallization was carried out. Filtering, washing and drying afforded compound (7) (89.2%).

$^1$H-NMR (300 MHz, DMSO-$d_6$) δ 0.20-0.40 (2H, m), 0.60-0.90 (1H, m), 1.20-1.50 (2H, m), 1.67 (3H, s), 1.74 (3H, s), 1.90-2.10 (2H, m), 2.10-2.20 (2H, m), 2.26 (3H, s), 2.30-2.55 (2H, m), 2.58-2.80 (4H, m), 3.03(2H, m), 4.31(1H, s), 4.81(1H, s), 6.71(1H, d, J=8.1 Hz), 6.85(1H, d, J=7.8 Hz), 7.50-7.70(3H, m), 7.92-8.01(2H, m), 8.11(1H, s).

Step 5: Synthesis of Compound (8)

An aqueous solution of potassium hydroxide was added dropwise to a suspension of the compound (7) (5.5 g, 9.0 mmol) in 2-propanol (22 ml), and stirred at 80° C. for 5 hours. The reaction solution was washed with toluene, adjusted to pH 7.0 to 8.0 and extracted with n-propyl acetate. The organic layer was washed with water, 2-propanol and n-propyl acetate were added and concentrated. A solution of p-toluenesulfonic acid (1.5 g, 8.1 mmol) in 2-propanol was added to carry out the crystallization. After being cooled, the precipitated solid was collected by filtration to give undried product (8) (n-propyl acetate/2-propanol solvate of p-toluenesulfonic acid salt).

The result of the X-ray powder diffraction and TG/DTA analysis of the undried product (8) (n-propyl acetate/2-propanol solvate of p-toluenesulfonic acid salt) is shown in the following reference example 3.

Step 6: Synthesis of Compound (9)

The undried product (8) was dissolved in methanol and n-propyl acetate by warming, and the solution was filtered, washed and concentrated in vacuo. The precipitate was collected by filtration, washed to give a crude product, which was dried at 60° C. for 3 hours in vacuo to give crystal of compound (9) (non-solvate: 66.3%).

$^1$H-NMR (300 MHz, DMSO-$d_6$) δ 13.37 (1H, s), 9.44 (1H, s), 8.95 (1H, br s), 8.12 (1H, s), 7.99-7.96 (2H, m), 7.60-7.53 (3H, m), 7.49-7.45 (2H, m), 7.11 (2H, d, J=8.4 Hz), 6.69 (2H, ABq.), 6.56 (1H, s), 4.94 (1H, s), 3.95 (1H, d, J=5.1 Hz), 3.50-3.25 (2H, m), 3.07 (2H, br d, J=12 Hz), 3.00-2.90 (1H, m), 2.75-2.60 (1H, m), 2.60-2.40 (2H, m), 2.29 (3H, s), 2.10 (1H, d, J=14.7 Hz), 1.70 (6H, s), 1.75-1.60 (1H, m), 1.15-0.95 (1H, m), 0.80-0.55 (2H, m), 0.55-0.35 (2H, m).

Results of X-ray powder diffraction are shown in FIG. 1 and Table 2.

TABLE 2

| 2θ (°) | d Values (Angstrom) | Intensities Counts | Intensities Relative (%) |
|---|---|---|---|
| 7.8 | 11.36376 | 54.5 | 100 |
| 8.2 | 10.72766 | 25.9 | 47.4 |
| 9.8 | 8.99543 | 14.4 | 26.4 |
| 10.3 | 8.58122 | 15.8 | 28.9 |
| 10.6 | 8.3496 | 47.4 | 86.9 |
| 12.6 | 7.02714 | 18.3 | 33.6 |
| 13.3 | 6.63904 | 16.5 | 30.3 |
| 13.9 | 6.38338 | 12.8 | 23.4 |
| 15.4 | 5.75638 | 26.5 | 48.6 |
| 15.6 | 5.66021 | 48.2 | 88.3 |
| 17.1 | 5.19163 | 10.6 | 19.5 |
| 17.8 | 4.97759 | 49.8 | 91.4 |
| 18.6 | 4.77808 | 40.5 | 74.3 |
| 19.2 | 4.61818 | 13.4 | 24.5 |
| 19.8 | 4.4847 | 15.8 | 29.1 |
| 20.4 | 4.35494 | 30 | 54.9 |
| 20.6 | 4.30073 | 25.3 | 46.5 |
| 21.5 | 4.121 | 41.8 | 76.7 |
| 21.9 | 4.05431 | 31.3 | 57.3 |
| 22.6 | 3.93127 | 18.4 | 33.8 |
| 22.9 | 3.8839 | 16.7 | 30.6 |
| 23.6 | 3.76898 | 37.8 | 69.2 |
| 24.3 | 3.6633 | 22.8 | 41.8 |
| 25.5 | 3.48533 | 29.3 | 53.7 |
| 26.6 | 3.3465 | 13.3 | 24.4 |
| 27.1 | 3.28401 | 19.8 | 36.3 |
| 27.8 | 3.2029 | 25.8 | 47.3 |
| 28.1 | 3.17733 | 19.6 | 36 |
| 29.3 | 3.04802 | 13.1 | 23.9 |
| 30.1 | 2.96936 | 21.2 | 38.8 |
| 30.6 | 2.91858 | 18.1 | 33.3 |
| 31.9 | 2.80554 | 15.7 | 28.8 |
| 34.0 | 2.63206 | 10.3 | 18.9 |
| 35.5 | 2.52595 | 10.6 | 19.4 |
| 38.0 | 2.36364 | 9.24 | 16.9 |

In the X-ray powder diffraction spectrum, peaks were observed at diffraction angles of (2θ): 7.8°±0.2°, 10.6°±0.2°, 15.6°±0.2°, 17.8°±0.2°, 18.6°±0.2°, 20.4°±0.2°, 21.5°±0.2°, 21.9°±0.2°, 23.6°±0.2° and 25.5°±0.2°.

Figure 14:
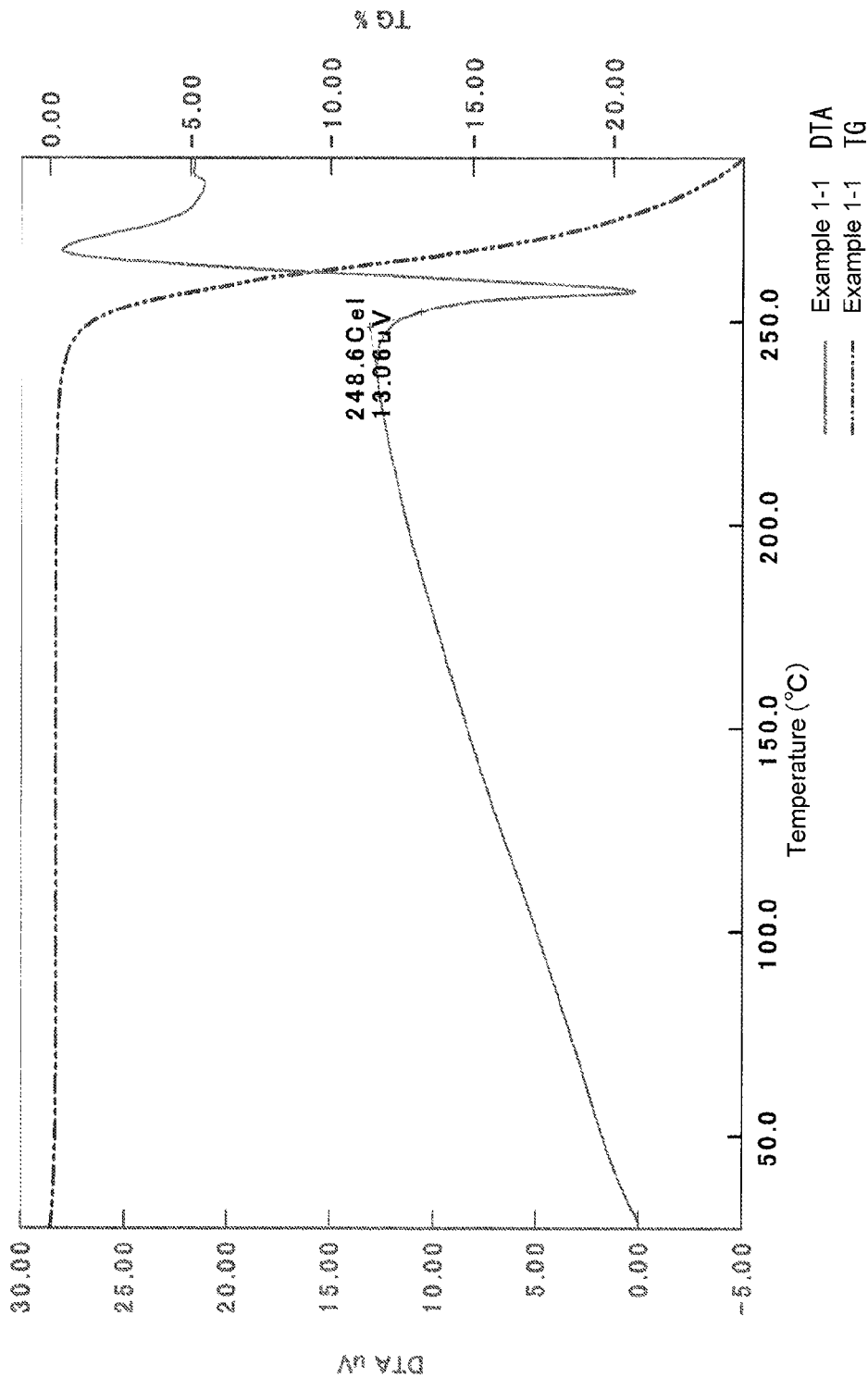
FIG. 14 shows results of TG/DTA analyses of the crystal (non-solvate) of a p-toluenesulfonic acid salt of the compound (IA) in the present invention.

Results of TG/DTA analysis are shown in FIG. 14.

Example 1-2

Preparation of p-toluenesulfonic acid salt [compound (9)] of compound (IA) (alternative method A)

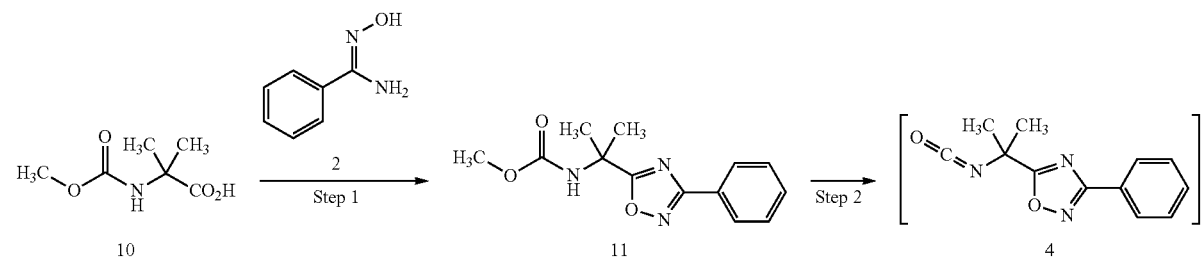

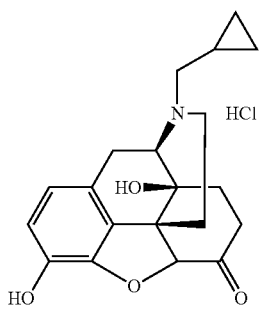

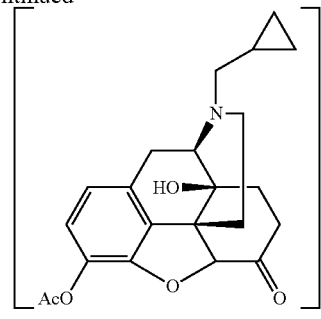

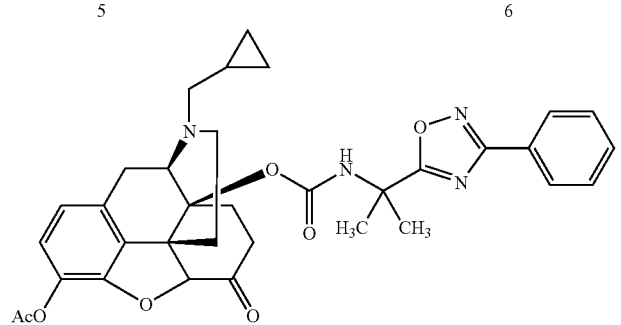

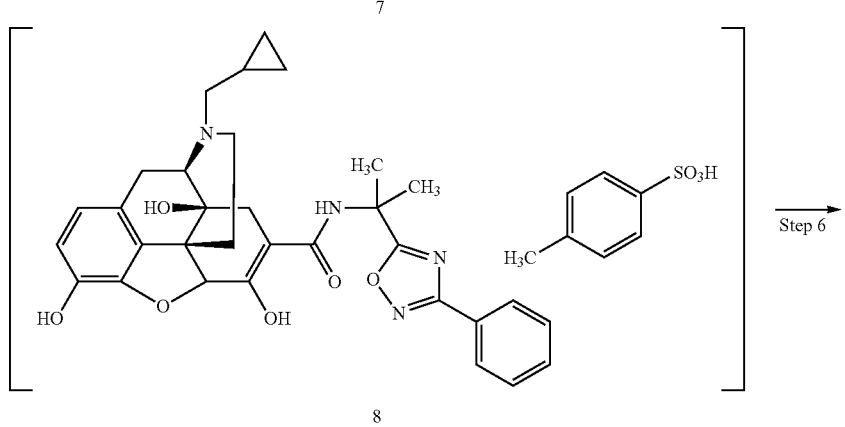

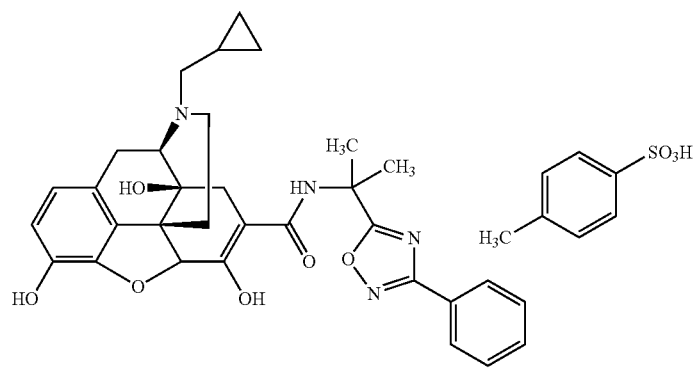

Step 1: Synthesis of Compound (11)

CDI (carbonyldiimidazole, 5.28 g, 31.1 mmol) and acetonitrile (5 ml) were added to a suspension of methoxycarbonyl-2-methylalanine (10) (5.00 g, 31.0 mmol) in acetonitrile (25 ml) at 0° C., and stirred for 1.5 hours. Benzamide oxime (2) (4.65 g, 34.2 mmol), and acetonitrile (20 ml) were added at the same temperature and stirred for 2 hours. An aqueous solution of potassium carbonate [0.10 equivalent to compound (10): 0.43 g] in water (15 ml) was added thereto at once and reacted at temperature below the boiling point of the solvent for 1-5 hours. After being concentrated in vacuo, water was added and the precipitated crude product was collected by filtration and washed. The undried product was dried to give compound (11) (7.43 g, yield 91.7%).

¹H-NMR (300 MHz, CDCl₃) δ: 1.81 (6H, s), 3.65 (3H, s), 5.46 (1H, s), 7.49-7.50 (3H, m), 8.05-8.08 (2H, m).

Step 2: Synthesis of Compound (4)

Triethylamine (7.55 g, 74.63 mmol) was added dropwise to a solution of the compound (11) (15.12 g, 57.41 mmol) and aluminum trichloride (9.19 g, 68.89 mmol) in toluene at 50° C., and stirred at the same temperature for 2.5 hours. The organic layer was separated and concentrated to give a reaction solution of compound (4).

¹H-NMR (300 MHz, CDCl₃) δ: 1.84 (6H, s), 7.31-7.55 (3H, m), 8.05-8.13 (2H, m).

¹³C-NMR (75 MHz, CDCl₃) δ: 29.85, 55.71, 126.16, 127.44, 128.78, 131.35, 168.23, 180.88.

IR (cm⁻¹): 1446, 1478, 1570, 1638, 2256, 2986, 3337.

Step 3-6: Synthesis of Compound (9)

Compound (9) (non-solvate) was synthesized from the compound (5) through the same steps as example 1-1.

Example 1-3

Preparation of p-toluenesulfonic acid salt [compound (9)] of compound (IA) (alternative method B)

ethyl acetate. The extract was washed with brine, dried over anhydrous sodium sulfate, filtered and concentrated. Hexane (ca. 20 ml) was added to the resulting pale yellow oil (4.88 g) being solidified under ice-cooling. The obtained solid was collected by filtration, washed with hexane to give a target compound (16) (3.74 g) as a white solid.

¹H-NMR (CDCl₃) δ 8.24 (2H, d, J=9.3 Hz), 8.09 (2H, m), 7.53-7.45 (3H, m), 7.33 (2H, br d, J=8.7 Hz), 5.99 (1H, br s), 1.92 (6H, s).

Step 2

The compound (6) (3.28 g, 8.56 mmol) synthesized by the same method as step 3 of example 1-1 and the compound (16) (3.79 g, 10.3 mmol) were dissolved in acetonitrile (10 ml) and refluxed for 22 hours. The reaction solution was cooled to room temperature, poured into ice water and extracted with ethyl acetate twice. The extract was washed with 0.1 mol/L aqueous solution of sodium hydroxide twice and with brine once, dried over anhydrous magnesium sulfate, filtered and concentrated. The obtained amorphous compound (7) (5.46 g) was used at the next step without purification.

¹H-NMR (DMSO-d₆) δ 8.0-7.9 (2H, m), 7.6-7.5 (3H, m), 6.9-6.7 (2H, Abq.), 4.32 (1H, s), 3.2-1.2 (12H, m), 2.26 (3H,

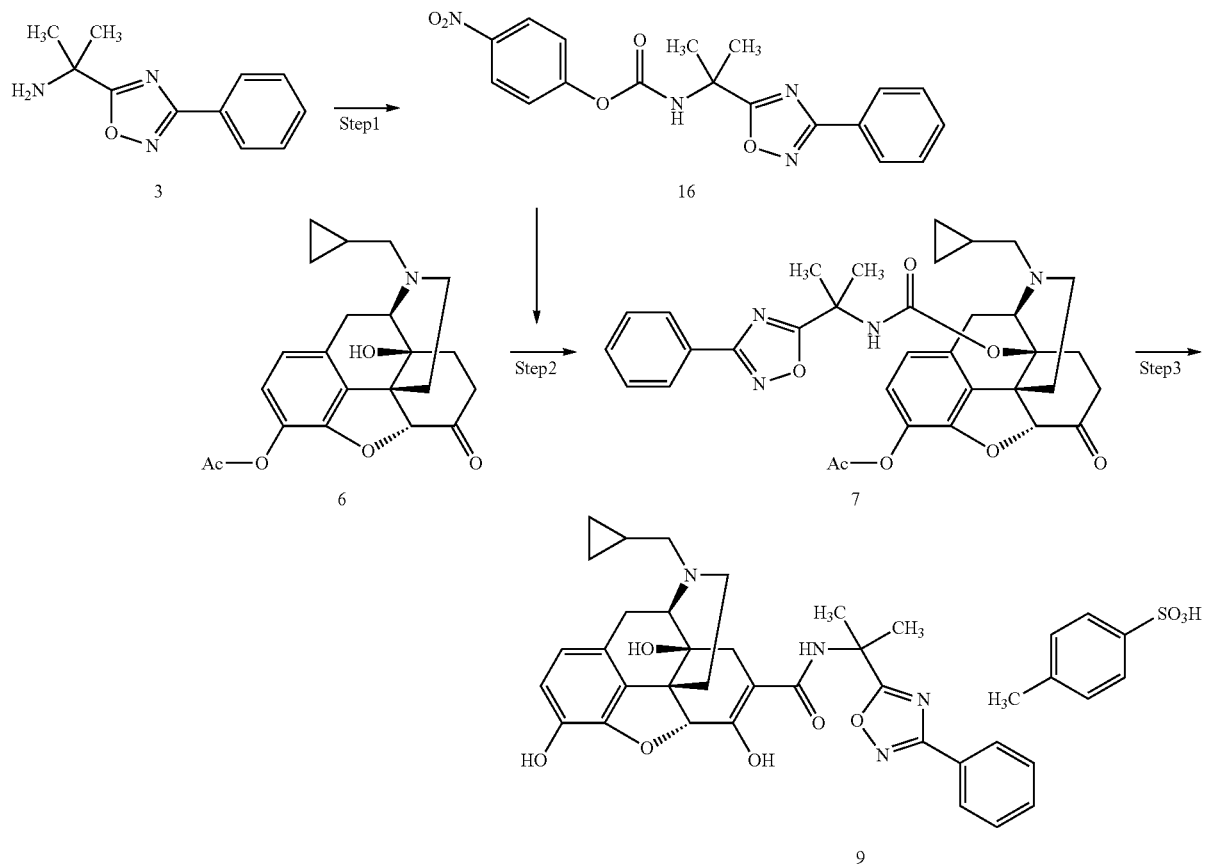

Step 1

Compound (3) (2.03 g, 10.0 mmol) synthesized by the same method as step 1 of example 1-1 was dissolved in acetonitrile (20 ml), pyridine (0.89 ml, 11.0 mmol) and 4-nitrophenyl chloroformate (2.22 g, 11.0 mmol) were added under ice-cooling, and stirred at room temperature for 1.5 hours. The reaction solution was poured into ice-water containing 2 mol/L hydrochloric acid and extracted twice with s), 1.71 (1H, d, J=21.6 Hz), 1.61 (6H, s), 0.95-0.65 (1H, m), 0.55-0.2 (2H, m), 0.2-0.5 (2H, m).

Step 3

The compound (7) (500 mg) was dissolved in dimethyl sulfoxide (2 ml), 2 mol/L aqueous solution of potassium hydroxide (2 ml) was added and stirred at 80° C. for 6 hours. The reaction solution was cooled to room temperature, neutralized with 2 mol/L hydrochloric acid, and extracted with ethyl acetate twice. The extract was washed with 0.1 mol/L aqueous solution of sodium hydroxide and brine successively, dried over anhydrous sodium sulfate, filtered and concentrated. The obtained pale yellow amorphous solid (412 mg) was dissolved in methanol (2 ml), p-toluenesulfonic acid hydrate (165 mg) was added and left stand for 30 minutes. Then, acetonitrile (20 ml) was added and left stand at 5° C. overnight. The precipitate was collected by filtration and dried in vacuo to give p-toluenesulfonic acid salt (9) (non-solvate: 282 mg) as crystal (yield from the compound (6): 48%).

$^1$H-NMR (DMSO-$d_6$) δ 13.37 (1H, s), 9.44 (1H, s), 8.95 (1H, br s), 8.12 (1H, s), 7.99-7.96 (2H, m), 7.60-7.53 (3H, m), 7.49-7.45 (2H, m), 7.11 (2H, d, J=8.4 Hz), 6.69 (2H, ABq.), 6.56 (1H, s), 4.94 (1H, s), 3.95 (1H, d, J=5.1 Hz), 3.50-3.25 (2H, m), 3.07 (2H, br d, J=12 Hz), 3.00-2.90 (1H, m), 2.75-2.60 (1H, m), 2.60-2.40 (2H, m), 2.29 (3H, s), 2.10 (1H, d, J=14.7 Hz), 1.70 (6H, s), 1.75-1.60 (1H, m), 1.15-0.95 (1H, m), 0.80-0.55 (2H, m), 0.55-0.35 (2H, m).

Example 1-4

Preparation of p-toluenesulfonic acid salt [compound (9)] of compound (IA) (alternative method C)

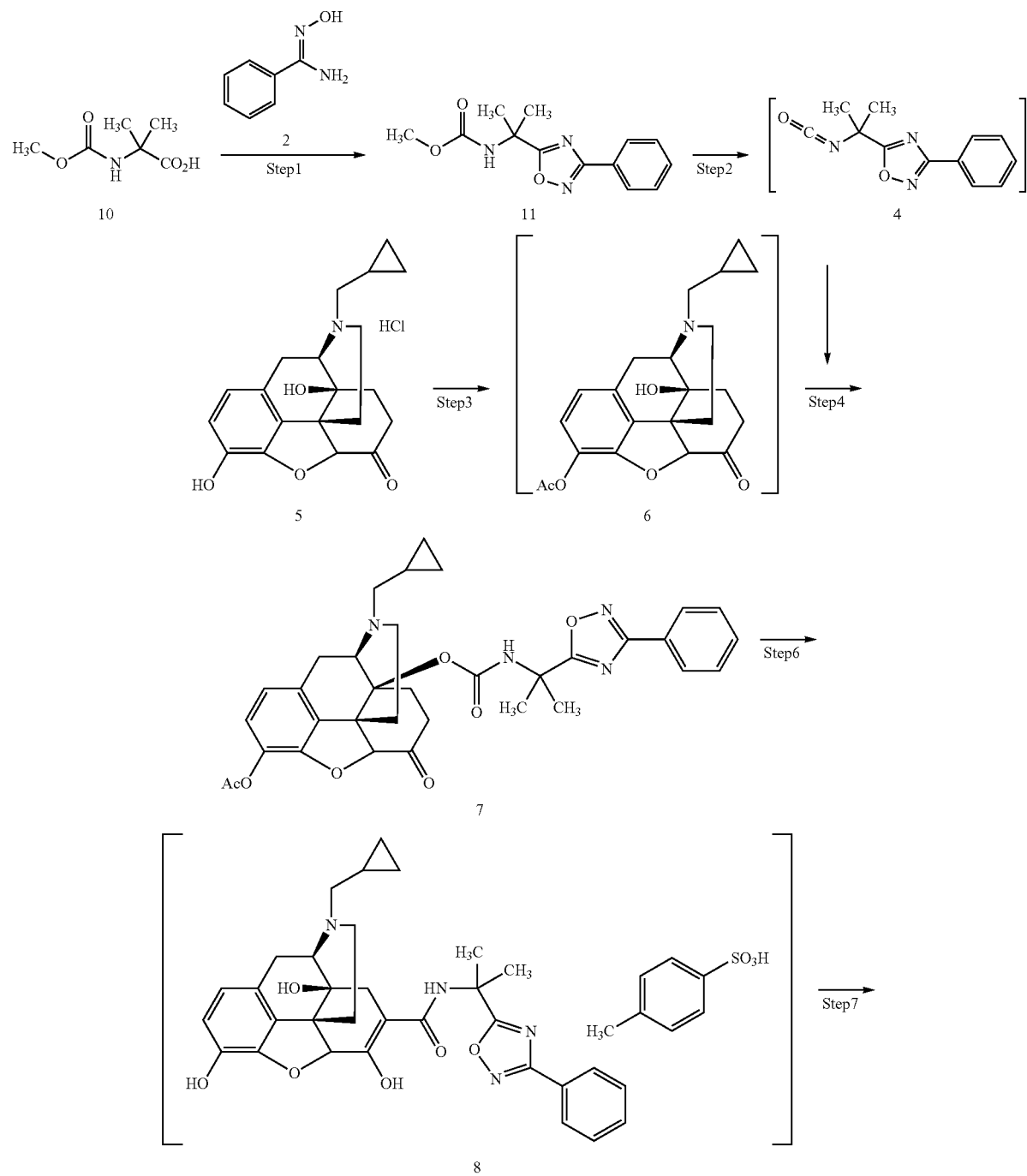

-continued

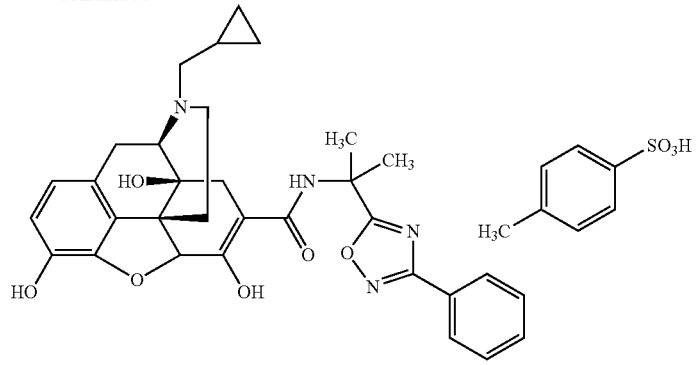

9

Step 1: Synthesis of Compound (4)

Toluene was added to the compound (11) (0.5 g, 1.91 mmol) synthesized by the same method as step 1 of example 1-2, TiCl$_4$ (2.30 mmol) was added thereto and the mixture was heated to 50° C. Triethylamine (2.30 mmol) was added to the reaction solution and stirred at the same temperature for 2 hours to give a reaction solution of compound (4).

Step 2-7: Synthesis of Compound (9)

A compound (9) (non-solvate) was synthesized from the compound (5) through the same steps as those of example 1-1.

Example 2

Synthesis of Compound (20)

Step 1

Compound (17) (4.51 g, 36 mmol) was dissolved in acetonitrile (45 ml), and pyridine (3.20 ml, 39.6 mmol) and phenyl chloroformate (5.00 ml, 39.6 mmol) were added under ice-cooling. Dimethylformamide (9 ml) and acetonitrile (30 ml) were added and stirred at room temperature for 45 minutes. The precipitate in the reaction solution was collected by filtration, washed with cold methanol and water and dried in vacuo to give a target compound (18) (7.02 g) as a white solid.

$^1$H-NMR (CDCl$_3$) δ 8.61 (1H, s), 7.43 (2H, t, J=7.8 Hz), 7.41 (1H, s), 7.29 (1H, t, J=7.8 Hz), 7.21 (2H, d, J=7.8 Hz), 3.97 (3H, s).

Step 2

Compound (6) (1.92 g, 5.00 mmol) synthesized by the same method as step 3 of example 1-1 and compound (18) (1.84 g, 7.50 mmol) were dissolved in dimethylformamide

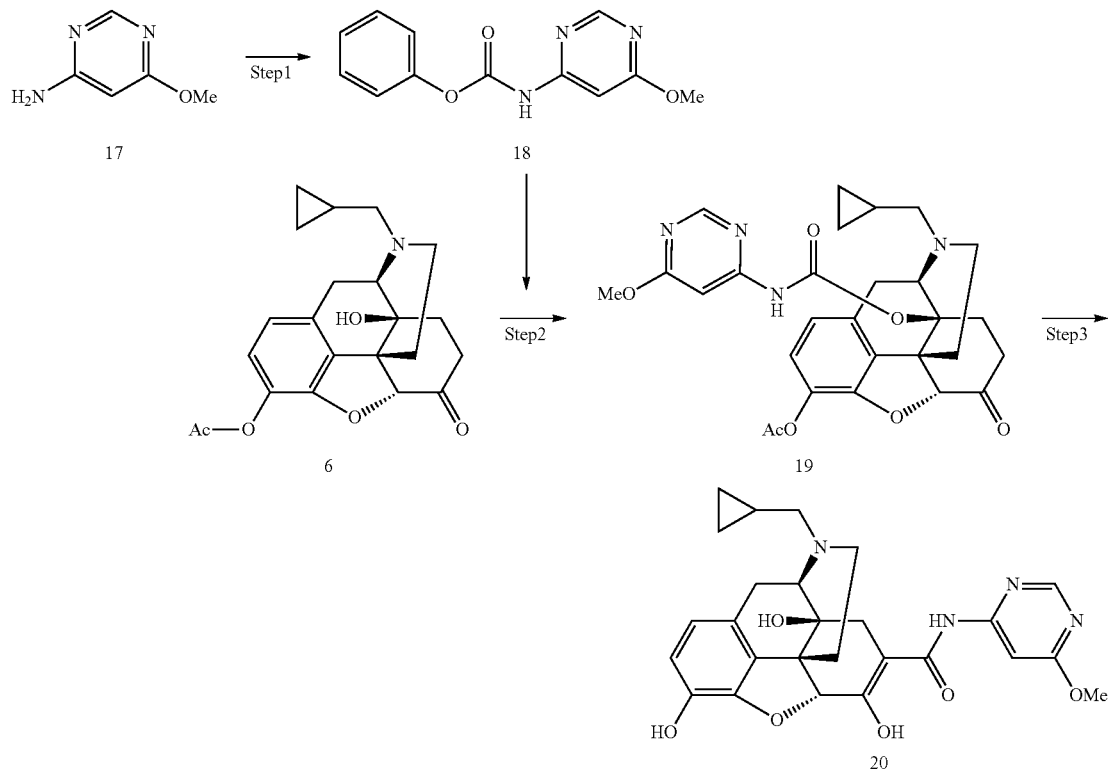

(10 ml), and stirred at 120° C. for 4 hours. The reaction solution was cooled back to room temperature, acetonitrile (50 ml) was added and the precipitate was filtered. The filtrate was concentrated at 60° C. in vacuo, and dimethylformamide was evaporated. Acetonitrile (100 ml) was added to the residue and stirred under ice cooling for 30 minutes. The precipitated crystal was collected by filtration, washed with cold acetonitrile and dried in vacuo to give the first crystal (1.66 g) of the compound (19). Also, the mother liquid was concentrated, and diethyl ether was added to the residue and stirred at room temperature to give a second crystal (306 mg) and a third crystal (71 mg).

$^1$H-NMR (DMSO-$d_6$) δ 10.58 (1H, br s), 8.52 (1H, s), 7.19 (1H, s), 6.83 (2H, Abq.), 4.78 (1H, s), 4.44 (1H, d, J=5.4 Hz), 3.90 (3H, s), 3.12 (1H, d, J=18.6 Hz), 2.9-2.55 (4H, m), 2.35 (1H, dd, J=6.3 Hz, 12.6 Hz), 2.27 (3H, s), 2.25-2.12 (3H, m), 2.1-1.9 (1H, m), 1.62-1.48 (1H, m), 1.28-1.20 (1H, m), 0.75-0.62 (1H, m), 0.35 (2H, d, J=7.5 Hz), 0.1-0.5 (2H, m).

Step 3

Compound (19) (2.02 mg, 3.78 mmol) was dissolved in methanol (9.5 ml), 2 mol/L aqueous solution of potassium hydroxide (9.5 ml) was added and stirred at 60° C. for 2.5 hours. The reaction solution was cooled back to room temperature, neutralized with 2 mol/L hydrochloric acid under ice-cooling, and methanol was evaporated. The precipitated crude crystal was collected by filtration, recrystallized from a mixture of ethyl acetate and methanol (1:1) to give a target compound (20) (1.44 g, yield 77%) as crystal.

$^1$H-NMR (DMSO-$d_6$) δ 14.2 (1H, br s), 9.19 (1H, s), 8.8 (1H, br s), 8.32 (1H, s), 7.49 (1H, s), 6.56 (2H, ABq.), 6.1 (1H, br s), 4.53 (1H, br s), 3.82 (3H, s), 3.5-2.3 (9H, m), 1.82 (1H, d, J=15.6 Hz), 1.53 (1H, br d, J=13.5 Hz), 1.15-0.95 (1H, m), 0.75-0.5 (2H, m), 0.5-0.3 (2H, m).

Example 3-1

Synthesis of Compound (7) (Method 1)

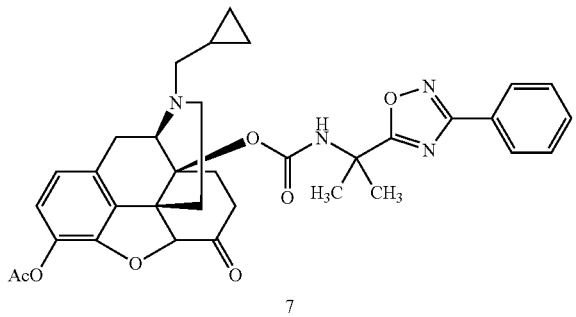

Compound (6) (corresponding to naltrexone hydrochloride 5.00 g) synthesized through the same method as step 3 of example 1-1 was dissolved in ethyl acetate, acetic acid (0.1 equivalent) was added and warmed to 50° C. A solution of the compound (4) synthesized through the same method as step 1 and 2 of example 1-1 was added thereto and stirred at the same temperature for 6.5 hours. Heptane was added to the reaction solution, the precipitated solid was collected by filtration, washed and dried to give compound (7) (6.92 g, 85.3%).

Example 3-2

Synthesis of Compound (7) (Method 2)

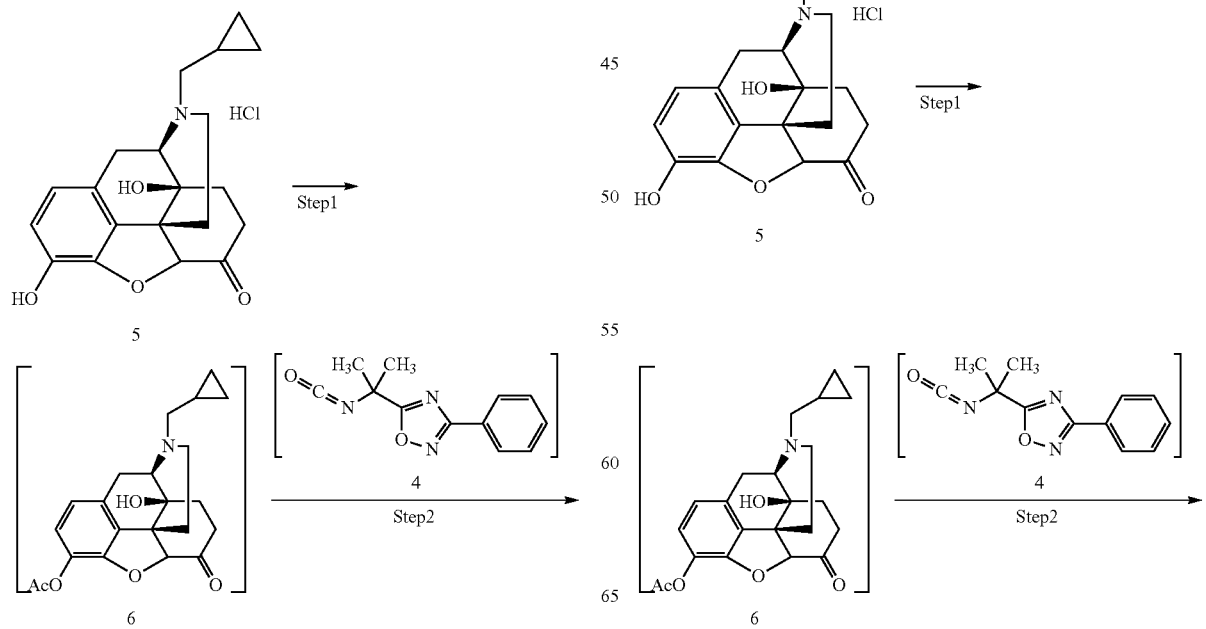

-continued

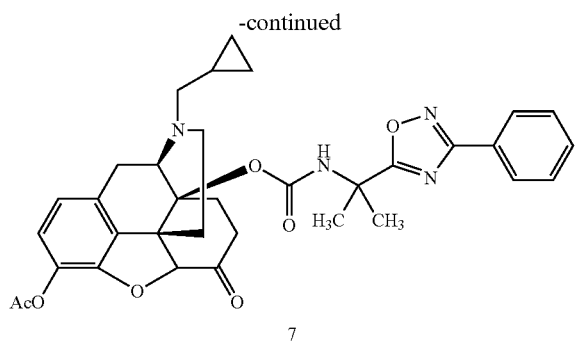

7

Compound (6) synthesized through the same method as step 3 of example 1-1 was dissolved in ethyl acetate, and compound (4) (1.5 equivalent) and toluene were added thereto and stirred 70° C. for 8 hours to give compound (7).

Example 4

Preparation of p-toluenesulfonic acid salt hydrate crystal (form I) of compound (IA)

A mixture of 2-propanol (25 mL) and water (2.5 mL) was added to p-toluenesulfonic acid salt (non-solvate; 5.00 g) prepared according to Example 1-1 above and dissolved by warming. Acetonitrile (50 mL) was added and stirred at room temperature for 4 hours. The precipitated crystal was collected by filtration, dried at 85° C. in vacuo for 4 hours to give the crystal (4.68 g).

Elemental Analysis:
Calculated: C, 60.28; H, 5.94; N, 7.21; S, 4.13 (calculated as 1.9 H$_2$O).
Measured: C, 60.5; H, 6.17; N, 7.21; S, 3.83
Results of X-ray powder diffraction are shown in FIG. 2 and Table 3.

TABLE 3

| 2θ (°) | d Values (Angstrom) | Intensities Counts | Intensities Relative (%) |
|---|---|---|---|
| 3.9 | 22.42624 | 5.9 | 14.3 |
| 6.6 | 13.29975 | 24 | 58.1 |
| 7.0 | 12.65995 | 9.32 | 22.5 |
| 8.9 | 9.8781 | 26 | 62.9 |
| 10.9 | 8.12859 | 8.88 | 21.5 |
| 11.4 | 7.75464 | 25.2 | 61 |
| 11.8 | 7.49216 | 9.61 | 23.2 |
| 12.9 | 6.86462 | 30.1 | 72.8 |
| 13.2 | 6.70175 | 9.92 | 24 |
| 14.0 | 6.34239 | 22.7 | 55 |
| 15.0 | 5.91272 | 21.7 | 52.4 |
| 16.1 | 5.48702 | 16 | 38.6 |
| 17.6 | 5.03163 | 26.9 | 65.1 |
| 18.2 | 4.86625 | 24.9 | 60.2 |
| 19.5 | 4.5484 | 27.6 | 66.8 |
| 19.8 | 4.46964 | 22.6 | 54.7 |
| 20.5 | 4.32695 | 18.9 | 45.8 |
| 21.9 | 4.04931 | 21.7 | 52.6 |
| 22.4 | 3.96745 | 41.3 | 100 |
| 22.7 | 3.91399 | 16.7 | 40.5 |
| 23.2 | 3.83498 | 13.5 | 32.6 |
| 23.5 | 3.78926 | 14.9 | 36 |
| 24.2 | 3.67828 | 10.4 | 25.2 |
| 24.7 | 3.59847 | 11.8 | 28.5 |
| 25.4 | 3.50836 | 32.2 | 77.9 |
| 25.8 | 3.4503 | 18.8 | 45.5 |
| 26.0 | 3.42466 | 23.8 | 57.5 |
| 26.5 | 3.36674 | 17.7 | 42.8 |

TABLE 3-continued

| 2θ (°) | d Values (Angstrom) | Intensities Counts | Intensities Relative (%) |
|---|---|---|---|
| 27.2 | 3.27921 | 12.4 | 30.1 |
| 27.9 | 3.19009 | 15.8 | 38.3 |
| 28.4 | 3.1428 | 16.9 | 41 |
| 28.7 | 3.10569 | 27.4 | 66.2 |
| 29.4 | 3.03917 | 12.2 | 29.6 |
| 29.8 | 2.99128 | 17.4 | 42.1 |
| 30.6 | 2.91869 | 20.1 | 48.5 |
| 31.0 | 2.882 | 16.2 | 39.1 |
| 32.4 | 2.75983 | 11.5 | 27.7 |
| 32.8 | 2.73197 | 12.8 | 31 |
| 33.3 | 2.68931 | 9.88 | 23.9 |
| 34.0 | 2.63686 | 9.75 | 23.6 |
| 34.5 | 2.59415 | 12.7 | 30.8 |
| 35.5 | 2.52787 | 11.9 | 28.9 |
| 36.0 | 2.49303 | 13 | 31.4 |
| 37.0 | 2.42814 | 12.6 | 30.4 |
| 37.7 | 2.387 | 8.41 | 20.3 |
| 38.8 | 2.31749 | 8.04 | 19.5 |

In the X-ray powder diffraction spectrum, peaks were observed at diffraction angles of (2θ): 6.6°±0.2°, 8.9°±0.2°, 11.4°±0.2°, 12.9°±0.2°, 14.0°±0.2°, 15.0°±0.2°, 17.6°±0.2°, 18.2°±0.2°, 22.4°±0.2°, 25.4°±0.2° and 28.7°±0.2°.

Figure 15:
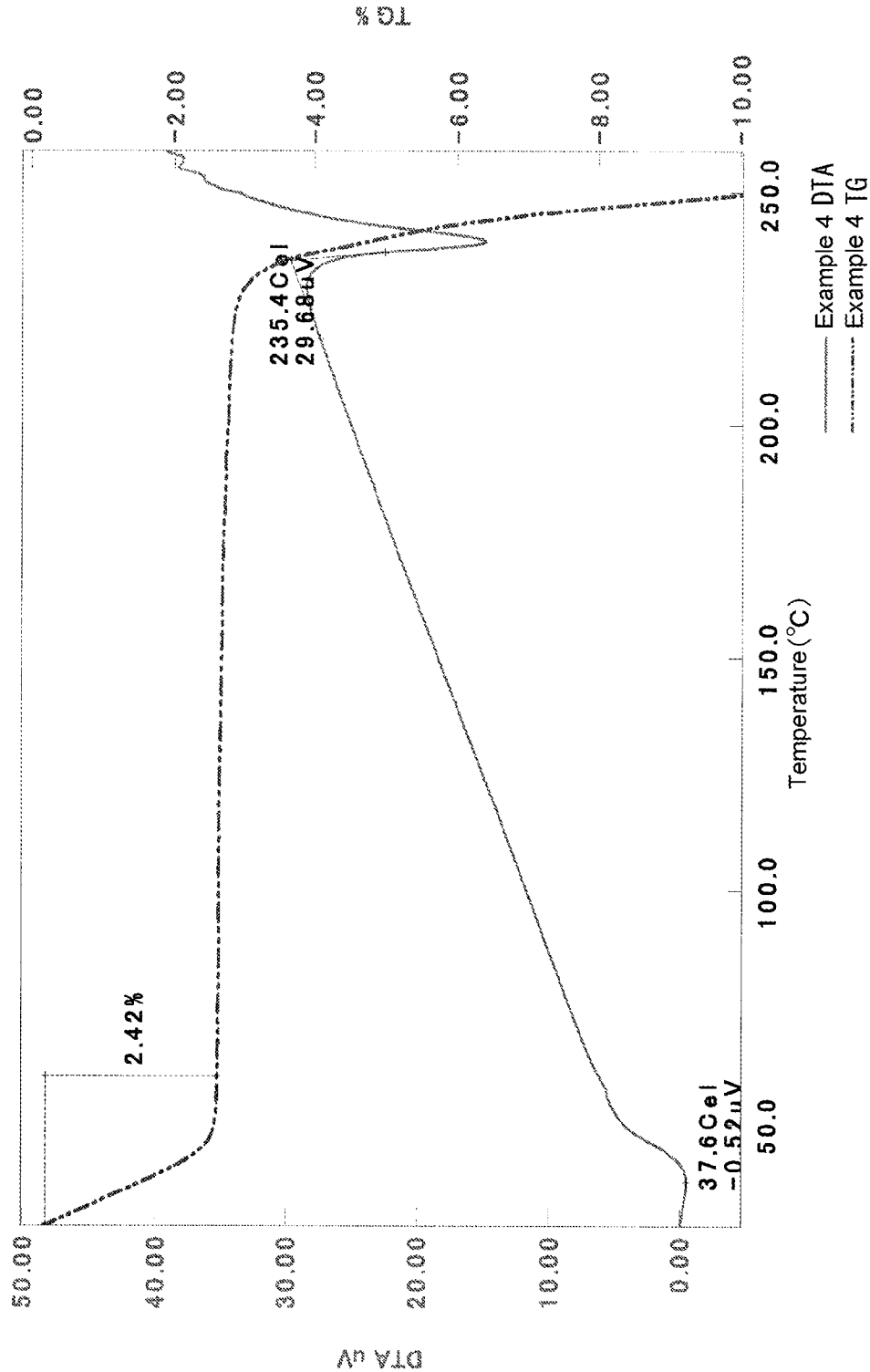
FIG. 15 shows results of TG/DTA analyses of the crystal (form I) of a p-toluenesulfonic acid salt hydrate of the compound (IA) in the present invention.

Results of TG/DTA analysis is shown in FIG. 15. When the rate of weight loss was calculated from this result, the rate was 2.42%. Therefore, it turns out that the crystal contains water corresponding to 1 mole of water.

From the measurement above, it is considered that the Form-I contains water corresponding to 1 to 2 moles of water.

Example 5

Preparation of p-toluenesulfonic acid salt hydrate crystal (form II) of compound (IA)

Tetrahydrofuran (12.5 mL) was added to p-toluenesulfonic acid salts (non-solvate, 5.00 g) synthesized according to Example 1-1 above and the salt was dissolved. N-Propyl acetate (50 mL) was added and stirred at room temperature for 4 hours. The precipitated crystal was collected by filtration, dried at 85° C. for 4 hours in vacuo to give the crystal (4.77 g).

Elemental Analysis:
Calculated: C, 61.56; H, 5.83; N, 7.36; S, 4.21 (calculated as 1.0 H$_2$O).
Measured: C, 61.68; H, 5.78; N, 7.39; S, 4.07
Results of X-ray powder diffraction are shown in FIG. 3 and Table 4.

TABLE 4

| 2θ (°) | d Values (Angstrom) | Intensities Counts | Intensities Relative (%) |
|---|---|---|---|
| 7.1 | 12.36166 | 22.4 | 57.2 |
| 8.8 | 9.99341 | 39.3 | 100 |
| 10.4 | 8.49483 | 13 | 33 |
| 12.0 | 7.37858 | 9.87 | 25.1 |
| 12.6 | 7.01531 | 9.67 | 24.6 |
| 13.1 | 6.75868 | 19 | 48.5 |
| 14.2 | 6.22384 | 20.8 | 53 |
| 14.7 | 6.01666 | 16.3 | 41.4 |
| 15.1 | 5.84703 | 16.8 | 42.7 |
| 15.9 | 5.58662 | 11.6 | 29.6 |
| 16.7 | 5.30339 | 20.4 | 51.8 |
| 17.5 | 5.06428 | 29.2 | 74.3 |

TABLE 4-continued

| 2θ (°) | d Values (Angstrom) | Intensities Counts | Relative (%) |
|---|---|---|---|
| 19.2 | 4.61132 | 24.8 | 63.2 |
| 19.7 | 4.51285 | 23.2 | 59 |
| 21.2 | 4.18505 | 25 | 63.7 |
| 21.9 | 4.05961 | 35.3 | 90 |
| 22.8 | 3.90406 | 18 | 45.9 |
| 23.2 | 3.82606 | 23.9 | 60.9 |
| 23.7 | 3.75472 | 34.1 | 86.7 |
| 24.5 | 3.63203 | 26.4 | 67.2 |
| 25.0 | 3.56143 | 16.4 | 41.9 |
| 26.1 | 3.41231 | 31.7 | 80.6 |
| 26.9 | 3.31075 | 21.5 | 54.7 |
| 27.6 | 3.23119 | 12.6 | 32.1 |
| 28.6 | 3.1235 | 16.8 | 42.9 |
| 29.3 | 3.04533 | 15.4 | 39.2 |
| 29.7 | 3.00109 | 15.7 | 40 |
| 30.9 | 2.89063 | 14.4 | 36.7 |
| 31.9 | 2.79958 | 12 | 30.4 |
| 33.2 | 2.69963 | 13 | 33.1 |
| 35.2 | 2.54534 | 14.6 | 37.2 |
| 37.4 | 2.4003 | 9.45 | 24.1 |
| 37.9 | 2.36958 | 10.9 | 27.8 |

In the X-ray powder diffraction spectrum, peaks were observed at diffraction angles of (2θ): 7.1°±0.2°, 8.8°±0.2°, 17.5°±0.2°, 19.2°±0.2°, 19.7°±0.2°, 21.2°±0.2°, 21.9°±0.2°, 23.7°±0.2°, 24.5°±0.2° and 26.1°±0.2°

Figure 16:
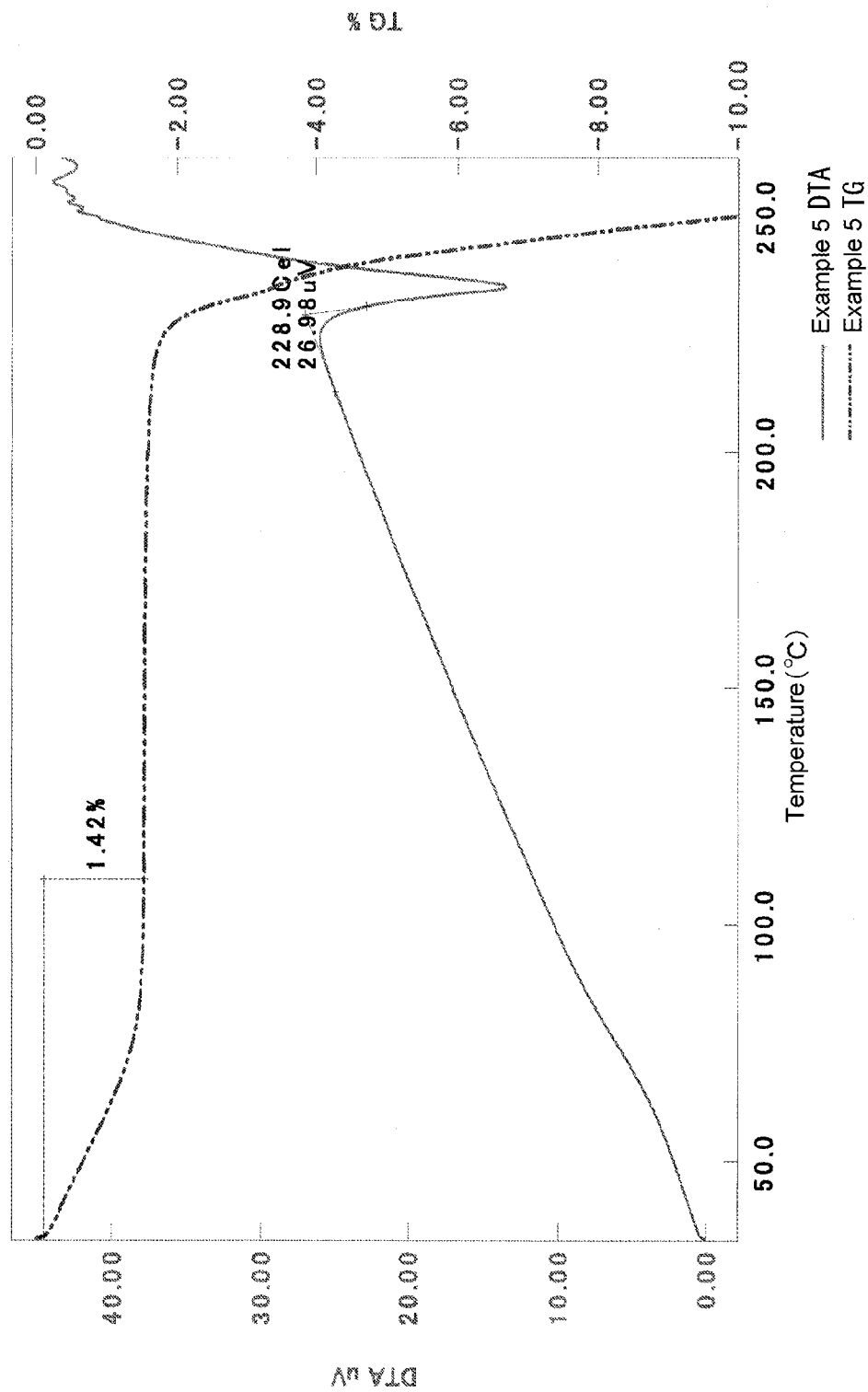
FIG. 16 shows results of TG/DTA analyses of the crystal (form II) of a p-toluenesulfonic acid salt hydrate of the compound (IA) in the present invention.

Result of TG/DTA analysis is shown in FIG. 16. When the rate of weight loss was calculated from this result, the rate was 1.42%. Therefore, it turns out that the crystal contains water corresponding to 0.5 of water.

From measurement above, it is considered that the form II contains water corresponding to 0.5 to 1 of water.

Example 6

Preparation of Acetate of Compound (IA)

Ethyl acetate (100 mL) and an aqueous solution (50 mL) of sodium carbonate (3.18 g; 1.1 equivalent to the p-toluenesulfonic acid salt) was added to p-toluenesulfonic acid salt (non-solvate; 20.0 g) prepared according to Example 1-1 above, and the organic layer was separated. The ethyl acetate layer was washed with 1% aqueous solution of sodium carbonate (50 mL) and saturated brine (50 mL), and each aqueous layer was extracted with ethyl acetate. The ethyl acetate layer was dried over anhydrous sodium sulfate and concentrated to about 30 g. Acetonitrile (200 mL) and acetic acid (4.6 mL; 3 equivalent to the p-toluenesulfonic acid salt), and stirred at room temperature. After observation of a precipitated crystal, the mixture was left stand at room temperature for a day. The precipitate was collected by filtration to give the crystal (16.17 g).

Figure 4:
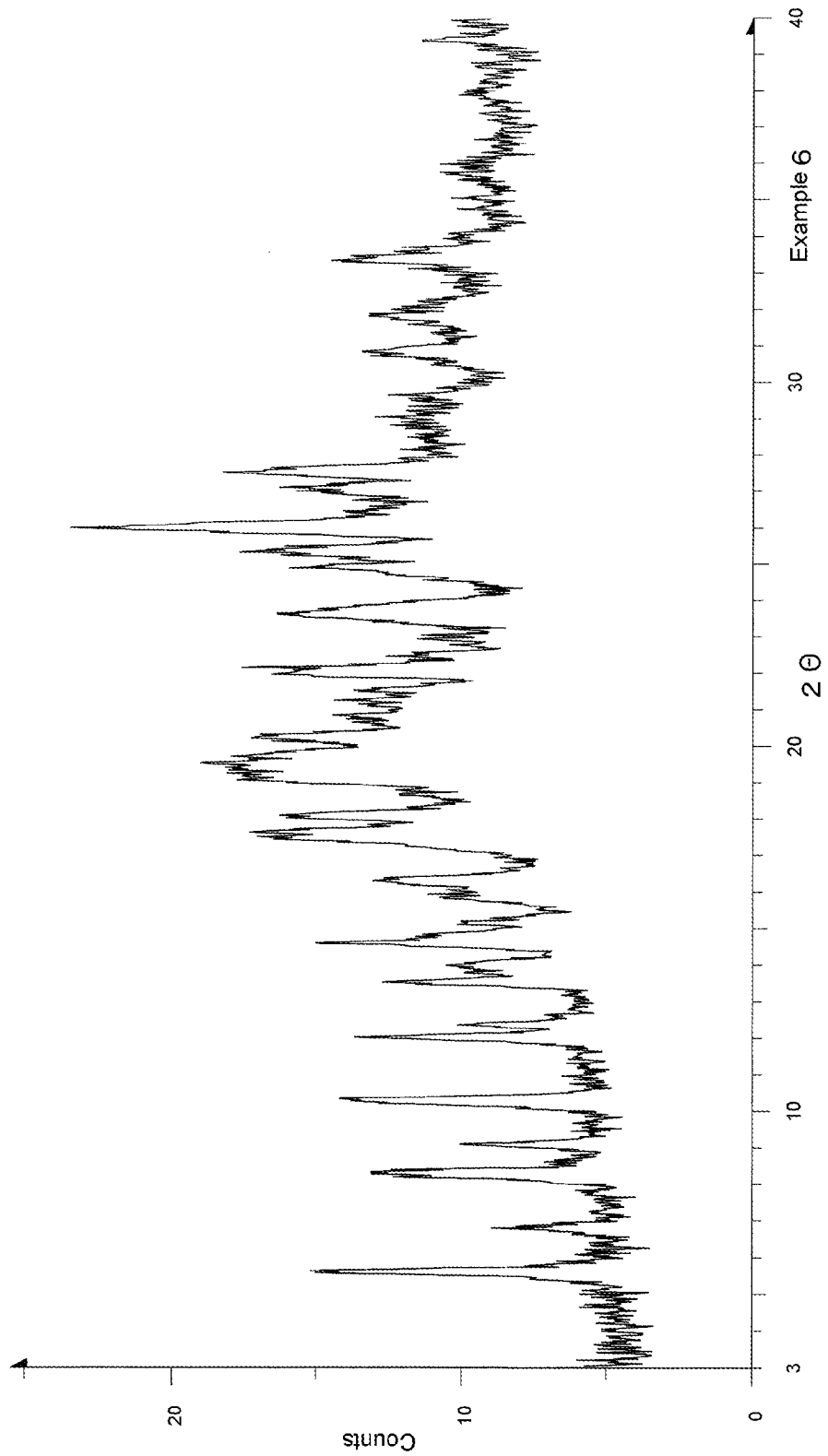
FIG. 4 shows an X-ray-powder-diffraction pattern of the crystal of an acetic acid salt of the compound (IA) in the present invention.

Results of X-ray powder diffraction are shown in FIG. 4 and Table 5.

TABLE 5

| 2θ (°) | d Values (Angstrom) | Intensities Counts | Relative (%) |
|---|---|---|---|
| 5.6 | 15.8238 | 15.2 | 64.6 |
| 6.8 | 13.01374 | 8.94 | 38.1 |
| 8.3 | 10.68609 | 13.1 | 55.7 |
| 9.1 | 9.75071 | 10 | 42.8 |
| 10.3 | 8.61254 | 13.9 | 59.2 |
| 12.0 | 7.37531 | 13.6 | 58.1 |

TABLE 5-continued

| 2θ (°) | d Values (Angstrom) | Intensities Counts | Relative (%) |
|---|---|---|---|
| 12.3 | 7.16833 | 10.1 | 43.1 |
| 13.5 | 6.55055 | 12.7 | 54.1 |
| 14.0 | 6.3369 | 10.5 | 44.8 |
| 14.6 | 6.06901 | 15 | 63.9 |
| 15.8 | 5.58825 | 10.7 | 45.8 |
| 16.3 | 5.43234 | 13 | 55.3 |
| 17.5 | 5.05184 | 16.1 | 68.5 |
| 18.1 | 4.90501 | 16.2 | 69.2 |
| 19.1 | 4.6427 | 17.4 | 74 |
| 20.2 | 4.38516 | 17.1 | 72.8 |
| 22.0 | 4.04154 | 16.5 | 70.4 |
| 23.6 | 3.76632 | 16.3 | 69.6 |
| 24.9 | 3.56788 | 15.1 | 64.5 |
| 25.4 | 3.50782 | 17.7 | 75.2 |
| 26.0 | 3.42322 | 23.5 | 100 |
| 27.1 | 3.28776 | 16.2 | 69.2 |
| 27.5 | 3.23704 | 18.2 | 77.7 |
| 30.8 | 2.89686 | 13.4 | 57 |
| 33.4 | 2.68159 | 14.4 | 61.5 |

In the X-ray powder diffraction spectrum, peaks were observed at diffraction angles of (2θ): 5.6°±0.2°, 8.3°±0.2°, 9.1°±0.2°, 10.3°±0.2°, 12.0°±0.2°, 13.5°±0.2°, 14.6°±0.2°, 16.3°±0.2° and 26.0°±0.2°.

Figure 17:
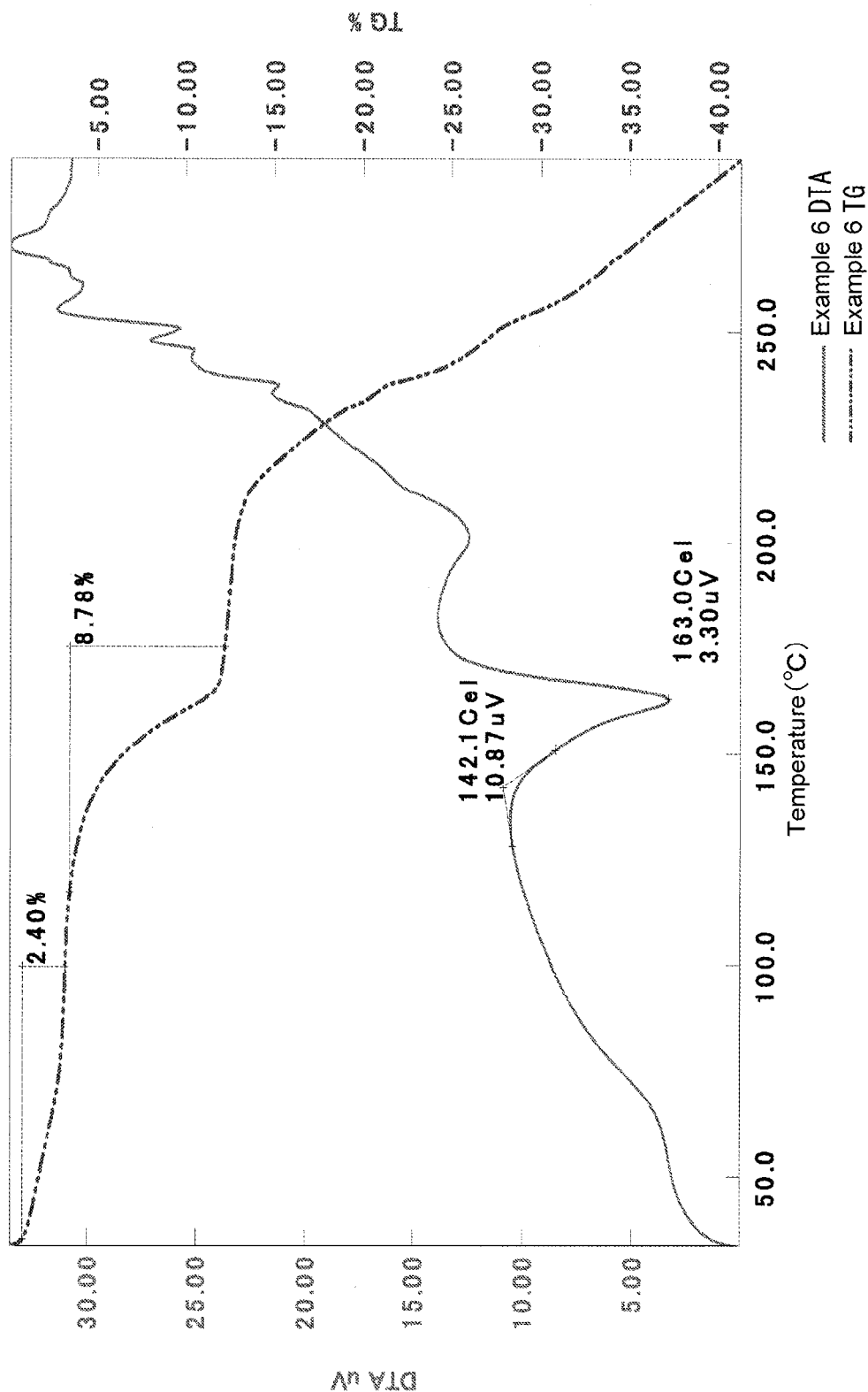
FIG. 17 shows results of TG/DTA analyses of an acetic acid salt of the compound (IA) in the present invention.

Results of TG/DTA analysis are shown in FIG. 17.

Example 7

Preparation of Hydrochloride Salt of Compound (IA)

Ethyl acetate (100 mL) and an aqueous solution (50 mL) of sodium carbonate (3.18 g; 1.1 equivalent to the p-toluenesulfonic acid salt) was added to p-toluenesulfonic acid salt (non-solvate; 20.0 g) prepared according to Example 1-1 above, and the organic layer was separated. The ethyl acetate layer was washed with water (50 mL) twice and each aqueous layer was extracted with ethyl acetate. The ethyl acetate layer was dried over anhydrous sodium sulfate, acetonitrile (200 mL) and 4 mol/L hydrochloric acid-ethyl acetate (10 mL; 1.5 equivalents to the p-toluenesulfonic acid salt) and concentrated to about 50 g. Acetonitrile (200 mL) was added to the concentrated solution, and stirred at room temperature for one hour. The precipitate was collected by filtration to give the crystal (10.01 g).

Figure 5:
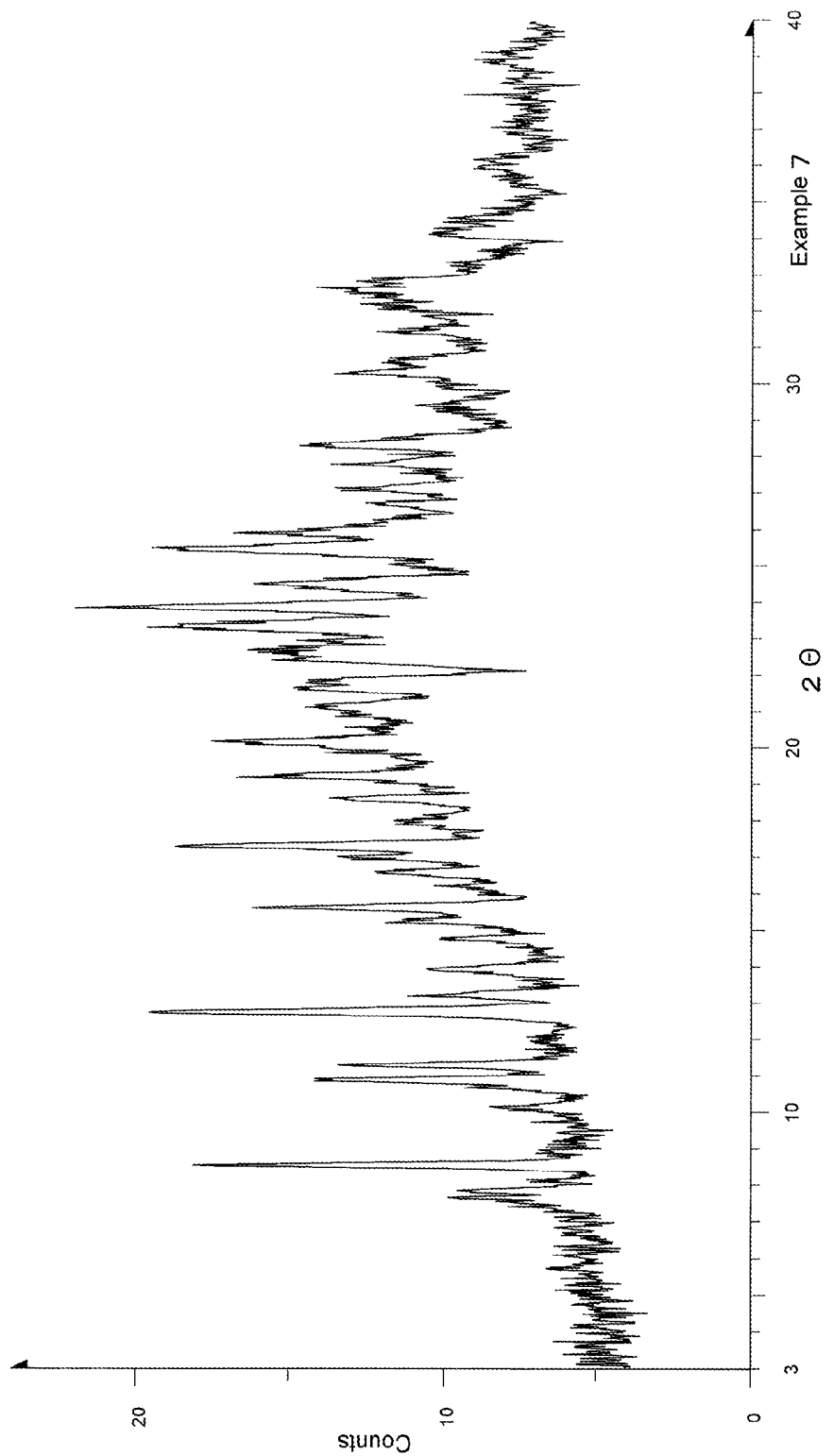
FIG. 5 shows an X-ray-powder-diffraction pattern of the crystal of a hydrochloric acid salt of the compound (IA) in the present invention.

Results of X-ray powder diffraction are shown in FIG. 5 and Table 6.

TABLE 6

| 2θ (°) | d Values (Angstrom) | Intensities Counts | Relative (%) |
|---|---|---|---|
| 8.5 | 10.37185 | 18.1 | 82.5 |
| 10.1 | 8.75954 | 8.12 | 36.9 |
| 10.8 | 8.15617 | 14.1 | 64.2 |
| 11.3 | 7.85594 | 13.4 | 61 |
| 12.7 | 6.94656 | 19.6 | 89 |
| 13.2 | 6.71037 | 11.2 | 50.8 |
| 13.9 | 6.36349 | 10.5 | 47.9 |
| 14.7 | 6.00754 | 10.1 | 45.9 |
| 15.2 | 5.82004 | 11.3 | 51.6 |
| 15.6 | 5.67944 | 16.2 | 73.6 |
| 16.6 | 5.34696 | 12.1 | 55.2 |
| 17.0 | 5.22329 | 13.3 | 60.4 |
| 17.3 | 5.12379 | 18.7 | 85.2 |
| 17.9 | 4.94131 | 11.3 | 51.3 |
| 18.6 | 4.76981 | 13.6 | 62.1 |

TABLE 6-continued

| 2θ (°) | d Values (Angstrom) | Intensities Counts | Relative (%) |
|---|---|---|---|
| 19.2 | 4.61847 | 16.6 | 75.5 |
| 20.1 | 4.40498 | 17.6 | 79.8 |
| 21.1 | 4.20269 | 14.4 | 65.6 |
| 21.6 | 4.10942 | 14.7 | 66.8 |
| 21.8 | 4.06819 | 14.2 | 64.7 |
| 22.4 | 3.96116 | 15.5 | 70.7 |
| 23.3 | 3.81325 | 19.6 | 89.3 |
| 23.9 | 3.7278 | 22 | 100 |
| 24.5 | 3.63268 | 16.1 | 73.1 |
| 25.5 | 3.49582 | 18.6 | 84.6 |
| 25.9 | 3.43649 | 16.8 | 76.4 |
| 26.7 | 3.33784 | 12.2 | 55.5 |
| 27.1 | 3.28707 | 13.2 | 59.9 |
| 27.8 | 3.20884 | 13.6 | 62 |
| 28.3 | 3.14897 | 14.6 | 66.6 |
| 30.3 | 2.9465 | 13.5 | 61.4 |
| 34.1 | 2.62528 | 10.5 | 47.7 |

In the X-ray powder diffraction spectrum, peaks were observed at diffraction angles of (2θ): 8.5°±0.2°, 10.8°±0.2°, 11.3°±0.2°, 12.7°±0.2°, 13.9°±0.2°, 15.6°±0.2°, 17.3°±0.2°, 19.2°±0.2°, 20.1°±0.2° and 23.9°±0.2°.

Figure 18:
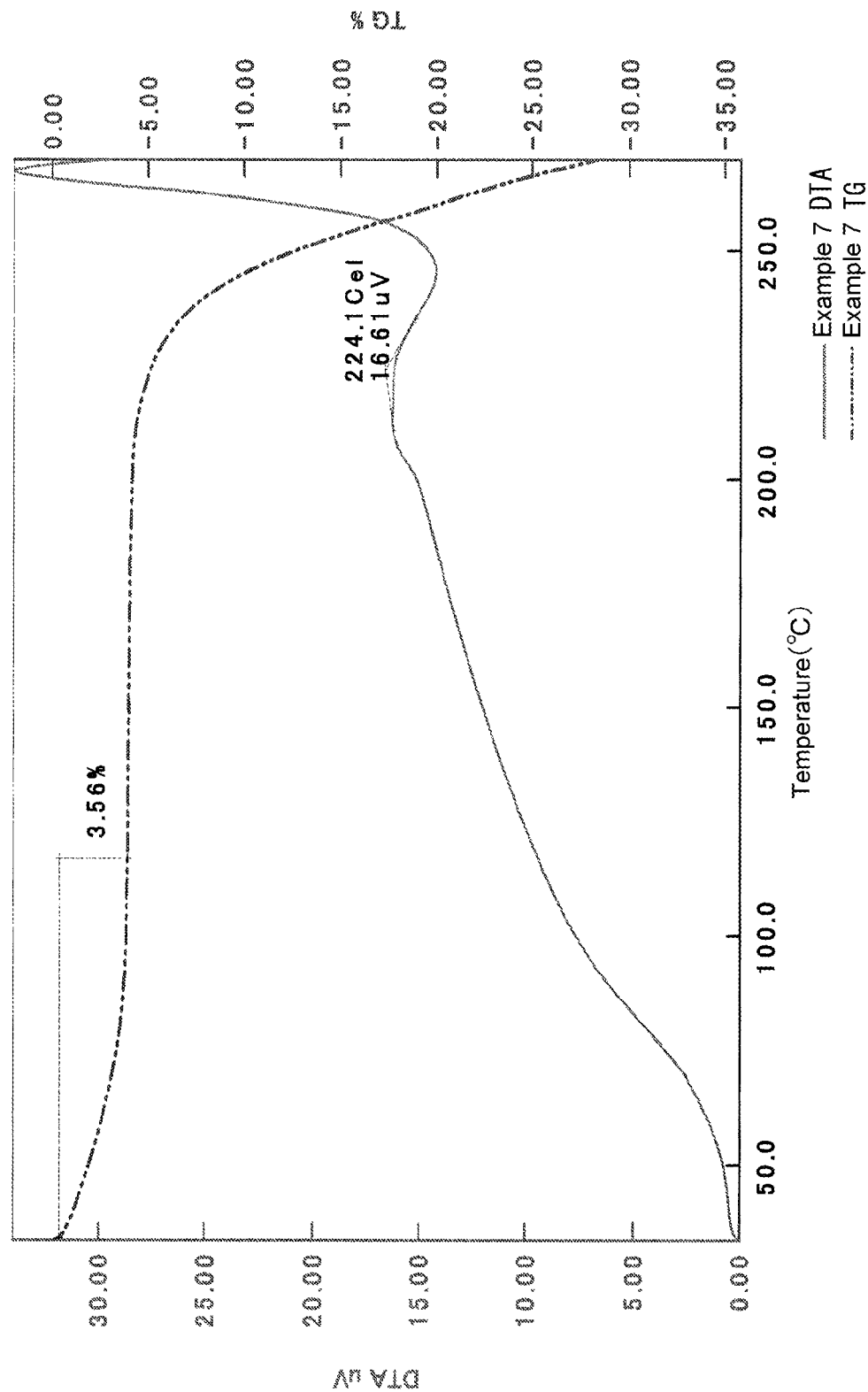
FIG. 18 shows results of TG/DTA analyses of a hydrochloric acid salt of the compound (IA) in the present invention.

Results of TG/DTA analysis are shown in FIG. 18.

Example 8

Preparation of Ethanol Solvate of Compound (IA)

Ethyl acetate (100 mL) and an aqueous solution (50 mL) of sodium carbonate (3.18 g; 1.1 equivalent to the p-toluenesulfonic acid salt) was added to p-toluenesulfonic acid salt (non-solvate; 20.0 g) prepared according to Example 1-1 above, and the organic layer was separated. The ethyl acetate layer was washed with 1% aqueous solution of sodium carbonate (50 mL) and saturated brine (50 mL), and each aqueous layer was extracted with ethyl acetate (50 mL). The ethyl acetate layer was dried over anhydrous sodium sulfate and concentrated to about 30 g. Ethanol (100 mL) was added and diluted with isopropyl ether to the extent just before the solution became cloudy. The mixture was stirred at room temperature and the mixture was left stand at room temperature for a day, after observation of a precipitated crystal. The precipitate was collected by filtration to give the crystal (9.57 g).

Figure 6:
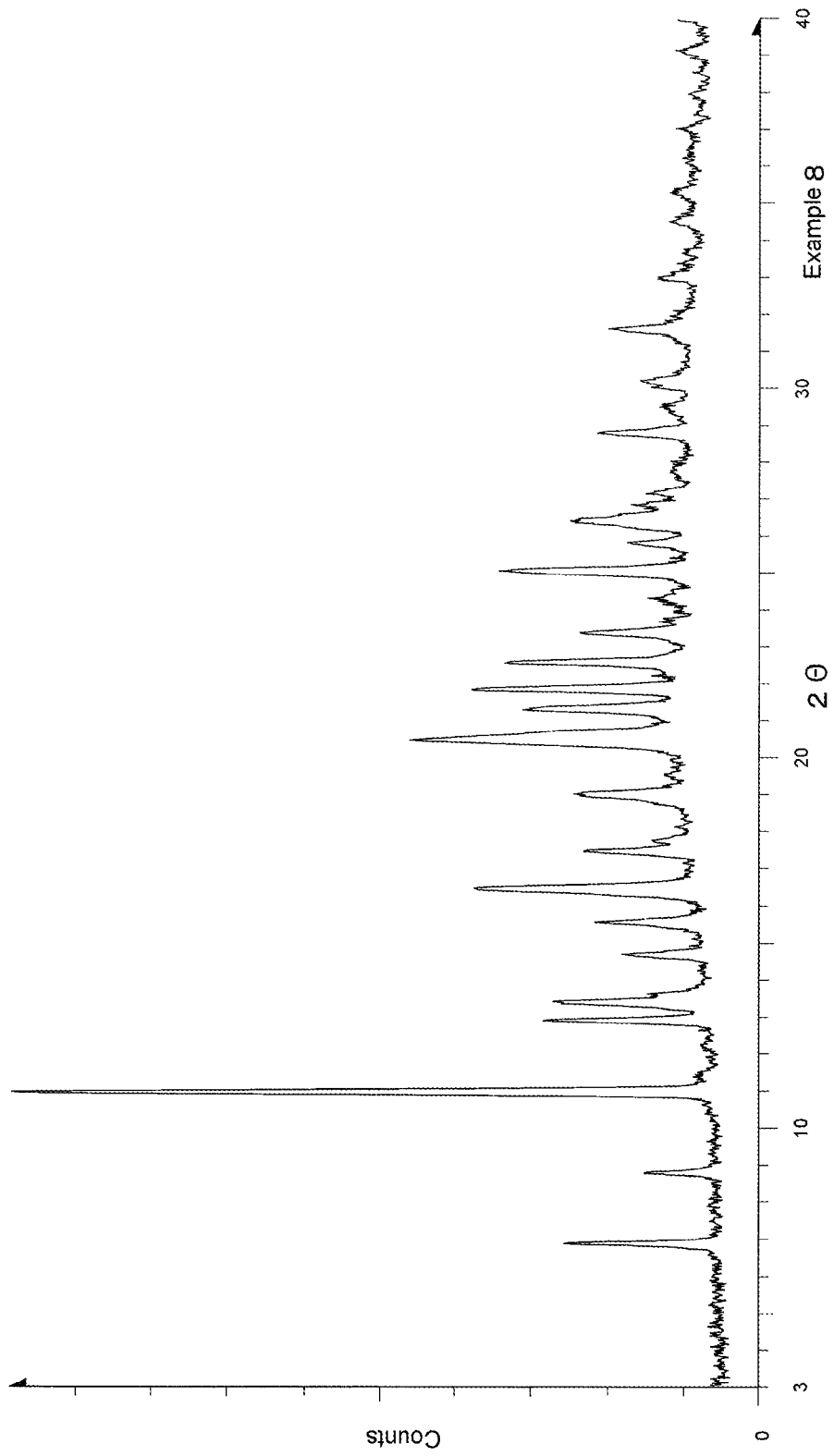
FIG. 6 shows an X-ray-powder-diffraction pattern of the crystal of an ethanol solvate of the compound (IA) in the present invention.

Results of X-ray powder diffraction are shown in FIG. 6 and Table 7.

TABLE 7

| 2θ (°) | d Values (Angstrom) | Intensities Counts | Relative (%) |
|---|---|---|---|
| 6.9 | 12.88317 | 25.6 | 25.9 |
| 8.8 | 10.08288 | 15 | 15.2 |
| 11.0 | 8.06776 | 98.6 | 100 |
| 12.9 | 6.85907 | 28.4 | 28.8 |
| 13.4 | 6.60972 | 27.1 | 27.4 |
| 14.7 | 6.03149 | 18.1 | 18.3 |
| 15.5 | 5.69466 | 21.5 | 21.8 |
| 16.5 | 5.38347 | 37.4 | 37.9 |
| 17.5 | 5.0717 | 23.1 | 23.4 |
| 19.0 | 4.66874 | 24.3 | 24.6 |
| 20.5 | 4.33421 | 46 | 46.6 |
| 21.3 | 4.16275 | 31 | 31.4 |
| 21.8 | 4.06452 | 37.7 | 38.2 |
| 22.6 | 3.93342 | 33.3 | 33.7 |
| 23.4 | 3.80278 | 23.6 | 24 |

TABLE 7-continued

| 2θ (°) | d Values (Angstrom) | Intensities Counts | Relative (%) |
|---|---|---|---|
| 24.3 | 3.65768 | 14.6 | 14.8 |
| 25.1 | 3.54908 | 34.1 | 34.6 |
| 25.8 | 3.44888 | 17.3 | 17.6 |
| 26.4 | 3.36859 | 24.8 | 25.1 |
| 26.8 | 3.31821 | 16.9 | 17.2 |
| 27.2 | 3.27656 | 14 | 14.2 |
| 28.8 | 3.09654 | 21.3 | 21.6 |
| 29.5 | 3.02253 | 13.1 | 13.3 |
| 30.2 | 2.95473 | 15.7 | 16 |
| 31.6 | 2.82668 | 19.9 | 20.1 |
| 33.0 | 2.7121 | 13.3 | 13.5 |
| 34.6 | 2.59354 | 11.8 | 12 |
| 35.3 | 2.53809 | 11.8 | 12 |
| 39.2 | 2.29883 | 11.1 | 11.2 |

In the X-ray powder diffraction spectrum, peaks were observed at diffraction angles of (2θ): 6.9°±0.2°, 11.0°±0.2°, 12.9°±0.2°, 13.4°±0.2°, 16.5°±0.2°, 20.5°±0.2°, 21.3°±0.2°, 21.8°±0.2°, 22.6°±0.2° and 25.1°±0.2°.

Figure 19:
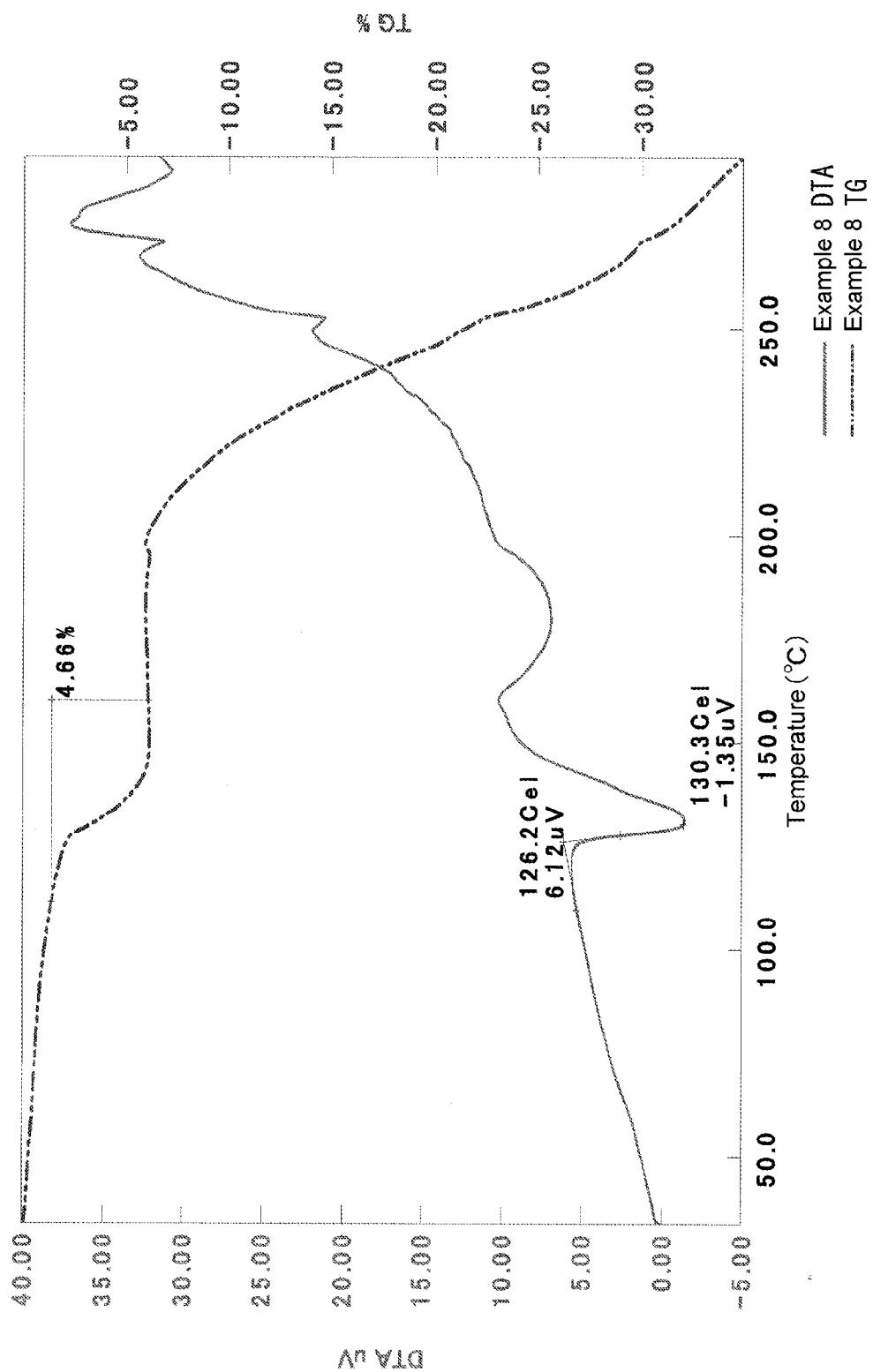
FIG. 19 shows results of TG/DTA analyses of an ethanol solvate of the compound (IA) in the present invention.

Results of TG/DTA analysis are shown in FIG. 19.

Example 9

Preparation of a Free Form of Compound (IA)

An ethanol solvate of Example 8 was dried at 120° C. for 10 hours in vacuo, and it was confirmed that ethanol did not remain in the crystal with NMR.

Figure 7:
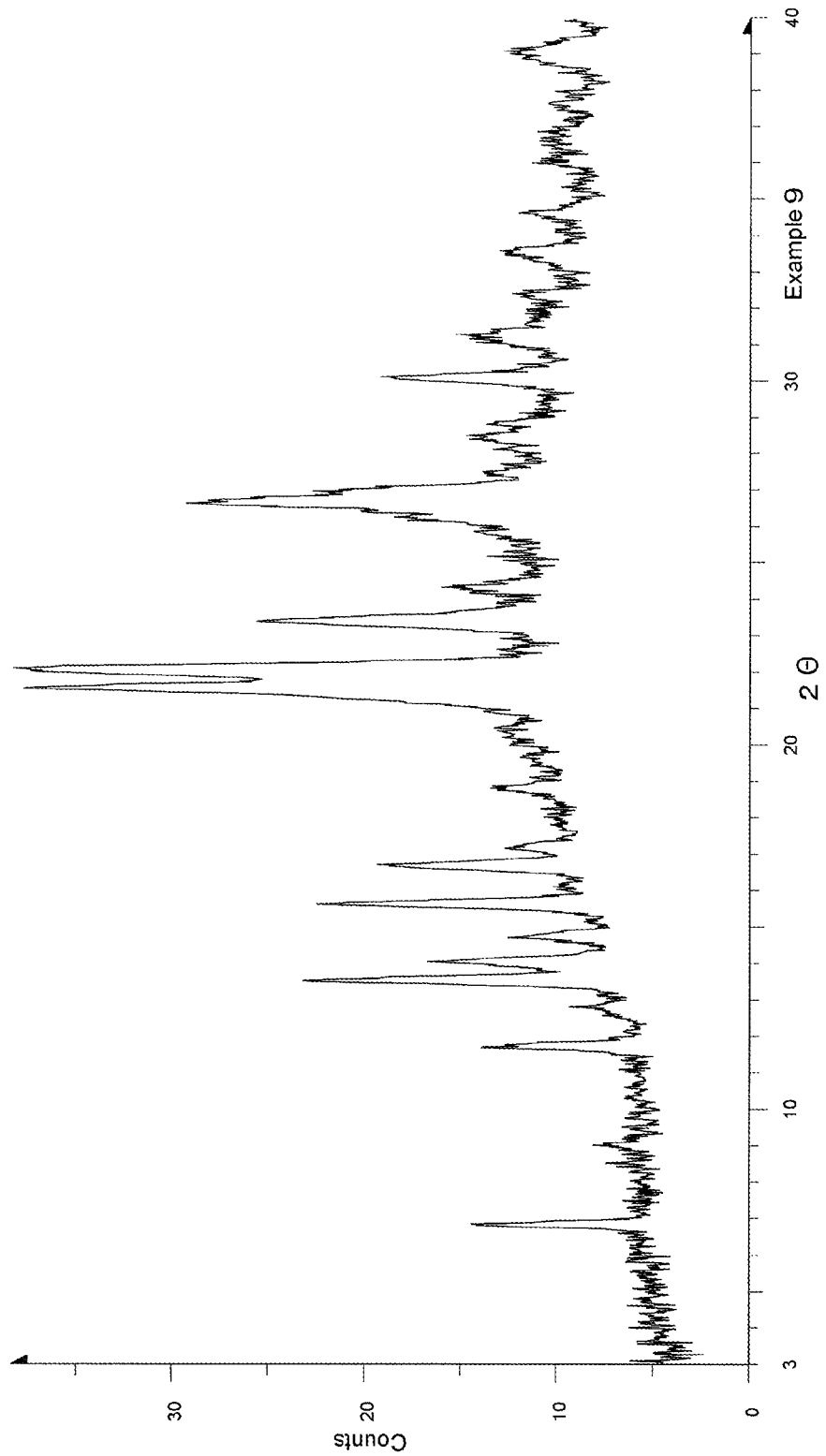
FIG. 7 shows an X-ray-powder-diffraction pattern of the crystal of a free compound (IA) in the present invention.

Results of X-ray powder diffraction are shown in FIG. 7 and Table 8.

TABLE 8

| 2θ (°) | d Values (Angstrom) | Intensities Counts | Relative (%) |
|---|---|---|---|
| 6.8 | 13.00131 | 14.3 | 37.4 |
| 11.7 | 7.55261 | 13.7 | 35.8 |
| 13.5 | 6.54867 | 23.2 | 60.4 |
| 14.0 | 6.30642 | 16.7 | 43.6 |
| 14.7 | 6.01747 | 12.4 | 32.4 |
| 15.6 | 5.67359 | 22.4 | 58.5 |
| 16.7 | 5.31296 | 19.3 | 50.4 |
| 17.2 | 5.16214 | 12.6 | 32.9 |
| 18.8 | 4.71724 | 13.4 | 34.9 |
| 21.6 | 4.11767 | 37.8 | 98.5 |
| 22.1 | 4.02382 | 38.3 | 100 |
| 23.4 | 3.80076 | 25.6 | 66.7 |
| 24.3 | 3.65724 | 16 | 41.7 |
| 26.7 | 3.3421 | 29.3 | 76.4 |
| 27.0 | 3.29962 | 21.3 | 55.7 |
| 30.1 | 2.96564 | 18.6 | 48.6 |
| 31.2 | 2.86065 | 14.6 | 38 |
| 32.4 | 2.76133 | 12.3 | 32 |
| 33.6 | 2.667 | 12.9 | 33.7 |

In the X-ray powder diffraction spectrum, peaks were observed at diffraction angles of (2θ): 6.8°±0.2°, 11.7°±0.2°, 13.5°±0.2°, 15.6°±0.2°, 16.7°±0.2°, 21.6°±0.2°, 22.1°±0.2°, 23.4°±0.2°, 26.7°±0.2° and 30.1°±0.2°.

Figure 20:
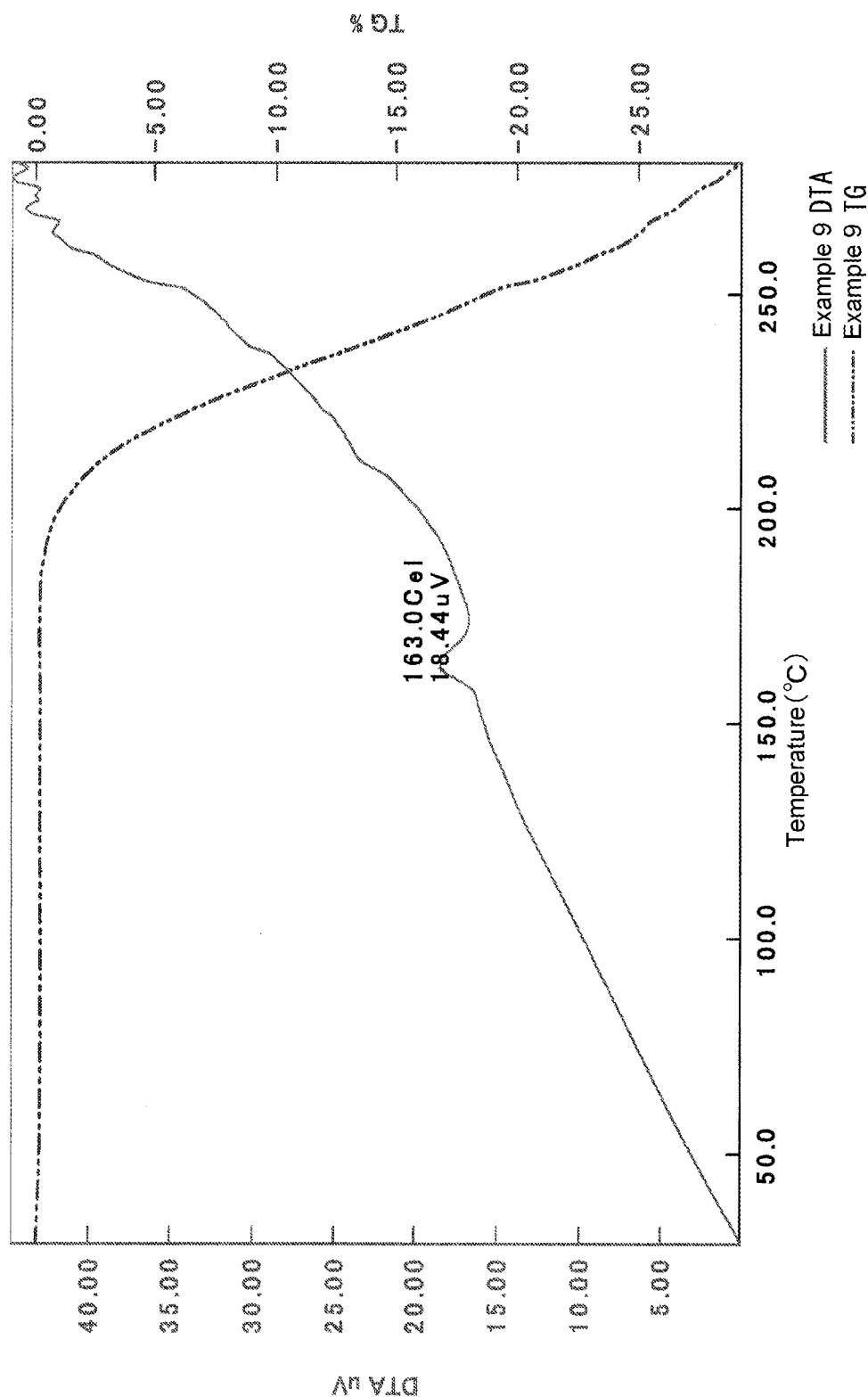
FIG. 20 shows results of TG/DTA analyses of a free form of the compound (IA) in the present invention.

Results of TG/DTA analysis are shown in FIG. 20.

Example 10

Preparation of methyl acetate solvate of p-toluenesulfonic acid salt of compound (IA)

A mixture of 2-propanol (5 mL)-water (0.5 mL) was added to p-toluenesulfonic acid salt (non-solvate; 1.0 g) prepared according to Example 1-1 above, and dissolved it by warming. Methyl acetate (20 mL) was added and stirred at room temperature for 4 hours. The precipitate was collected by filtration to give the crystal (0.98 g).

Figure 8:
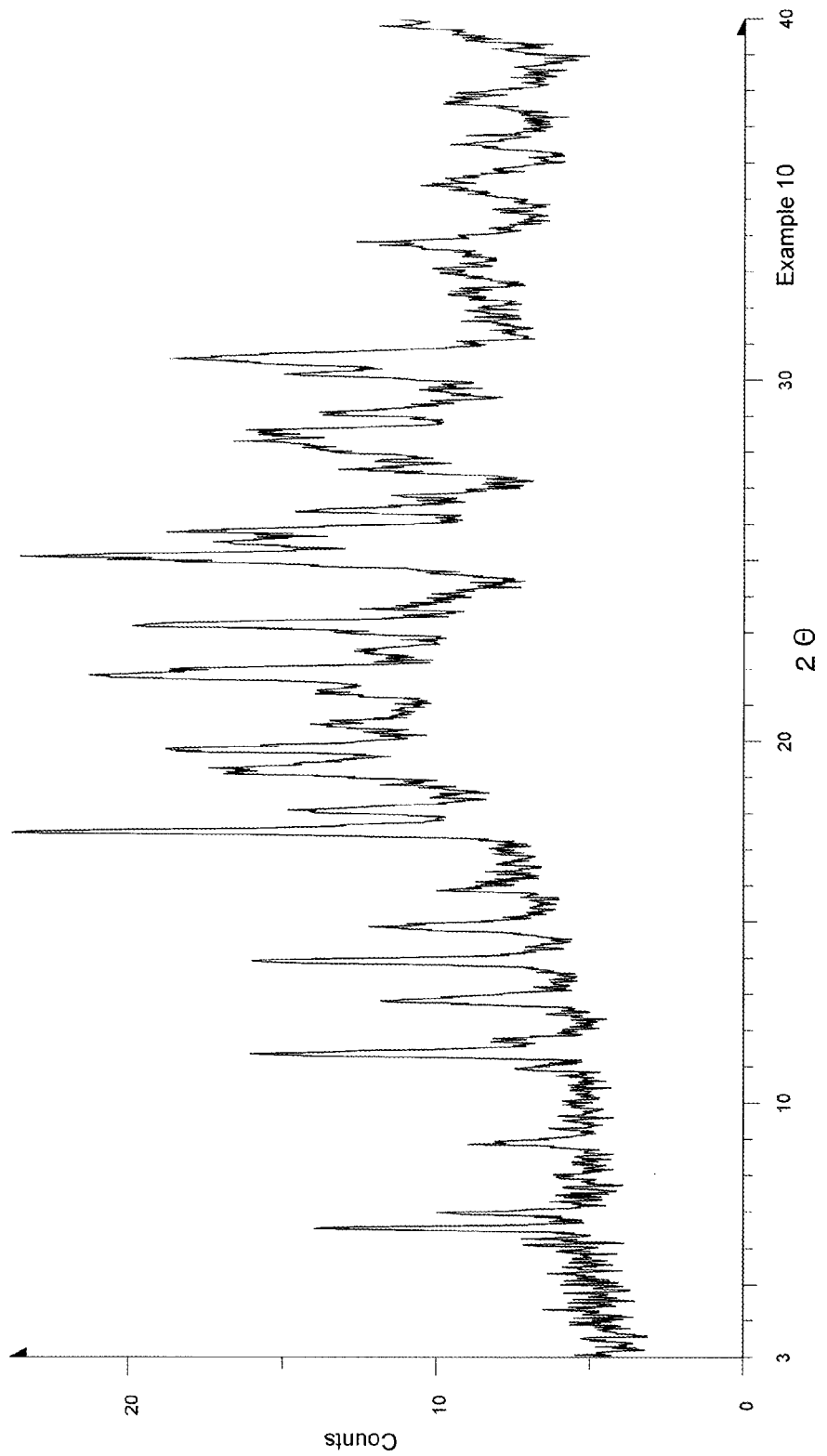
FIG. 8 shows an X-ray-powder-diffraction pattern of the crystal of methyl acetate solvate of a p-toluenesulfonic acid salt of the compound (IA) in the present invention.

Results of X-ray powder diffraction are shown in FIG. 8 and Table 9.

TABLE 9

| 2θ (°) | d Values (Angstrom) | Intensities Counts | Relative (%) |
|---|---|---|---|
| 6.5 | 13.55499 | 14 | 58.5 |
| 6.9 | 12.7548 | 9.94 | 41.6 |
| 8.9 | 9.97048 | 8.71 | 36.5 |
| 10.9 | 8.088 | 7.4 | 31 |
| 11.3 | 7.81057 | 16.1 | 67.3 |
| 12.8 | 6.91511 | 11.8 | 49.5 |
| 13.9 | 6.36968 | 16 | 67.2 |
| 14.8 | 5.96698 | 12.2 | 51.2 |
| 15.9 | 5.58198 | 9.96 | 41.7 |
| 17.5 | 5.06821 | 23.9 | 100 |
| 18.1 | 4.90561 | 14.9 | 62.3 |
| 19.2 | 4.62483 | 16.6 | 69.4 |
| 19.8 | 4.48926 | 18.8 | 78.7 |
| 20.5 | 4.33853 | 14.1 | 59.1 |
| 21.8 | 4.07377 | 21.3 | 89.3 |
| 23.2 | 3.82827 | 19.5 | 81.7 |
| 25.1 | 3.54418 | 23.6 | 98.9 |
| 25.8 | 3.44755 | 18.1 | 75.8 |
| 26.4 | 3.37644 | 14.6 | 61.2 |
| 26.8 | 3.32745 | 11.3 | 47.2 |
| 27.5 | 3.23717 | 13.2 | 55.3 |
| 28.6 | 3.12329 | 15.8 | 66.3 |
| 29.1 | 3.06669 | 13.8 | 57.9 |
| 30.2 | 2.95871 | 15 | 62.7 |
| 30.6 | 2.91807 | 18.7 | 78.3 |
| 32.4 | 2.76048 | 9.61 | 40.3 |
| 33.8 | 2.64979 | 11.3 | 47.3 |
| 36.5 | 2.4573 | 9.53 | 39.9 |

In the X-ray powder diffraction spectrum, peaks were observed at diffraction angles of (2θ): 17.5°±0.2°, 21.8°±0.2°, 23.2°±0.2°, 25.1°±0.2° and 30.6°±0.2°.

Figure 21:
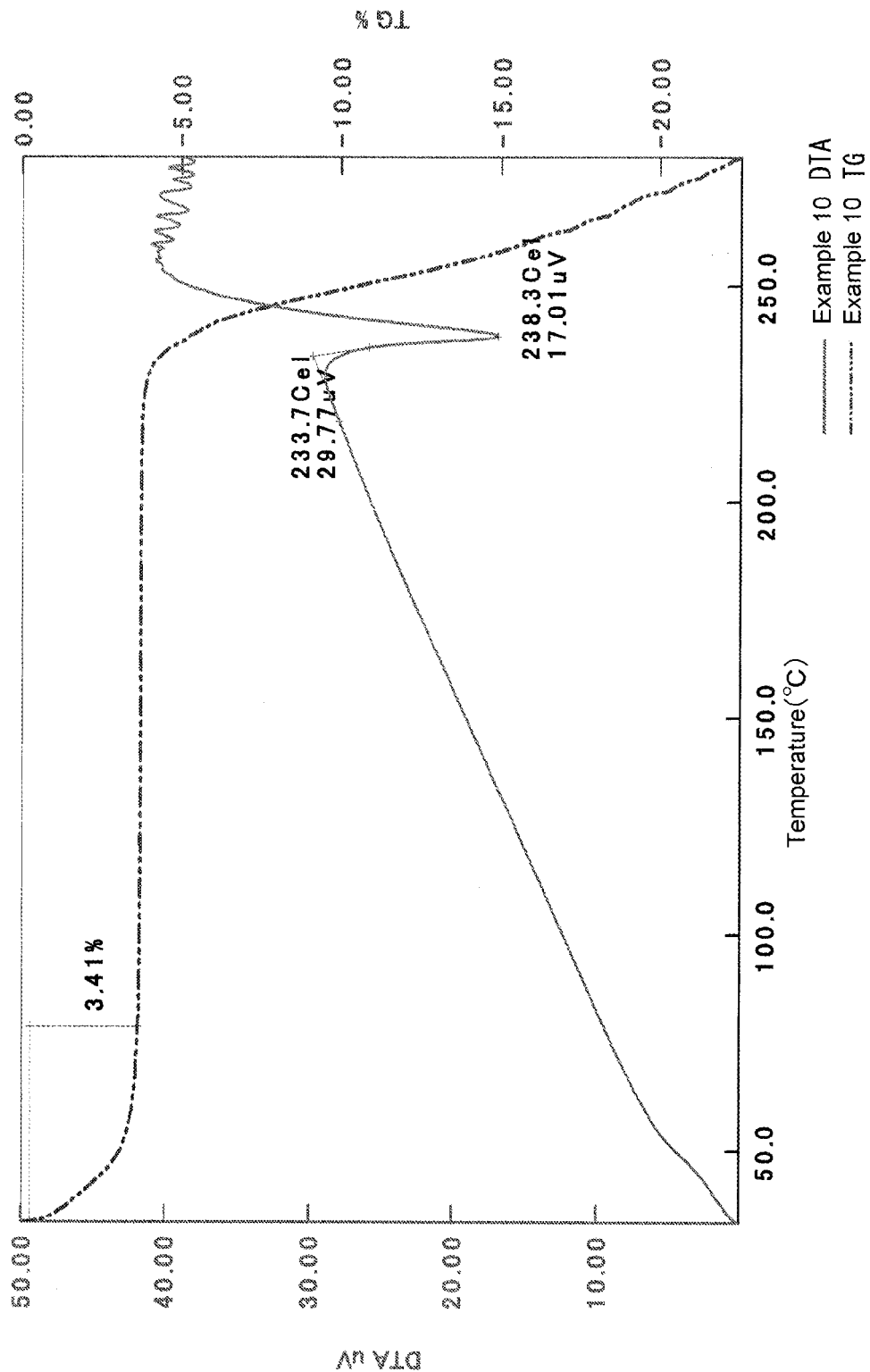
FIG. 21 shows results of TG/DTA analyses of methyl acetate solvate of a p-toluenesulfonic acid salt of the compound (IA) in the present invention.

Results of TG/DTA analysis are shown in FIG. 21.

Example 11

Preparation of ethyl acetate/2-propanol solvate of p-toluenesulfonic acid salt of compound (IA)

A mixture of 2-propanol (5 mL)-water (0.5 mL) was added to p-toluenesulfonic acid salt (non-solvate; 1.0 g) prepared according to Example 1-1 above, and dissolved it by warming. Ethyl acetate (20 mL) was added and stirred at room temperature for 4 hours. The precipitate was collected by filtration to give the crystal (0.96 g).

Figure 9:
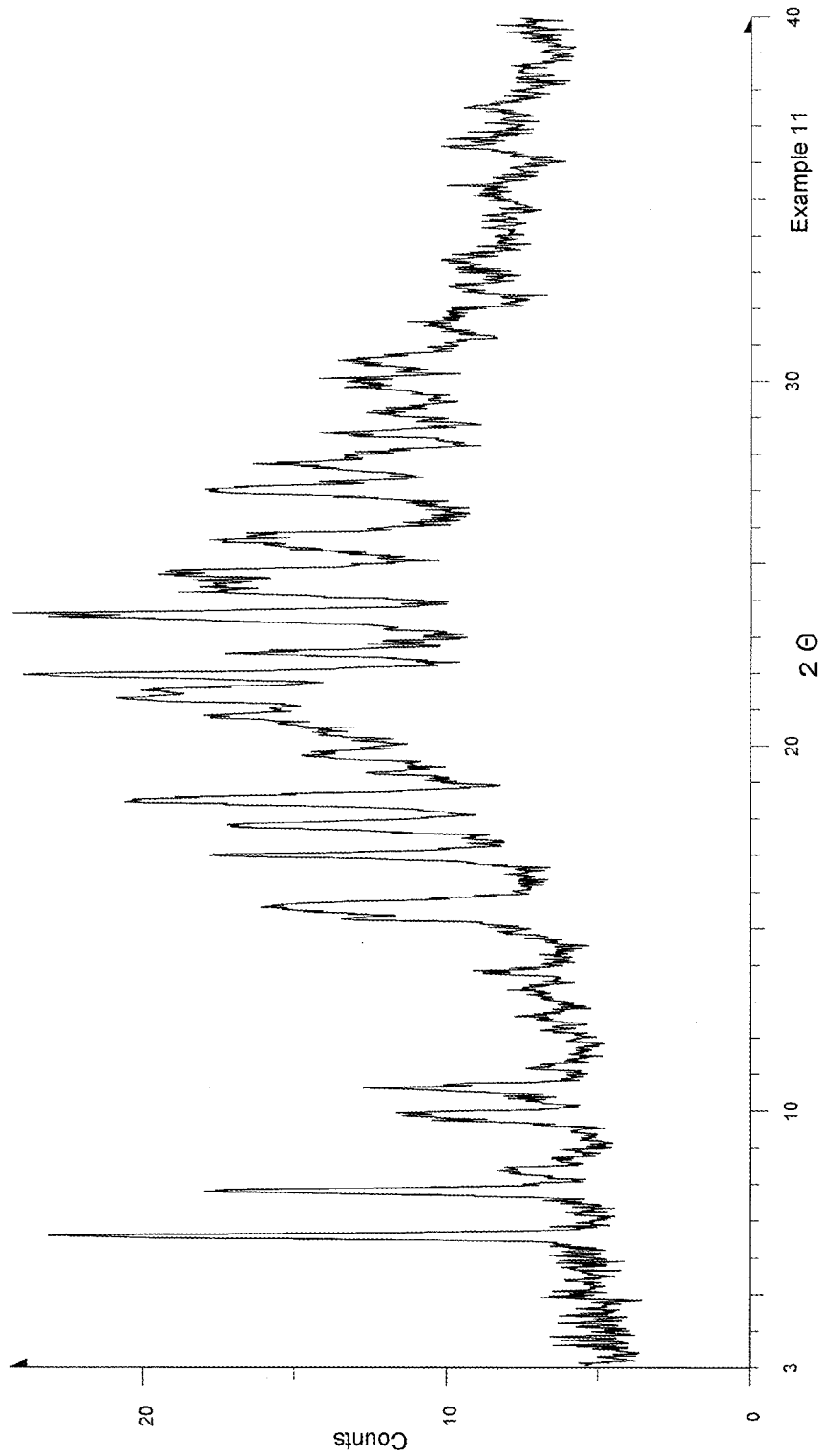
FIG. 9 shows an X-ray-powder-diffraction pattern of the crystal of (ethyl acetate and 2-propanol) solvate of a p-toluenesulfonic acid salt of the compound (IA) in the present invention.

Results of X-ray powder diffraction are shown in FIG. 9 and Table 10.

TABLE 10

| 2θ (°) | d Values (Angstrom) | Intensities Counts | Relative (%) |
|---|---|---|---|
| 6.6 | 13.47309 | 23.2 | 96.6 |
| 7.8 | 11.34686 | 18 | 74.8 |
| 8.4 | 10.58018 | 8.27 | 34.5 |
| 9.9 | 8.9521 | 11.2 | 46.6 |
| 10.6 | 8.34844 | 12.8 | 53.2 |
| 13.8 | 6.41281 | 9.07 | 37.8 |
| 15.3 | 5.79383 | 13.2 | 55.2 |

TABLE 10-continued

| 2θ (°) | d Values (Angstrom) | Intensities Counts | Relative (%) |
|---|---|---|---|
| 15.6 | 5.6827 | 16.1 | 67.2 |
| 17.0 | 5.21242 | 17.8 | 74.2 |
| 17.8 | 4.97656 | 17.2 | 71.8 |
| 18.5 | 4.79584 | 20.6 | 85.7 |
| 19.7 | 4.49407 | 14.8 | 61.7 |
| 21.3 | 4.16711 | 20.9 | 87.2 |
| 21.9 | 4.04613 | 24 | 100 |
| 22.6 | 3.93928 | 17.3 | 72 |
| 23.6 | 3.76603 | 23.3 | 97.3 |
| 24.3 | 3.66665 | 17.5 | 73 |
| 24.7 | 3.59459 | 18.8 | 78.2 |
| 25.6 | 3.47477 | 17.8 | 74.2 |
| 27.0 | 3.29714 | 18 | 74.9 |
| 27.7 | 3.21505 | 16.4 | 68.2 |
| 28.6 | 3.12129 | 14.2 | 59.3 |
| 29.1 | 3.06326 | 12.7 | 52.8 |
| 30.6 | 2.92311 | 13.6 | 56.7 |

In the X-ray powder diffraction spectrum, peaks were observed at diffraction angles of (2θ): 6.6°±0.2°, 7.8°±0.2°, 17.0"±0.2°, 17.8°±0.2°, 18.5°±0.2°, 21.9°±0.2° and 23.6°±0.2°.

Figure 22:
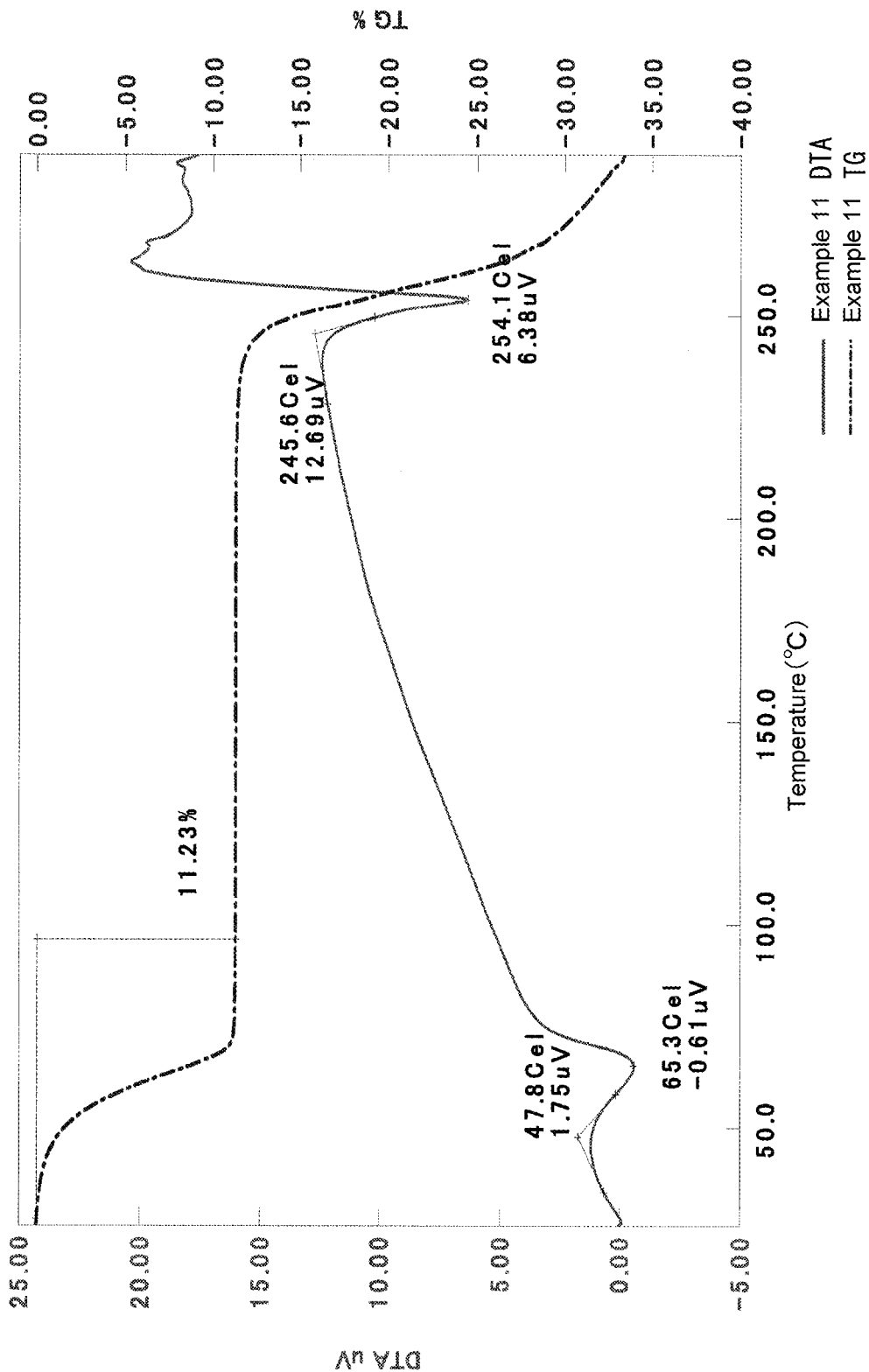
FIG. 22 shows results of TG/DTA analyses of ethyl acetate/2-propanol solvate of a p-toluenesulfonic acid salt of the compound (IA) in the present invention.

Results of TG/DTA analysis are shown in FIG. 22.

Example 12

Preparation of n-propyl acetate/2-propanol solvate of p-toluenesulfonic acid salt of compound (IA)

Figure 10:
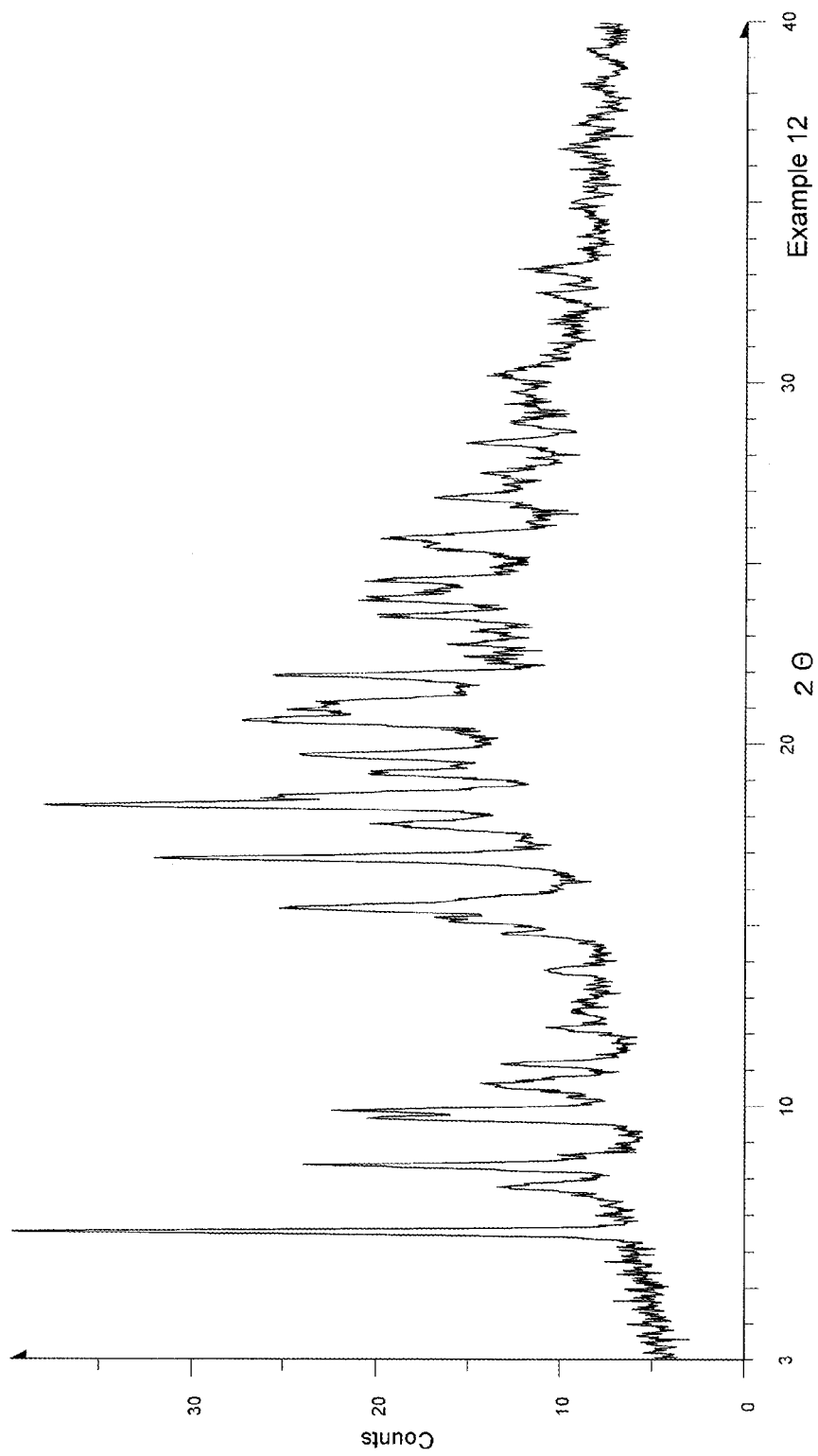
FIG. 10 shows an X-ray-powder-diffraction pattern of the crystal of n-propyl acetate/2-propanol solvate of a p-toluenesulfonic acid salt of the compound (IA) of the present invention.

A result of the X-ray powder diffraction of the undried product (8) prepared in step 5 of Example 1-1 above is shown in FIG. 10 and Table 11.

TABLE 11

| 2θ (°) | d Values (Angstrom) | Intensities Counts | Relative (%) |
|---|---|---|---|
| 6.5 | 13.58288 | 39.7 | 100 |
| 7.8 | 11.39666 | 13.3 | 33.6 |
| 8.3 | 10.60256 | 23.9 | 60.1 |
| 9.6 | 9.16463 | 20.4 | 51.4 |
| 9.8 | 8.97311 | 22.3 | 56.2 |
| 10.6 | 8.37508 | 14.1 | 35.4 |
| 11.1 | 7.93822 | 13.1 | 33 |
| 12.1 | 7.28269 | 10.7 | 26.9 |
| 13.7 | 6.44289 | 10.8 | 27.2 |
| 14.8 | 5.99503 | 13.1 | 33 |
| 15.1 | 5.8438 | 16 | 40.2 |
| 15.5 | 5.7282 | 25.2 | 63.4 |
| 16.8 | 5.26409 | 32.1 | 80.8 |
| 17.8 | 4.98851 | 20.3 | 51.1 |
| 18.3 | 4.84562 | 38.1 | 95.8 |
| 18.5 | 4.788 | 25.5 | 64.3 |
| 19.2 | 4.62087 | 20.3 | 51.1 |
| 19.7 | 4.50772 | 24.1 | 60.7 |
| 20.6 | 4.29859 | 27.3 | 68.6 |
| 21.1 | 4.21089 | 22.8 | 57.3 |
| 21.9 | 4.05815 | 25.6 | 64.4 |
| 23.5 | 3.77591 | 19 | 47.8 |
| 24.0 | 3.70351 | 20.2 | 50.7 |
| 24.5 | 3.62451 | 20.7 | 52 |
| 25.5 | 3.49435 | 17.5 | 43.9 |
| 25.7 | 3.46323 | 19.8 | 49.7 |
| 26.8 | 3.32049 | 16.9 | 42.4 |
| 27.5 | 3.24292 | 14.3 | 36.1 |
| 28.3 | 3.14644 | 15.2 | 38.1 |
| 28.9 | 3.08698 | 12.8 | 32.2 |

TABLE 11-continued

| 2θ (°) | d Values (Angstrom) | Intensities Counts | Relative (%) |
|---|---|---|---|
| 32.5 | 2.75453 | 10.9 | 27.5 |
| 33.2 | 2.69838 | 12.3 | 30.9 |

Figure 23:
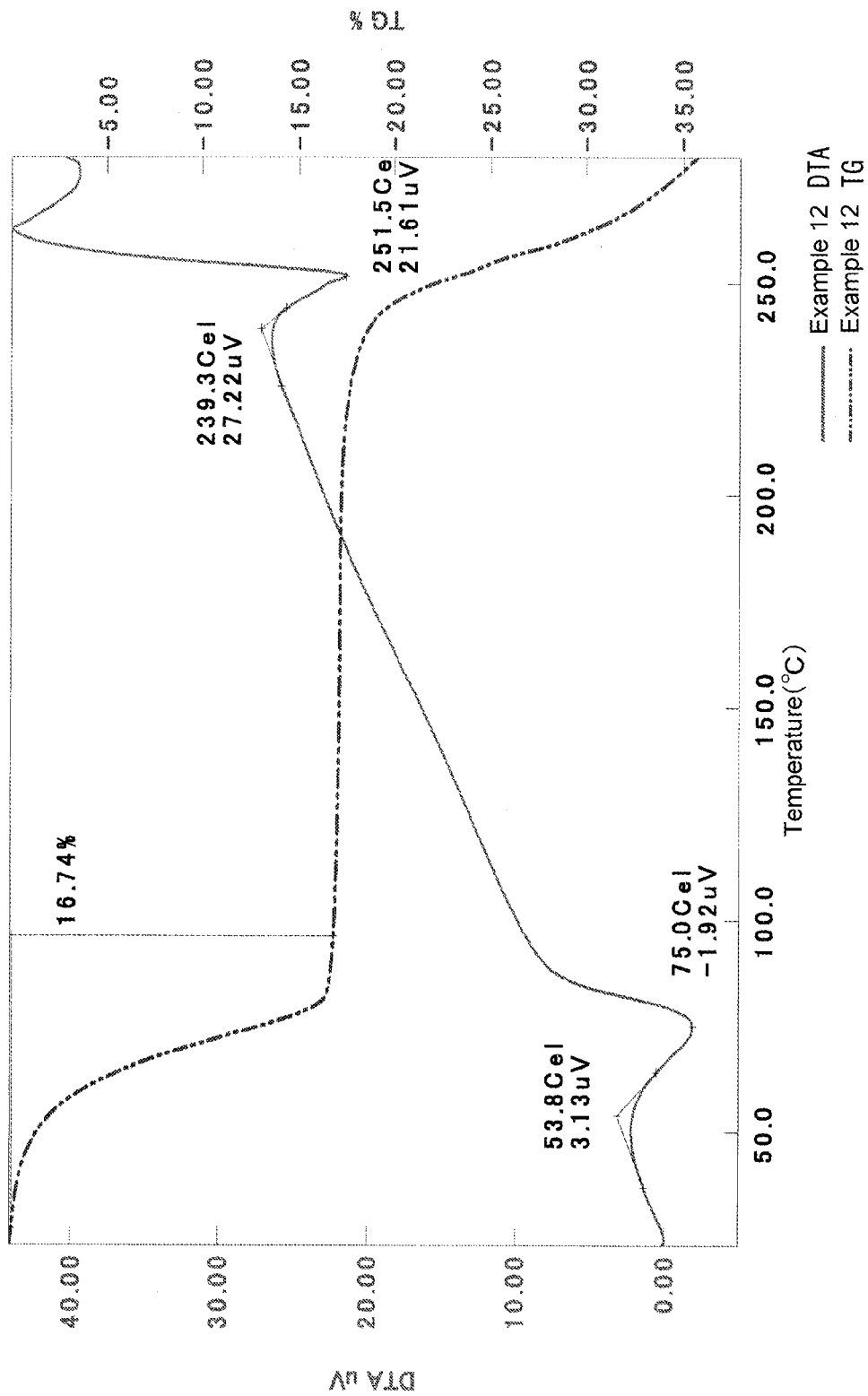
FIG. 23 shows results of TG/DTA analyses of ethyl acetate/2-propanol) solvate of a p-toluenesulfonic acid salt of the compound (IA) in the present invention.

In the X-ray powder diffraction spectrum, peaks were observed at diffraction angles of (2θ): 6.5°±0.2°, 8.3°±0.2°, 15.5°±0.2°, 16.8°±0.2° and 18.3°±0.2°. Results of TG/DTA analysis are shown in FIG. 23.

Example 13

Preparation of acetonitrile solvate of p-toluenesulfonic acid salt of compound (IA)

A mixture of 2-propanol (5 mL)-water (0.5 mL) was added to p-toluenesulfonic acid salt (non-solvate; 1.0 g) prepared according to Example 1-1 above, and dissolved by warming. Acetonitrile (15 mL) was added and stirred at room temperature for 4 hours. The precipitate was collected by filtration to give crystal (1.02 g).

Figure 11:
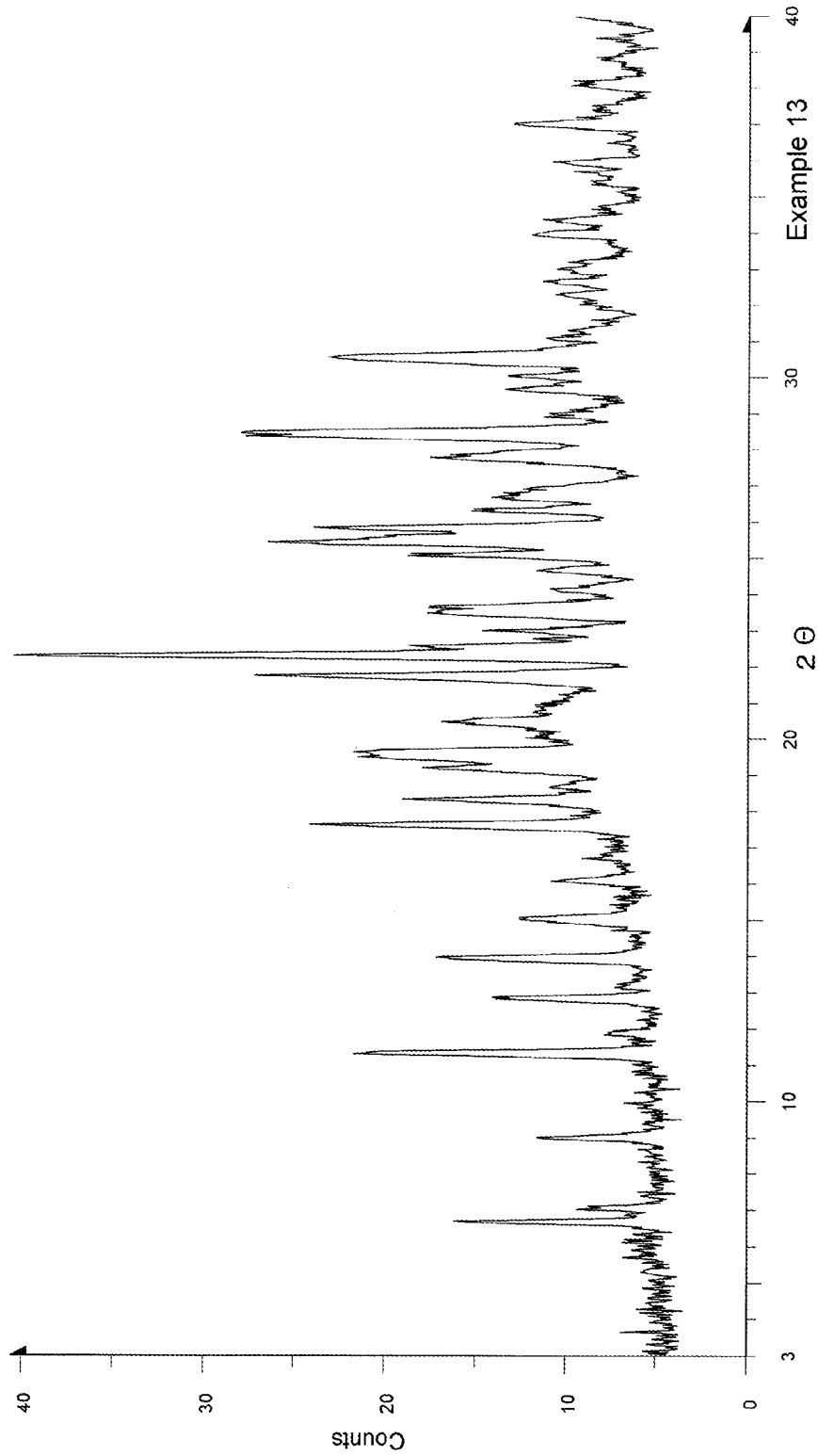
FIG. 11 shows an X-ray-powder-diffraction pattern of the crystal of acetonitrile solvate of a p-toluenesulfonic acid salt of the compound (IA) in the present invention.

Results of X-ray powder diffraction are shown in FIG. 11 and Table 12.

TABLE 12

| 2θ (°) | d Values (Angstrom) | Intensities Counts | Relative (%) |
|---|---|---|---|
| 6.6 | 13.3018 | 16.1 | 39.8 |
| 7.0 | 12.56436 | 9.16 | 22.6 |
| 9.0 | 9.84899 | 11.5 | 28.4 |
| 11.3 | 7.82437 | 21.6 | 53.2 |
| 11.9 | 7.45858 | 7.56 | 18.6 |
| 12.8 | 6.8999 | 14 | 34.5 |
| 13.9 | 6.35422 | 17.1 | 42.2 |
| 15.0 | 5.8955 | 12.5 | 30.7 |
| 16.1 | 5.51292 | 10.7 | 26.4 |
| 17.6 | 5.03059 | 24.1 | 59.4 |
| 18.3 | 4.84288 | 19 | 46.9 |
| 19.2 | 4.62372 | 17.9 | 44.1 |
| 19.6 | 4.5284 | 20.8 | 51.2 |
| 20.5 | 4.33273 | 16.9 | 41.6 |
| 21.7 | 4.08494 | 27.2 | 67.1 |
| 22.3 | 3.98365 | 40.6 | 100 |
| 22.6 | 3.93452 | 18.7 | 46 |
| 23.0 | 3.86409 | 14.6 | 36 |
| 23.6 | 3.76723 | 17.5 | 43.3 |
| 24.1 | 3.68454 | 10.8 | 26.7 |
| 24.7 | 3.60615 | 11.6 | 28.6 |
| 25.1 | 3.54709 | 18.7 | 46.1 |
| 25.4 | 3.49901 | 26.5 | 65.3 |
| 25.8 | 3.44756 | 23.9 | 58.9 |
| 26.3 | 3.38235 | 15.2 | 37.5 |
| 26.7 | 3.33734 | 14.1 | 34.8 |
| 26.9 | 3.31407 | 12.1 | 29.8 |
| 27.8 | 3.2085 | 17.5 | 43.2 |
| 28.5 | 3.134 | 28 | 69 |
| 29.0 | 3.07959 | 10.9 | 26.8 |
| 29.7 | 3.0064 | 13.4 | 32.9 |
| 30.1 | 2.97013 | 13.2 | 32.6 |
| 30.6 | 2.92269 | 23.1 | 56.9 |
| 32.3 | 2.76801 | 10.6 | 26.2 |
| 32.7 | 2.73818 | 11.3 | 27.8 |
| 34.0 | 2.63491 | 11.7 | 28.9 |
| 34.4 | 2.60666 | 11.3 | 27.9 |
| 36.0 | 2.49457 | 10.7 | 26.5 |
| 37.0 | 2.42546 | 12.9 | 31.8 |
| 38.1 | 2.35805 | 9.28 | 22.9 |

TABLE 12-continued

| 2θ (°) | d Values (Angstrom) | Intensities Counts | Relative (%) |
|---|---|---|---|
| 38.9 | 2.316 | 8.38 | 20.7 |
| 39.4 | 2.28473 | 8.38 | 20.7 |

Figure 24:
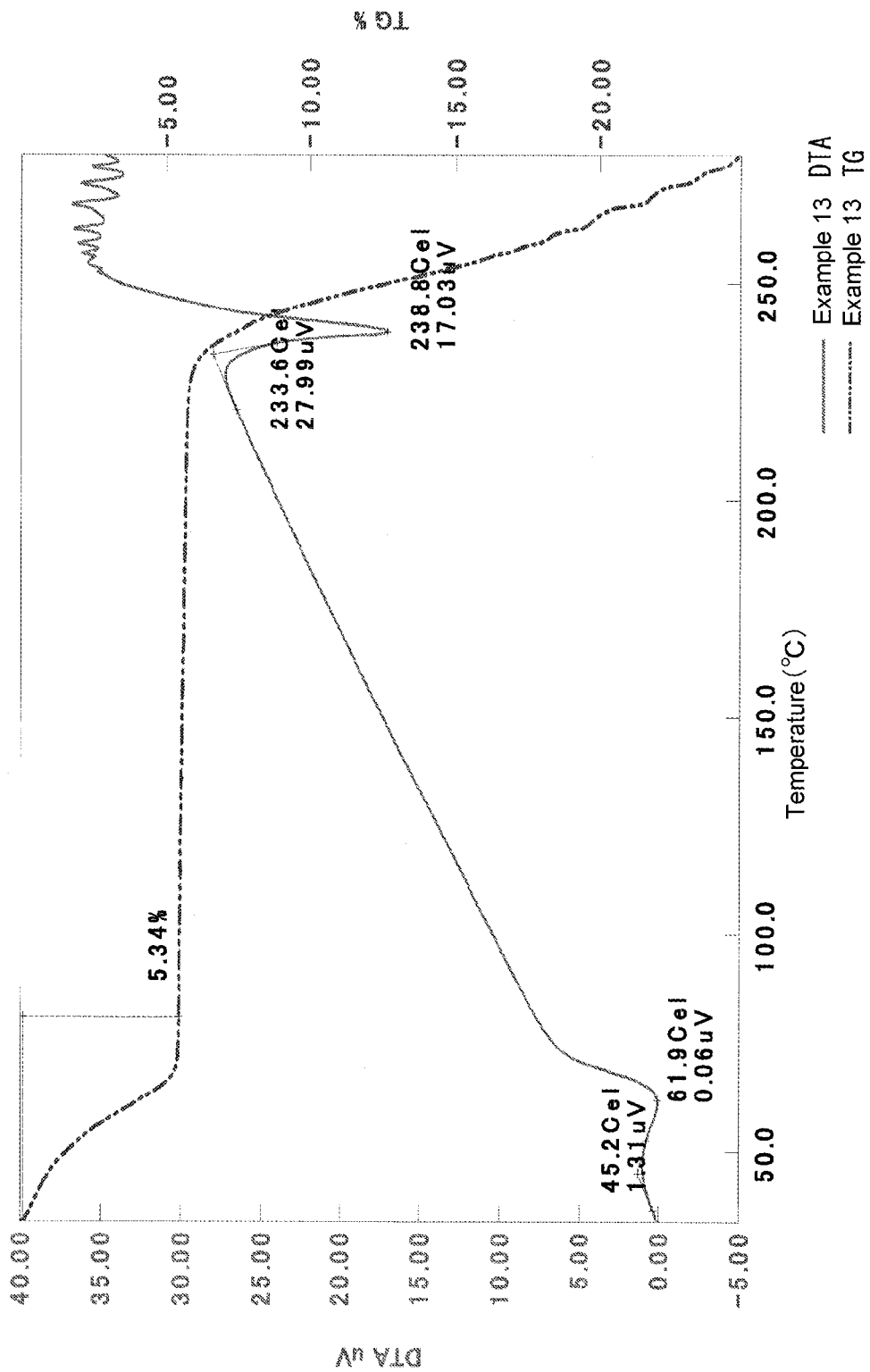
FIG. 24 shows results of TG/DTA analyses of acetonitrile solvate of a p-toluenesulfonic acid salt of the compound (IA) in the present invention.

In the X-ray powder diffraction spectrum, peaks were observed at diffraction angles of (2θ): 11.3°±0.2°, 17.6°±0.2°, 21.7°±0.2°, 22.3°±0.2° and 28.5°±0.2°. Results of TG/DTA analysis are shown in FIG. 24.

Example 14

Preparation of 1,2-dimethoxyethane solvate of p-toluenesulfonic acid salt of compound (IA)

Tetrahydrofuran (5 mL) was added to p-toluenesulfonic acid salt (non-solvate; 1.0 g) prepared according to Example 1-1 above, and dissolved it by warming. 1,2-Dimethoxyethane (20 mL) was added and stirred at room temperature for 4 hours. The precipitate was collected by filtration to give the crystal (1.05 g).

Figure 12:
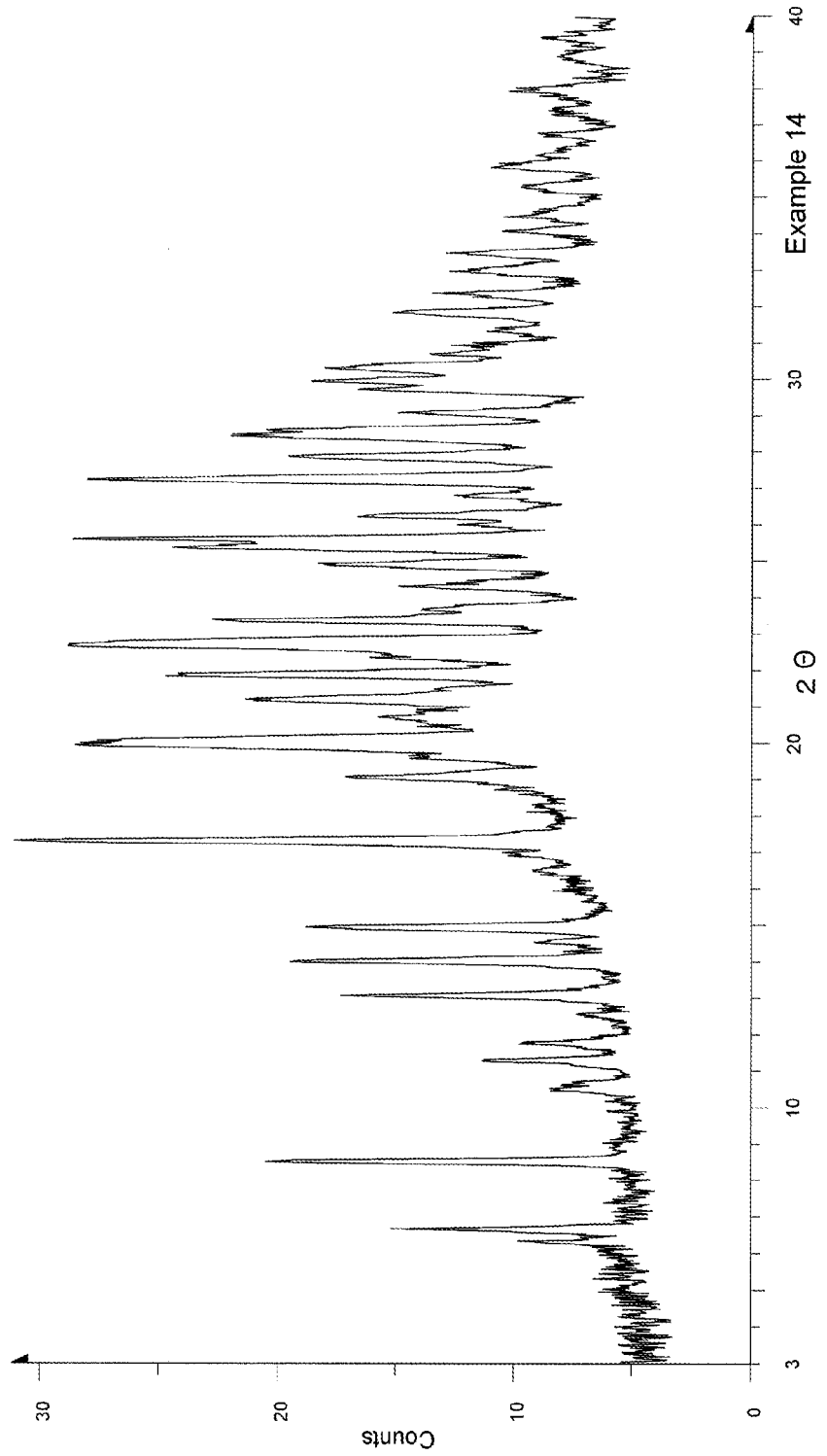
FIG. 12 shows an X-ray-powder-diffraction pattern of the crystal of 1,2-diethoxyethane solvate of a p-toluenesulfonic acid salt of the compound (IA) in the present invention.

A result of the X-ray powder diffraction is shown in FIG. 12 and Table 13.

TABLE 13

| 2θ (°) | d Values (Angstrom) | Intensities Counts | Relative (%) |
|---|---|---|---|
| 6.3 | 14.0539 | 9.82 | 31.5 |
| 6.6 | 13.33769 | 15.1 | 48.6 |
| 8.5 | 10.39712 | 20.5 | 65.7 |
| 10.5 | 8.43144 | 8.5 | 27.3 |
| 11.3 | 7.84523 | 11.3 | 36.3 |
| 11.7 | 7.53149 | 9.8 | 31.4 |
| 13.0 | 6.7854 | 17.3 | 55.5 |
| 14.0 | 6.32458 | 19.3 | 61.9 |
| 14.5 | 6.08925 | 8.84 | 28.3 |
| 14.9 | 5.93716 | 18.8 | 60.4 |
| 17.3 | 5.12267 | 31.2 | 100 |
| 19.1 | 4.65465 | 17.1 | 54.9 |
| 20.0 | 4.44407 | 28.6 | 91.7 |
| 20.7 | 4.2889 | 15.7 | 50.5 |
| 21.2 | 4.19011 | 21.4 | 68.7 |
| 21.9 | 4.06234 | 24.2 | 77.6 |
| 22.7 | 3.91588 | 28.9 | 92.7 |
| 23.4 | 3.80648 | 22.8 | 73.2 |
| 23.7 | 3.75384 | 13.9 | 44.5 |
| 24.3 | 3.66115 | 14.9 | 47.7 |
| 24.9 | 3.57408 | 18.3 | 58.6 |
| 25.4 | 3.50782 | 24.5 | 78.5 |
| 25.6 | 3.47931 | 28.7 | 92 |
| 26.2 | 3.39416 | 16.3 | 52.4 |
| 26.8 | 3.32443 | 12.5 | 40.2 |
| 27.2 | 3.27281 | 28.1 | 90 |
| 27.9 | 3.20033 | 19.6 | 62.9 |
| 28.5 | 3.13464 | 22 | 70.6 |
| 29.1 | 3.06716 | 14.9 | 47.8 |
| 29.7 | 3.00284 | 16.6 | 53.3 |
| 30.0 | 2.97951 | 18.6 | 59.6 |
| 30.3 | 2.94574 | 18 | 57.8 |
| 31.8 | 2.80853 | 15.1 | 48.5 |
| 32.4 | 2.76482 | 13.5 | 43.2 |
| 33.0 | 2.71363 | 12.8 | 40.9 |
| 33.5 | 2.67462 | 12.9 | 41.3 |
| 34.1 | 2.62874 | 10.5 | 33.8 |
| 35.3 | 2.53958 | 9.78 | 31.4 |
| 35.8 | 2.50305 | 11 | 35.4 |
| 36.8 | 2.44304 | 8.99 | 28.8 |

TABLE 13-continued

|  | d Values | Intensities | |
| --- | --- | --- | --- |
| 2θ (°) | (Angstrom) | Counts | Relative (%) |
| 38.0 | 2.36586 | 9.86 | 31.6 |
| 38.9 | 2.31271 | 8.29 | 26.6 |

In the X-ray powder diffraction spectrum, peaks were observed at diffraction angles of (2θ): 8.5°±0.2°, 13.0°±0.2°, 14.0°±0.2°, 14.9°±0.2°, 17.3°±0.2°, 20.0°±0.2°, 21.9°±0.2°, 22.7°±0.2°, 25.6°±0.2° and 27.2°±0.2°.

Figure 25:
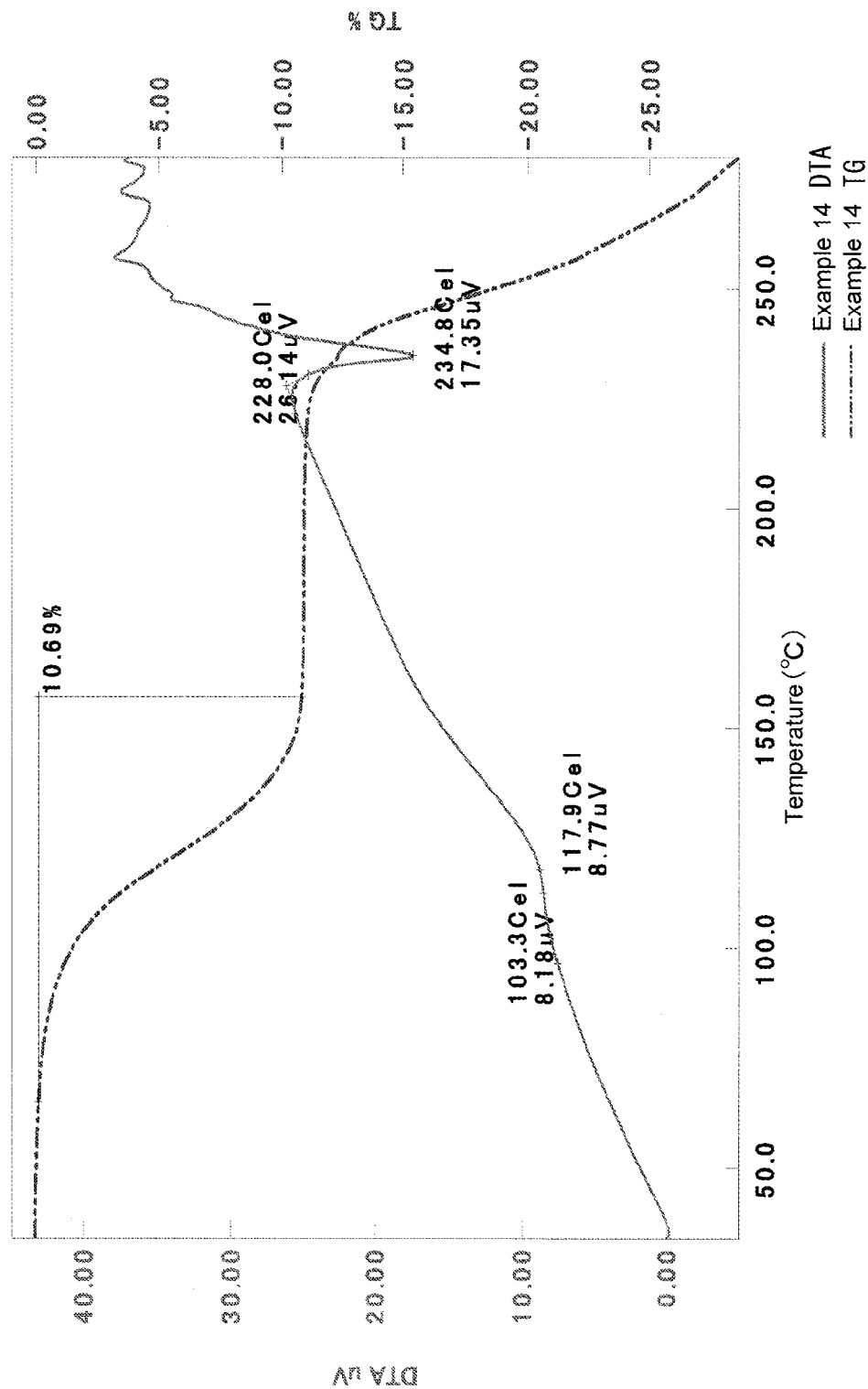
FIG. 25 shows results of TG/DTA analyses of 1,2-dimethoxyethane solvate of a p-toluenesulfonic acid salt of the compound (IA) in the present invention.

Results of TG/DTA analysis are shown in FIG. 25.

Example 15

Preparation of methyl-isobutyl-ketone solvate of the p-toluenesulfonic acid salt of compound (IA)

Tetrahydrofuran (5 mL) was added to p-toluenesulfonic acid salt (non-solvate; 1.0 g) prepared according to Example 1-1 above, and dissolved it by warming. Methyl isobutyl ketone (20 mL) was added and stirred at room temperature for 4 hours. The precipitate was collected by filtration to give the crystal (1.02 g).

Figure 13:
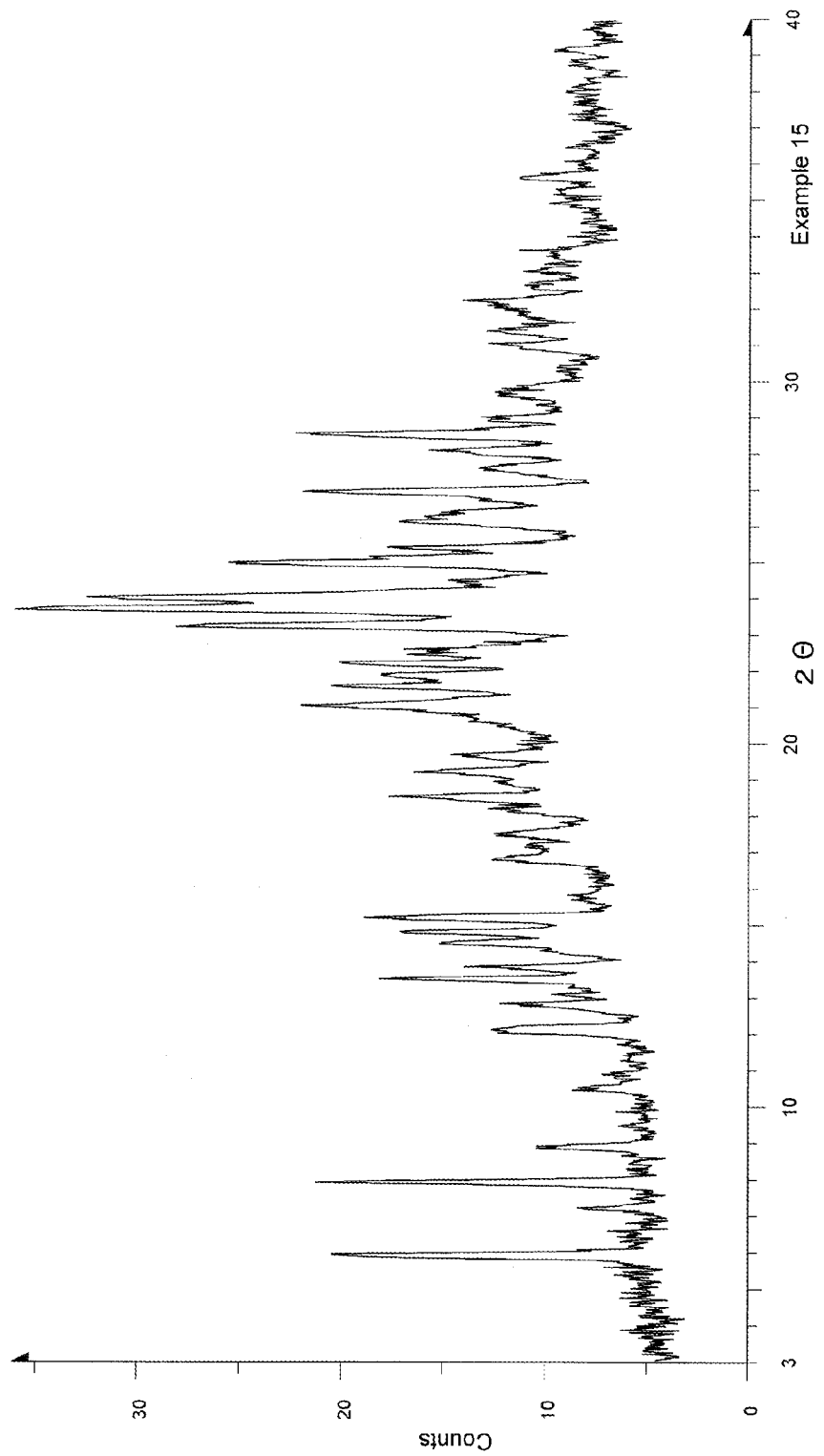
FIG. 13 shows an X-ray-powder-diffraction pattern of the crystal of methyl isobutyl ketone solvate of a p-toluenesulfonic acid salt of the compound (IA) in the present invention.

A result of the X-ray powder diffraction is shown in FIG. 13 and Table 14.

TABLE 14

|  | d Values | Intensities | |
| --- | --- | --- | --- |
| 2θ (°) | (Angstrom) | Counts | Relative (%) |
| 5.9 | 15.01981 | 20.5 | 58.2 |
| 7.2 | 12.28096 | 8.37 | 23.7 |
| 7.9 | 11.18559 | 21.2 | 60.3 |
| 8.9 | 9.95187 | 10.4 | 29.5 |
| 10.5 | 8.42832 | 8.36 | 23.7 |
| 12.1 | 7.31068 | 12.6 | 35.8 |
| 12.8 | 6.91103 | 12.2 | 34.5 |
| 13.5 | 6.55499 | 18.1 | 51.4 |
| 13.8 | 6.40153 | 13.9 | 39.5 |
| 14.5 | 6.10583 | 15 | 42.7 |
| 14.8 | 5.98221 | 17.1 | 48.6 |
| 15.2 | 5.82819 | 18.9 | 53.6 |
| 16.8 | 5.27057 | 12.6 | 35.7 |
| 17.5 | 5.0641 | 12.5 | 35.4 |
| 18.2 | 4.87769 | 12.8 | 36.3 |
| 18.5 | 4.78796 | 17.7 | 50.1 |
| 19.2 | 4.61527 | 16.4 | 46.6 |
| 19.6 | 4.51531 | 14 | 39.8 |
| 21.0 | 4.22071 | 22 | 62.4 |
| 21.6 | 4.11729 | 20.5 | 58.2 |
| 21.9 | 4.06212 | 18.1 | 51.3 |
| 22.2 | 4.0009 | 20 | 56.7 |
| 22.5 | 3.94891 | 15.7 | 44.5 |
| 23.2 | 3.8243 | 28.1 | 79.9 |
| 23.7 | 3.74808 | 35.2 | 100 |
| 24.0 | 3.704 | 32.2 | 91.3 |
| 24.5 | 3.63504 | 14.3 | 40.7 |
| 25.0 | 3.56011 | 25.6 | 72.6 |
| 25.4 | 3.50092 | 17.8 | 50.5 |
| 26.2 | 3.40438 | 17.1 | 48.4 |
| 26.4 | 3.37826 | 15.2 | 43.2 |
| 27.0 | 3.30417 | 21.9 | 62.3 |
| 27.6 | 3.22776 | 13.2 | 37.6 |
| 28.1 | 3.17404 | 15.7 | 44.6 |
| 28.5 | 3.12449 | 21.6 | 61.3 |
| 29.0 | 3.07854 | 12.7 | 36 |
| 29.7 | 3.00993 | 12.3 | 34.8 |
| 31.0 | 2.88098 | 12.1 | 34.4 |
| 31.4 | 2.84529 | 12.9 | 36.6 |
| 32.2 | 2.77633 | 14 | 39.8 |
| 32.6 | 2.7414 | 11.1 | 31.6 |

TABLE 14-continued

|  | d Values | Intensities | |
| --- | --- | --- | --- |
| 2θ (°) | (Angstrom) | Counts | Relative (%) |
| 35.7 | 2.516 | 11.4 | 32.3 |
| 39.2 | 2.29767 | 9.67 | 27.4 |

In the X-ray powder diffraction spectrum, peaks were observed at diffraction angles of (2θ): 5.9°±0.2°, 7.9°±0.2°, 13.5°±0.2°, 15.2°±0.2°, 23.2°±0.2°, 23.7°±0.2°, 24.0°±0.2°, 25.0°±0.2°, 27.0°±0.2° and 28.5°±0.2°.

Figure 26:
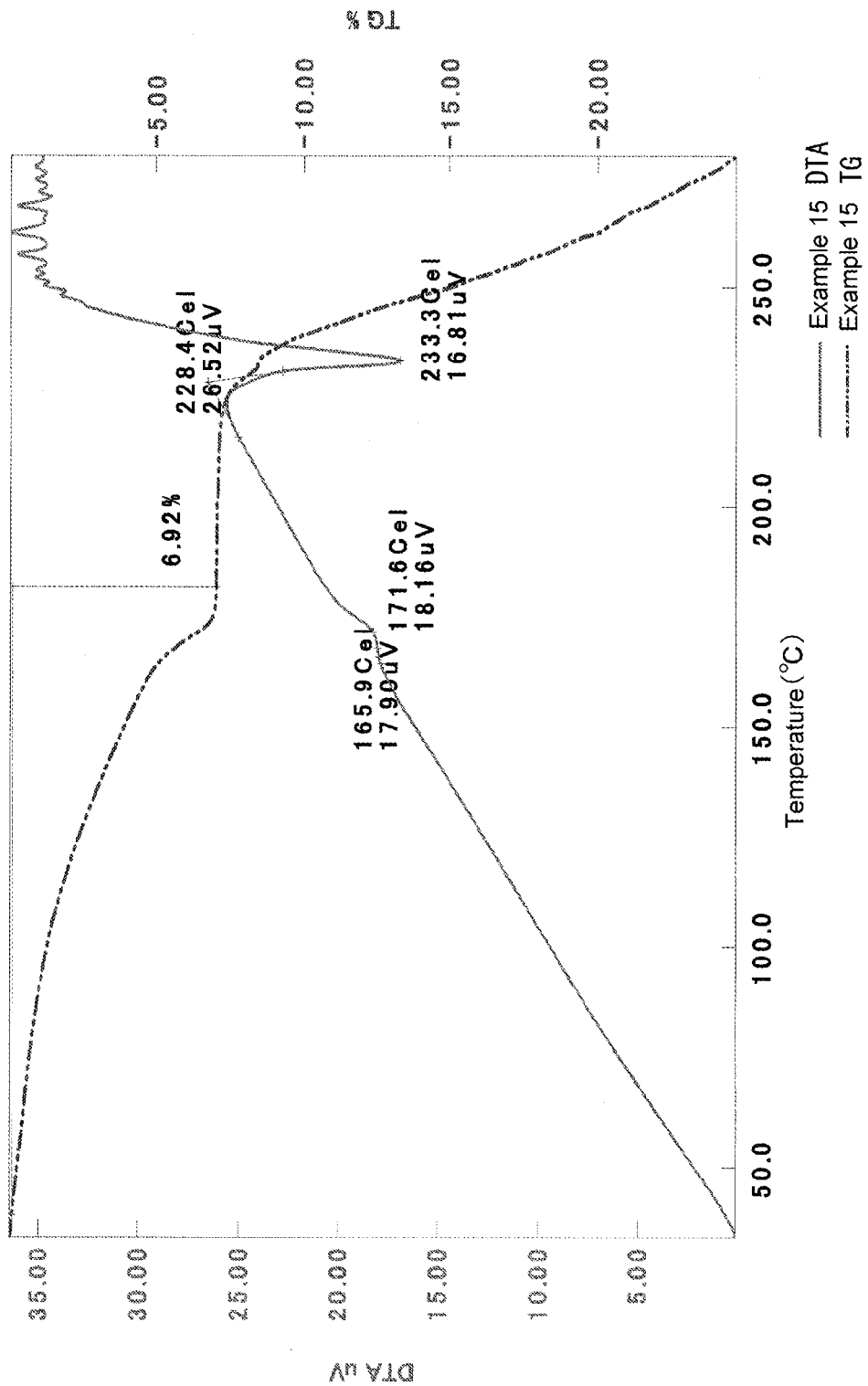
FIG. 26 shows results of TG/DTA analyses of methyl isobutyl ketone solvate of a p-toluenesulfonic acid salt of the compound (IA) in the present invention.

Results of TG/DTA analysis are shown in FIG. 26.

Test Example 1

The Solid Stability Test of Crystal

About 10 mg of crystal was correctly weighed in the 2-mL glass container with a stopper made of polyethylene.

After closing the glass container, it was rolled with parafilm, and stored for two or four weeks at 40° C. or 60° C. The sample stored at 40° C. is called 40° C. with airtight stopper, and the sample saved at 60° C. is called 60° C. with airtight stopper.

Also samples were reserved with the glass container opened at 40° C., relative humidity 89%, or 60° C., for two weeks or four weeks. The sample stored at 40° C. and relative humidity 89% is called 40° C. R.H. 89%, and the sample stored at 60° C. is called 60° C. Opened.

Using samples with airtight stopper stored at −40° C. as a standard, the content was measured with the absolute calibration method by the HPLC method under the following conditions:

In Table 16 were shown a remaining of the crystal and a result of observation for the change of appearance in p-toluenesulfonic acid salt (non-solvate) of compound (IA).

In Table 17 were shown a remaining of the crystal and a result of observation for the change of appearance in p-toluenesulfonic acid salt hydrate (form I) of compound (IA).

In Table 18 were shown a remaining of the crystal and a result of observation for the change in appearance in p-toluenesulfonic acid salt hydrate (form II) of compound (IA).

In addition, when there was no change in appearance, an evaluation was (−), and when there was a little change observed, it was (±).

There was no change in the appearance in p-toluenesulfonic acid salt (non-solvate), p-toluenesulfonic acid salt hydrate (form I) or p-toluenesulfonic acid salt hydrate (form II), the decreasing in content of each crystal was not observed and each crystal was stable.

HPLC Conditions

Column: CAPCELL PAK C18 AQ (3 micrometer 3.0×150 mm)

Column temperature: 50° C.

UV detection wavelength: 231 nm

Mobile phase: A gradient elution was carried out as shown in Table 15.

[A] A mixed solution containing ammonium formate (10 mmol/L) and magnesium chloride (10 mmol/L)

[B] Acetonitrile

TABLE 15

| Time (min) | [A] (%) | [B] % |
| --- | --- | --- |
| 0 | 65 | 35 |
| 10 | 65 | 35 |

TABLE 15-continued

| Time (min) | [A] (%) | [B] % |
|---|---|---|
| 20 | 30 | 70 |
| 25 | 30 | 70 |
| 25.1 | 65 | 35 |
| 30 | 65 | 35 |

TABLE 16

| Storage Condition | Storage Period (weeks) | Change of Appearance | Survival Rate (%) |
|---|---|---|---|
| Standard | 2 | | 100.0 |
| Standard | 4 | | 100.0 |
| 60° C. airtight stopper | 2 | − | 99.9 |
| 60° C. airtight stopper | 4 | − | 99.6 |
| 60° C. Opened | 2 | − | 100.3 |
| 60° C. Opened | 4 | − | 98.8 |
| 40° C. R.H. 89% | 2 | − | 99.3 |
| 40° C. R.H. 89% | 4 | − | 100.5 |
| 40° C. airtight stopper | 4 | − | 98.0 |

TABLE 17

| Storage Condition | Storage Period (weeks) | Change of Appearance | Survival Rate (%) |
|---|---|---|---|
| Standard | 2 | | 100.0 |
| Standard | 4 | | 100.0 |
| 60° C. airtight stopper | 2 | − | 100.8 |
| 60° C. airtight stopper | 4 | ± | 99.2 |
| 60° C. Opened | 2 | − | 100.5 |
| 60° C. Opened | 4 | ± | 98.5 |
| 40° C. R.H. 89% | 2 | − | 101.2 |
| 40° C. R.H. 89% | 4 | ± | 98.4 |

TABLE 18

| Storage Condition | Storage Period (weeks) | Change of Appearance | Survival Rate (%) |
|---|---|---|---|
| Standard | 2 | | 100.0 |
| Standard | 4 | | 100.0 |
| 60° C. airtight stopper | 2 | − | 102.0 |
| 60° C. airtight stopper | 4 | ± | 100.6 |
| 60° C. Opened | 2 | − | 100.7 |
| 60° C. Opened | 4 | ± | 100.4 |
| 40° C. R.H. 89% | 2 | − | 100.9 |
| 40° C. R.H. 89% | 4 | ± | 100.1 |

Test Example 2

Confirmatory Test for Hygroscopicity of Crystal

About 10 mg of p-toluenesulfonic acid salt (non-solvate) of the formula (IA) was sampled in a specimen container for automated water vapor sorption apparatus, and dried at 25° C. under dried nitrogen atmosphere. After completion of the drying, relative humidity was continuously changed at intervals of 5% in a range from 0% to 95% and the amount of water vapor adsorption and desorption of the sample was measured with automated water vapor sorption apparatus: DVS Advantage (Surface Measurement Systems).

A result was shown in Table 19. An amount of the maximum moisture absorption of the crystal of the p-toluenesulfonic acid salt (non-solvate) of the formula (IA) in the range of 0% to 95% of relative humidity at 25° C. is less than 1.2%, and hygroscopicity was little observed in the crystal.

TABLE 19

| R.H. (%) | Changes (%) | |
|---|---|---|
| | Adsorption | Desiroption |
| 0.0 | 0.000 | 0.011 |
| 5.0 | 0.075 | 0.118 |
| 10.0 | 0.126 | 0.186 |
| 15.0 | 0.184 | 0.255 |
| 20.0 | 0.233 | 0.318 |
| 15.0 | 0.282 | 0.374 |
| 30.0 | 0.329 | 0.430 |
| 35.0 | 0.377 | 0.484 |
| 40.0 | 0.425 | 0.544 |
| 45.0 | 0.474 | 0.607 |
| 50.0 | 0.522 | 0.666 |
| 55.0 | 0.569 | 0.715 |
| 60.0 | 0.615 | 0.758 |
| 65.0 | 0.668 | 0.806 |
| 70.0 | 0.732 | 0.857 |
| 75.0 | 0.788 | 0.899 |
| 80.0 | 0.849 | 0.943 |
| 85.0 | 0.917 | 0.995 |
| 90.0 | 0.999 | 1.059 |
| 95.0 | 1.137 | 1.137 |

Formulation Example 1

A granule containing the following components is prepared.

TABLE 15

| Ingredients | compound represented by the formula (IA) | 10 mg |
|---|---|---|
| | lactose | 700 mg |
| | corn starch | 274 mg |
| | HPC-L | 16 mg |
| | | 1000 mg |

"Compound represented by the formula (IA)" above includes a free form, an acid addition salt and/or a solvate thereof.

Compound represented by the formula (IA) and lactose are passed through a 60-mesh sieve. Corn starch is passed through a 120-mesh sieve. These are mixed in a V shaped rotary mixer. An aqueous solution of HPC-L (Lower-viscosity hydroxypropyl cellulose) is added to the mixed powder, and the mixture is kneaded, granulated and a drying process is conducted. The dried granule obtained is filtered through a vibrating strainer (12/60 mesh) to give a granular formulation.

Formulation Example 2

A granule for encapsulation containing the following ingredients is prepared.

TABLE 16

| Ingredients | compound represented by the formula (IA) | 15 mg |
|---|---|---|
| | lactose | 90 mg |
| | corn starch | 42 mg |
| | HPC-L | 3 mg |
| | | 150 mg |

"Compound represented by the formula (IA)" above includes a free form, an acid addition salt and/or a solvate thereof.

Compound represented by the formula (IA) and lactose are passed through a 60-mesh sieve. Corn starch is passed through a 120-mesh sieve. These are mixed and an aqueous solution of HPC-L is added to the mixed powder, and the mixture is kneaded, granulated and dried. A particle size of the dried granule obtained is regulated and a No. 4 hard gelatin capsule is filled up with 150 mg of the granule.

Formulation Example 3

A tablet containing the following ingredients is prepared.

TABLE 17

| Ingredients | compound represented by the formula (IA) | 10 mg |
|---|---|---|
| | lactose | 90 mg |
| | microcrystalline cellulose | 30 mg |
| | CMC-Na | 15 mg |
| | magnesium stearate | 5 mg |
| | | 150 mg |

"Compound represented by the formula (IA)" above includes a free form, an acid addition salt and/or a solvate thereof.

Compound represented by the formula (IA), lactose, microcrystalline cellulose and CMC-Na (sodium carboxymethyl cellulose) are passed through 60-mesh sieve and mixed. Magnesium stearate is mixed with the mixed powder and a mixed powder for tablet is obtained. This powder is tableted to give a tablet of 150 mg.

Formulation Example 4

The following ingredients are mixed under warming and sterilized to give an injection.

TABLE 18

| Ingredients | compound represented by the formula (IA) | 3 mg |
|---|---|---|
| | non-ionic surfactant | 15 mg |
| | purified water for injection | 1 ml |

"Compound represented by the formula (IA)" above includes a free form, an acid addition salt and/or a solvate thereof.

Industrial Applicability

The present invention provides a 6,7-unsaturated-7-carbamoyl morphinan derivative, an acid addition salt, a solvate and/or a stable crystal thereof, useful as a material for preparing a medicine.

The present invention also provides a 6,7-unsaturated-7-carbamoyl morphinan derivative, an acid addition salt, a solvate and/or a stable crystal thereof, which is useful for treating and/or preventing nausea, emesis and/or constipation induced by a compound having an opioid receptor agonistic activity, and a novel process for preparing crystal thereof.

The invention claimed is:

1. A p-toluenesulfonic acid salt of a compound of the formula (IA):

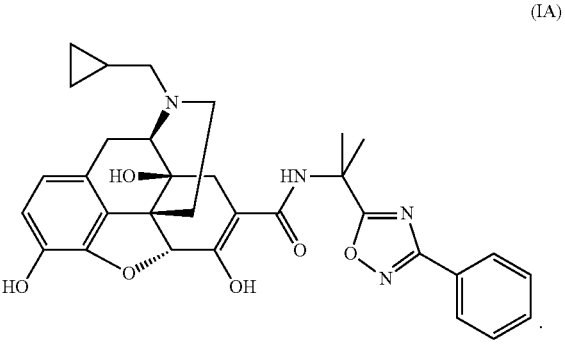 [SMILES: CC(C)(NC(=O)C1=C(O)[C@@H]2Oc3c(O)ccc4c3[C@@]23CCN(CC2CC2)[C@H](C4)[C@]3(O)C1)c1nc(-c2ccccc2)no1]

(IA)

2. A crystal of a p-toluenesulfonic acid salt of a compound of the formula (IA):

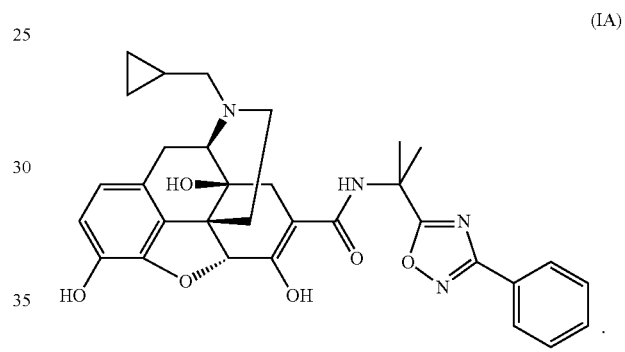

(IA)

3. The crystal of the p-toluenesulfonic acid salt according to claim 2, wherein the X-ray powder diffraction spectrum of the crystal has peaks at diffraction angles (2θ) of: 7.8°±0.2°, 10.6°,±0.2°, 15.6°±0.2, 17.8°±0.2° and 21.5°±0.2°.

4. The crystal of the p-toluenesulfonic acid salt according to claim 2, wherein the X-ray powder diffraction spectrum of the crystal has peaks at diffraction angles (2θ) of: 7.8°±0.2°, 10.6°±0.2°, 15.6°±0.2°, 18.6°,±0.2°, 20.4°±0,2°, 21.9°±0.2°, 23.6°±0.2° and 25.5°±0.2°.

5. The crystal of the p-toluenesuifonic acid salt according to claim 2, wherein the X-ray powder diffraction spectrum of the crystal is substantially identical to FIG. 1.

6. The crystal of the p-toluenesuifonic acid salt according to claim 2, wherein the X-ray powder diffraction spectrum of the crystal has peaks at diffraction angles (2θ) of: 12.9°±0.2°, 17.6°±0.2°, 22.4°,02°, 25.4°±0,2° and 28.7°±0.2°.

7. The crystal of the p-toluenesulfonic acid salt according to claim 2, wherein the X-ray powder diffraction spectrum of the crystal has peaks at diffraction angles (2θ) of: 6.6°±0.2°, 8.9°±0.2°11.4°±0.2°, 12.9°±0.2°, 14.0°±0.2°, 15.0°±0.2°, 17.6°±0.2°, 18.2°±0.2°22.4°±0.2°25.4°±0.2° and 28.7°.±0.2°.

8. The crystal of the p-toluenesulfonic acid salt according to claim 2, wherein the X-ray powder diffraction spectrum of the crystal is substantially identical to FIG. 2.

9. The crystal of the p-toluenesulfonic acid salt according to claim 2, wherein the X-ray powder diffraction spectrum of the crystal has peaks at diffraction angles (2θ) of: 8.8°±0.2°, 17.5°±0.2°, 21.9°±0.2°, 23.7°±0.2° and 26.1°±0.2°.

10. The crystal of the p-toluenesulfonic acid salt according to claim 2, wherein the X-ray powder diffraction spectrum of the crystal has peaks at diffraction angles (2θ) of: 7.1°±0.2°, 8.8°±0.2°, 17.5°±0.2°, 19.2°±0.2°, 19.7°±0.2°, 21.2°±0.2°, 21.9°±0.2°23.7°±0.2°, 24.5°±0.2° and 26.1°±0.2°.

11. The crystal of the p-toluenesulfonic acid salt according to claim 2, wherein the X-ray powder diffraction spectrum of the crystal is substantially identical to FIG. 3.

12. A pharmaceutical composition comprising the crystal according to claim 2.

13. The crystal of the p-toluenesulfonic acid salt according to claim 2, wherein the salt is a non-solvate.

14. The crystal of the p-toluenesulfonic acid salt according to claim 2, wherein the salt is a hydrate.

15. The crystal of the p-toluenesulfonic acid salt according to claim 14, wherein the crystal is Form I hydrate.

16. The crystal of the p-toluenesulfonic acid salt according to claim 14, wherein the crystal is Form II hydrate.

17. The p-toluenesulfonic acid salt of claim 1, wherein the salt is a hydrate, 18. The p-toluenesulfonic acid salt of claim 1, wherein the salt is a non-solvate,

\* \* \* \* \*